United States Patent
Blum et al.

(10) Patent No.: US 8,113,651 B2
(45) Date of Patent: Feb. 14, 2012

(54) HIGH PERFORMANCE CORNEAL INLAY

(75) Inventors: Ronald D. Blum, Roanoke, VA (US);
Andrew W. Ishak, Waterford, VT (US);
Peter Haaland, Arlington, VA (US);
Michael B. Packard, Cincinnati, OH (US); D. James Schumer, Mansfield, OH (US)

(73) Assignee: High Performance Optics, Inc., Roanoke, VA (US)

( * ) Notice: Subject to any disclaimer, the term of this patent is extended or adjusted under 35 U.S.C. 154(b) by 192 days.

(21) Appl. No.: 12/037,565

(22) Filed: Feb. 26, 2008

(65) Prior Publication Data
US 2008/0221674 A1 Sep. 11, 2008

Related U.S. Application Data

(63) Continuation-in-part of application No. 11/933,069, filed on Oct. 31, 2007, which is a continuation-in-part of application No. 11/761,892, filed on Jun. 12, 2007, now Pat. No. 7,520,608, which is a continuation-in-part of application No. 11/378,317, filed on Mar. 20, 2006, now abandoned, said application No. 11/933,069 is a continuation-in-part of application No. 11/892,460, filed on Aug. 23, 2007, now Pat. No. 7,556,376.

(60) Provisional application No. 60/903,324, filed on Feb. 26, 2007, provisional application No. 60/906,205, filed on Mar. 12, 2007, provisional application No. 60/812,628, filed on Jun. 12, 2006, provisional application No. 60/839,432, filed on Aug. 23, 2006, provisional application No. 60/841,502, filed on Sep. 1, 2006, provisional application No. 60/861,247, filed on Nov. 28, 2006, provisional application No. 60/978,175, filed on Oct. 8, 2007.

(51) Int. Cl.
*G02C 7/02* (2006.01)
*A61F 2/14* (2006.01)
*A61F 2/16* (2006.01)
(52) U.S. Cl. .................. 351/159; 623/4.1; 623/6.11
(58) Field of Classification Search .................. 351/159, 351/160 R, 163–165; 623/4.1, 5.11, 6.11
See application file for complete search history.

(56) References Cited

U.S. PATENT DOCUMENTS 4,017,292 A 4/1977 Mann
(Continued)

FOREIGN PATENT DOCUMENTS

DE 3544627 12/1985
(Continued)

OTHER PUBLICATIONS

Baumeister,P. & Pincus,G. 1970. Optical Interference Coatings. Scientific American.
CRC Handbook of Chemistry and Physics 86th Ed. 2004-2005. pp. 10-217.
NACL website, as archived from Oct. 8, 2000: http://web.archive.org/web/20001008003354//www.nacl.com/custom.htm obtained for WayBack Machine at www.archive.org.

(Continued)

*Primary Examiner* — James Greece
(74) *Attorney, Agent, or Firm* — Kilpatrick Townsend & Stockton LLP

(57) ABSTRACT

A corneal inlay protects ocular structures from harmful wavelengths of light while maintaining acceptable color cosmetics, color perception, overall light transmission, photopic vision, scotopic vision, color vision, and/or cirdadian rhythms. The corneal inlay can also include a pinhole effect to increase depth of focus. In some embodiments, the corneal inlay can also correct refractive errors including, but not limited to, higher order aberration, lower order aberration, myopia, hyperopia, astigmatism, and/or presbyopia.

18 Claims, 38 Drawing Sheets

U.S. PATENT DOCUMENTS

| | | | |
|---|---|---|---|
| 4,247,177 A | 1/1981 | Marks et al. |
| 4,390,676 A | 6/1983 | Loshaek |
| 4,679,918 A | 7/1987 | Ace |
| 4,698,374 A | 10/1987 | Gallas |
| 4,793,669 A | 12/1988 | Perilloux |
| 4,826,286 A * | 5/1989 | Thornton, Jr. | 359/588 |
| 4,878,748 A | 11/1989 | Johansen et al. |
| 4,952,046 A | 8/1990 | Stephens et al. |
| 5,054,902 A | 10/1991 | King |
| 5,172,256 A | 12/1992 | Sethofer et al. |
| 5,177,509 A | 1/1993 | Johansen et al. |
| 5,374,663 A | 12/1994 | Daicho et al. |
| 5,400,175 A | 3/1995 | Johansen et al. |
| 5,470,932 A | 11/1995 | Jinkerson |
| 5,521,765 A | 5/1996 | Wolfe |
| 5,528,322 A | 6/1996 | Jinkerson |
| 5,534,041 A | 7/1996 | Havens et al. |
| 5,543,504 A | 8/1996 | Jinkerson |
| 5,617,154 A | 4/1997 | Hoffman |
| 5,662,707 A | 9/1997 | Jinkerson |
| 5,694,240 A | 12/1997 | Sternbergh |
| 5,702,819 A | 12/1997 | Gupta et al. |
| 5,729,379 A | 3/1998 | Allemand et al. |
| 6,021,001 A | 2/2000 | Turner |
| 6,102,539 A | 8/2000 | Tucker |
| 6,145,984 A | 11/2000 | Farwig |
| 6,158,862 A | 12/2000 | Patel et al. |
| 6,220,703 B1 | 4/2001 | Evans et al. |
| 6,231,183 B1 | 5/2001 | Dillon |
| 6,277,940 B1 | 8/2001 | Niwa et al. |
| 6,305,801 B1 | 10/2001 | Kerns et al. |
| 6,306,316 B1 | 10/2001 | Mann et al. |
| 6,310,215 B1 | 10/2001 | Iwamoto |
| 6,326,448 B1 | 12/2001 | Ojio et al. |
| 6,334,680 B1 | 1/2002 | Larson |
| 6,373,615 B1 | 4/2002 | Mann et al. |
| 6,411,450 B1 | 6/2002 | Gatewood et al. |
| 6,444,146 B2 | 9/2002 | Yoshimura et al. |
| 6,554,424 B1 * | 4/2003 | Miller et al. | 351/160 R |
| 6,604,824 B2 | 8/2003 | Larson |
| 6,641,261 B2 | 11/2003 | Wang et al. |
| 6,793,339 B1 * | 9/2004 | Yip et al. | 351/163 |
| 6,851,074 B2 | 2/2005 | Milojicic et al. |
| 6,863,848 B2 | 3/2005 | Engardio et al. |
| 6,918,931 B2 | 7/2005 | Lai et al. |
| 6,926,405 B2 | 8/2005 | Ambler et al. |
| 6,955,430 B2 | 10/2005 | Pratt |
| 6,960,231 B2 | 11/2005 | Tran |
| 6,972,034 B2 | 12/2005 | Tran et al. |
| 6,984,038 B2 | 1/2006 | Ishak |
| 6,984,734 B2 | 1/2006 | Sessler et al. |
| 6,986,579 B2 | 1/2006 | Blum et al. |
| 7,029,118 B2 | 4/2006 | Ishak |
| 7,029,758 B2 | 4/2006 | Gallas et al. |
| 7,033,391 B2 | 4/2006 | Lai et al. |
| 7,066,596 B2 | 6/2006 | Ishak |
| 7,098,283 B2 | 8/2006 | Lai |
| 7,241,312 B2 | 7/2007 | Lai et al. |
| 7,255,435 B2 | 8/2007 | Pratt |
| 7,271,298 B2 | 9/2007 | Xu et al. |
| 7,275,822 B2 | 10/2007 | Gupta et al. |
| 7,276,544 B2 | 10/2007 | Lai et al. |
| 7,278,737 B2 | 10/2007 | Mainster et al. |
| 7,279,538 B2 | 10/2007 | Lai et al. |
| 7,304,117 B2 | 12/2007 | Lai |
| 7,524,060 B2 | 4/2009 | Sanchez Ramos |
| 7,713,452 B2 | 5/2010 | Kauffman et al. |
| 7,832,903 B2 | 11/2010 | Ramos |
| 7,914,177 B2 | 3/2011 | Ramos |
| 2002/0042653 A1 | 4/2002 | Copeland et al. |
| 2002/0159026 A1 | 10/2002 | Bernheim |
| 2003/0076474 A1 * | 4/2003 | Wang et al. | 351/44 |
| 2004/0070726 A1 | 4/2004 | Ishak |
| 2005/0043793 A1 | 2/2005 | Pratt |
| 2005/0055091 A1 | 3/2005 | Lai |
| 2005/0143812 A1 | 6/2005 | Paul et al. |
| 2005/0248752 A1 | 11/2005 | Hall |
| 2005/0254003 A1 | 11/2005 | Jani et al. |
| 2005/0273163 A1 | 12/2005 | Tran et al. |
| 2005/0283234 A1 | 12/2005 | Zhou et al. |
| 2006/0020338 A1 | 1/2006 | Lai |
| 2006/0092374 A1 | 5/2006 | Ishak |
| 2006/0099148 A1 | 5/2006 | Fisher et al. |
| 2006/0119954 A1 | 6/2006 | Casper et al. |
| 2006/0126019 A1 | 6/2006 | Liang et al. |
| 2006/0197067 A1 | 9/2006 | Xia et al. |
| 2006/0228725 A1 | 10/2006 | Salafsky |
| 2006/0235428 A1 | 10/2006 | Silvestrini |
| 2006/0241263 A1 | 10/2006 | Lai |
| 2006/0252844 A1 | 11/2006 | Mentak |
| 2007/0034833 A1 | 2/2007 | Parce et al. |
| 2007/0035240 A1 | 2/2007 | Yang et al. |
| 2007/0092831 A1 | 4/2007 | Lai |
| 2007/0159594 A9 | 7/2007 | Jani et al. |
| 2007/0188701 A1 | 8/2007 | Sanchez Ramos |
| 2007/0195262 A1 | 8/2007 | Mosse et al. |
| 2007/0216861 A1 | 9/2007 | Ishak et al. |
| 2008/0002147 A1 | 1/2008 | Haywood et al. |
| 2008/0013035 A1 | 1/2008 | Yang et al. |
| 2008/0013045 A1 | 1/2008 | Mainster et al. |
| 2008/0043200 A1 | 2/2008 | Ishak et al. |
| 2008/0094566 A1 | 4/2008 | Ishak et al. |
| 2008/0241951 A1 | 10/2008 | Battulga et al. |
| 2008/0291394 A1 | 11/2008 | Ishak |
| 2008/0297931 A1 | 12/2008 | Ramos |
| 2009/0247483 A1 | 10/2009 | Mitchell et al. |
| 2009/0268157 A1 | 10/2009 | Krieg-Kowald et al. |
| 2010/0004330 A1 | 1/2010 | Huant et al. |
| 2010/0007847 A1 | 1/2010 | Cano et al. |
| 2010/0053550 A1 | 3/2010 | Giraudet |
| 2010/0060850 A1 | 3/2010 | Giraudet |
| 2010/0066974 A1 | 3/2010 | Croft et al. |
| 2010/0085534 A1 | 4/2010 | Mainster et al. |
| 2010/0091240 A1 | 4/2010 | Drobe et al. |

FOREIGN PATENT DOCUMENTS

| | | |
|---|---|---|
| WO | WO 88/02871 | 4/1988 |
| WO | WO 2008/059177 | 5/2008 |
| WO | WO 2009/053502 | 4/2009 |

OTHER PUBLICATIONS

Nolan, J.M. et al. 2009. Augmentation of Macular Pigment following Implantation of Blue Light-Filtering Intraocular Lenses at the Time of Cataract Surgery. Invest Ophthalmol Vis. Sci. 50(10):4777-85.

Ueda, T. et al. 2009. Eye damage control by reduced blue illumination, Exp. Eye. Res. 89(6):863-8.

Wiiiard, et al. 1981. Instrumental Methods of Analysis, 6th Ed. pp. 67-68.

International Search Report and Written Opinion, mailed Jul. 25, 2008, issued in related International Patent Application No. PCT/US08/55017, filed Feb. 26, 2008.

U.S. Appl. No. 11/933,069, Ishak, et al.

Infeld, K. "Sunlight Poses Universal Cataract Risk" Johns Hopkins Study (1998) available at http://www.eurekalert.org/releases/jhu-sunposcat.html, last visited Feb. 1, 2008.

Johnson, W. and Crane, R. "Introduction to Rugate Filter Technology" SPIE vol. 2046, pp. 88-108 (Nov. 1993).

Mainster, M.A. and Sparrow J.R. "How Much Blue Light Should an IOL Transmit?" British Journal of Ophthalmology, 2003, v. 87, pp. 1523-1529.

Wyszecki and Stiles. *Color Science: Concepts and Methods, Quantitative Data and Formulae.* Wiley: New York 1982, pp. 100-107.

Sparrow, J.R. et al. "Blue light-absorbing intraocular lens and retinal pigment epithelium protection in vitro" J. Cataract Refract. Surg. 2004, vol. 30, pp. 873-878.

Kalloniatis, M. and Luu, C. "Psychophysics of Vision" available at http://webvision.med.utah.edu/Phychl.html, last visited Jan. 29, 2008.

M.A. Mainster, "Violet and Blue Light Blocking Intraocular Lenses: Photoprotection vs. Photoreception" Br. J. Ophthalmol, 2006, v. 90, pp. 784-792.

M.A. Mainster, "Intraocular Lenses Should Block UV Radiation and Violet but not Blue Light," Arch. Ophthal., v. 123, p. 550 (2005).

* cited by examiner

JND Shift

JND Shift

Coumarin 6

Coumarin 30

Perylene

Magnesium Tetraphenyl Porphyrin

Yellow Orange

Acridyne Acridyne

HIGH PERFORMANCE CORNEAL INLAY

CROSS-REFERENCES TO RELATED APPLICATIONS

This application claims the benefit of U.S. Provisional Applications 60/903,324 filed Feb. 26, 2007 and 60/906,205 filed Mar. 12, 2007. This application is a continuation-in-part of U.S. patent application Ser. No. 11/933,069 filed Oct. 31, 2007, which claims priority to U.S. Provisional Application 60/978,175 filed Oct. 8, 2007. U.S. patent application Ser. No. 11/933,069 is a continuation-in-part of U.S. patent application Ser. No. 11/892,460 filed Aug. 23, 2007, which claims priority to U.S. Provisional Applications 60/839,432 filed Aug. 23, 2006; 60/841,502 filed Sep. 1, 2006; and 60/861,247 filed Nov. 28, 2006. U.S. patent application Ser. No. 11/933,069 is a continuation-in-part of U.S. patent application Ser. No. 11/761,892 filed Jun. 12, 2007, which claims priority to U.S. Provisional Application 60/812,628 filed Jun. 12, 2006 and is a continuation-in-part of U.S. patent application Ser. No. 11/378,317 filed Mar. 20, 2006. All of these applications are entirely incorporated by reference.

BACKGROUND OF THE INVENTION

Electromagnetic radiation from the sun continuously bombards the Earth's atmosphere. Light is made up of electromagnetic radiation that travels in waves. The electromagnetic spectrum includes radio waves, millimeter waves, microwaves, infrared, visible light, ultra-violet (UVA and UVB), x-rays, and gamma rays. The visible light spectrum includes the longest visible light wavelength of approximately 700 nm and the shortest of approximately 400 nm (nanometers or $10^{-9}$ meters). Blue light wavelengths fall in the approximate range of 400 nm to 500 nm. For the ultra-violet bands, UVB wavelengths are from 290 nm to 320 nm, and UVA wavelengths are from 320 nm to 400 nm. Gamma and x-rays make up the higher frequencies of this spectrum and are absorbed by the atmosphere. The wavelength spectrum of ultraviolet radiation (UVR) is 100 nm to 400 nm. Most UVR wavelengths are absorbed by the atmosphere, except where there are areas of stratospheric ozone depletion. Over the last 20 years, there has been documented depletion of the ozone layer primarily due to industrial pollution. Increased exposure to UVR has broad public health implications as an increased burden of UVR ocular and skin disease is to be expected.

The ozone layer absorbs wavelengths up to 286 nm, thus shielding living beings from exposure to radiation with the highest energy. However, we are exposed to wavelengths above 286 nm, most of which falls within the human visual spectrum (400-700 nm). The human retina responds only to the visible light portion of the electromagnetic spectrum. The shorter wavelengths pose the greatest hazard because they inversely contain more energy. Blue light has been shown to be the portion of the visible spectrum that produces the most photochemical damage to animal retinal pigment epithelium (RPE) cells. Exposure to these wavelengths has been called the blue light hazard because these wavelengths are perceived as blue by the human eye.

Cataracts and macular degeneration are widely thought to result from photochemical damage to the intraocular lens and retina, respectively. Blue light exposure has also been shown to accelerate proliferation of uveal melanoma cells. The most energetic photons in the visible spectrum have wavelengths between 380 and 500 nm and are perceived as violet or blue. The wavelength dependence of phototoxicity summed over all mechanisms is often represented as an action spectrum, such as is described in Mainster and Sparrow, "How Much Blue Light Should an IOL Transmit?" Br. J. Opthalmol., 2003, v. 87, pp. 1523-29 and FIG. 6. In eyes without an intraocular lens (aphakic eyes), light with wavelengths shorter than 400 nm can cause damage. In phakic eyes, with some intraocular devices, this light is absorbed by the intraocular lens and therefore does not contribute to retinal phototoxicity; however it can cause optical degradation of the lens or cataracts.

The pupil of the eye responds to the photopic retinal illuminance, in trolands, which is the product of the incident flux with the wavelength-dependent sensitivity of the retina and the projected area of the pupil. This sensitivity is described in Wyszecki and Stiles, *Color Science: Concepts and Methods, Quantitative Data and Formulae* (Wiley: New York) 1982, esp. pages 102-107.

Current research strongly supports the premise that short wavelength visible light (blue light) having a wavelength of approximately 400 nm-500 nm could be a contributing cause of AMD (age related macular degeneration). It is believed that the highest level of blue light absorption occurs in a region around 430 nm, such as 400 nm-460 nm. Research further suggests that blue light worsens other causative factors in AMD, such as heredity, tobacco smoke, and excessive alcohol consumption.

High energy blue/violet light, e.g., light having wavelengths of about 400 nm to about 470 nm, either by itself or in combination with ultraviolet light, may contribute to oxidative changes within the human crystalline lens resulting in presbyopia. Presbyopia is the loss of the ability (or accommodative amplitude) of the human crystalline lens to focus at near point. This loss of accommodation begins at infancy and increases throughout life, but it goes unnoticed by the individual until around age 40-45 years when he or she experiences near-point blur when viewing a near-point object. Today, presbyopia affects an estimated 1.6 billion people worldwide, and this number is expected to increase as the population ages.

The human retina includes multiple layers. These layers listed in order from the first exposed to any light entering the eye to the deepest include:
1) Nerve Fiber Layer
2) Ganglion Cells
3) Inner Plexiform Layer
4) Bipolar and Horizontal Cells
5) Outer Plexiform Layer
6) Photoreceptors (Rods and Cones)
7) Retinal Pigment Epithelium (RPE)
8) Bruch's Membrane
9) Choroid When light is absorbed by the eye's photoreceptor cells, (rods and cones) the cells bleach and become unreceptive until they recover. This recovery process is a metabolic process and is called the "visual cycle." Absorption of blue light has been shown to reverse this process prematurely. This premature reversal increases the risk of oxidative damage and is believed to lead to the buildup of the pigment lipofuscin in the retina. This build up occurs in the retinal pigment epithelium (RPE) layer. It is believed that aggregates of extracellular materials called drusen are formed due to the excessive amounts of lipofuscin.

Current research indicates that over the course of one's life, beginning with that of an infant, metabolic waste byproducts accumulate within the pigment epithelium layer of the retina, due to light interactions with the retina. This metabolic waste product is characterized by certain fluorophores, one of the most prominent being lipofuscin constituent A2E. In vitro studies by Sparrow indicate that lipofuscin chromophore A2E found within the RPE is maximally excited by 430 nm light. It is theorized that a tipping point is reached when a combination of a build-up of this metabolic waste (specifically the lipofuscin fluorophore) has achieved a certain level of accumulation, the human body's physiological ability to metabolize within the retina certain of this waste has diminished as one reaches a certain age threshold, and a blue light stimulus of the proper wavelength causes drusen to be formed in the RPE layer. It is believed that the drusen then further interfere with the normal physiology/metabolic activity which allows for the proper nutrients to get to the photoreceptors thus contributing to age-related macular degeneration (AMD). AMD is the leading cause of irreversible severe visual acuity loss in the United States and Western World. The burden of AMD is expected to increase dramatically in the next 20 years because of the projected shift in population and the overall increase in the number of ageing individuals.

Drusen hinder or block the RPE layer from providing the proper nutrients to the photoreceptors, which leads to damage or even death of these cells. To further complicate this process, it appears that when lipofuscin absorbs blue light in high quantities it becomes toxic, causing further damage and/or death of the RPE cells. It is believed that the lipofuscin constituent A2E is at least partly responsible for the short-wavelength sensitivity of RPE cells. A2E has been shown to be maximally excited by blue light; the photochemical events resulting from such excitation can lead to cell death. See, for example, Janet R. Sparrow et al., "Blue light-absorbing intraocular lens and retinal pigment epithelium protection in vitro," J. Cataract Refract. Surg. 2004, vol. 30, pp. 873-78.

From a theoretical perspective, the following appears to take place:

1) Waste buildup occurs within the pigment epithelial level starting from infancy through out life.

2) Retinal metabolic activity and ability to deal with this waste typically diminish with age.

3) The macula pigment typically decreases as one ages, thus filtering out less blue light.

4) Blue light causes the lipofuscin to become toxic. The resulting toxicity damages pigment epithelial cells.

The lighting and vision care industries have standards as to human vision exposure to UVA and UVB radiation Surprisingly, no such standard is in place with regard to blue light. For example, in the common fluorescent tubes available today, the glass envelope mostly blocks ultra-violet light but blue light is transmitted with little attenuation. In some cases, the envelope is designed to have enhanced transmission in the blue region of the spectrum. Such artificial sources of light hazard may also cause eye damage. The inventors theorize that the combination of the ozone hole in the atmosphere, numerous near-point tasks such as working on a computer, various artificial lighting including specifically florescent tubes and blue diodes, television sets, and even camera flashes contribute to the proliferation of damaging wavelengths of UV and high energy blue (blue/violet) light.

Laboratory evidence by Sparrow at Columbia University has shown that if about 50% of the blue light within the wavelength range of 430±30 nm is blocked, RPE cell death caused by the blue light may be reduced by up to 80%. External eyewear such as sunglasses, spectacles, goggles, and contact lenses that block blue light in an attempt to improve eye health are disclosed, for example, in U.S. Pat. No. 6,955,430 to Pratt. Other ophthalmic devices whose object is to protect the retina from this phototoxic light include intraocular and contact lenses. These ophthalmic devices are positioned in the optical path between environmental light and the retina and generally contain or are coated with dyes that selectively absorb blue and violet light.

Other lenses are known that attempt to decrease chromatic aberration by blocking blue light. Chromatic aberration is caused by optical dispersion of ocular media including the cornea, intraocular lens, aqueous humour, and vitreous humour. This dispersion focuses blue light at a different image plane than light at longer wavelengths, leading to defocus of the full color image. Conventional blue blocking lenses are described in U.S. Pat. No. 6,158,862 to Patel et al., U.S. Pat. No. 5,662,707 to Jinkerson, U.S. Pat. No. 5,400,175 to Johansen, and U.S. Pat. No. 4,878,748 to Johansen.

Conventional methods for reducing blue light exposure of ocular media typically completely occlude light below a threshold wavelength, while also reducing light exposure at longer wavelengths. For example, the lenses described in U.S. Pat. No. 6,955,430 to Pratt transmit less than 40% of the incident light at wavelengths as long as 650 nm, as shown in FIG. 6 of Pratt '430. The blue-light blocking lens disclosed by Johansen and Diffendaffer in U.S. Pat. No. 5,400,175 similarly attenuates light by more than 60% throughout the visible spectrum, as illustrated in FIG. 3 of the '175 patent.

Balancing the range and amount of blocked blue light may be difficult, as blocking and/or inhibiting blue light affects color balance, color vision if one looks through the optical device, and the color in which the optical device is perceived. For example, shooting glasses appear bright yellow and block blue light. The shooting glasses often cause certain colors to become more apparent when one is looking into a blue sky, allowing for the shooter to see the object being targeted sooner and more accurately. While this works well for shooting glasses, it would be unacceptable for many ophthalmic applications. In particular, such ophthalmic systems may be cosmetically unappealing because of a yellow or amber tint that is produced in lenses by blue blocking. More specifically, one common technique for blue blocking involves tinting or dyeing lenses with a blue blocking tint, such as BPI Filter Vision 450 or BPI Diamond Dye 500. The tinting may be accomplished, for example, by immersing the lens in a heated tint pot containing a blue blocking dye solution for some predetermined period of time. Typically, the dye solution has a yellow or amber color and thus imparts a yellow or amber tint to the lens. To many people, the appearance of this yellow or amber tint may be undesirable cosmetically. Moreover, the tint may interfere with the normal color perception of a lens user, making it difficult, for example, to correctly perceive the color of a traffic light or sign.

Efforts have been made to compensate for the yellowing effect of conventional blue blocking filters. For example, blue blocking lenses have been treated with additional dyes, such as blue, red or green dyes, to offset the yellowing effect. The treatment causes the additional dyes to become intermixed with the original blue blocking dyes. However, while this technique may reduce yellow in a blue blocked lens, intermixing of the dyes may reduce the effectiveness of the blue blocking by allowing more of the blue light spectrum through. Moreover, these conventional techniques undesirably reduce the overall transmission of light wavelengths other than blue light wavelengths. This unwanted reduction may in turn result in reduced visual acuity for a lens user.

It has been found that conventional blue-blocking reduces visible transmission, which in turn stimulates dilation of the pupil. Dilation of the pupil increases the flux of light to the internal eye structures including the intraocular lens and retina. Since the radiant flux to these structures increases as the square of the pupil diameter, a lens that blocks half of the blue light but, with reduced visible transmission, relaxes the pupil from 2 mm to 3 mm diameter, will actually increase the dose of blue photons to the retina by 12.5%. Protection of the retina from phototoxic light depends on the amount of this light that impinges on the retina, which depends on the transmission properties of the ocular media and also on the dynamic aperture of the pupil. Previous work to date has been silent on the contribution of the pupil to prophylaxis of phototoxic blue light.

Another problem with conventional blue-blocking is that it can degrade night vision. Blue light is more important for low-light level or scotopic vision than for bright light or photopic vision, a result which is expressed quantitatively in the luminous sensitivity spectra for scotopic and photopic vision. Photochemical and oxidative reactions cause the absorption of 400 to 450 nm light by intraocular lens tissue to increase naturally with age. Although the number of rod photoreceptors on the retina that are responsible for low-light vision also decreases with age, the increased absorption by the intraocular lens is important to degrading night vision. For example, scotopic visual sensitivity is reduced by 33% in a 53 year-old intraocular lens and 75% in a 75 year-old lens. The tension between retinal protection and scotopic sensitivity is further described in Mainster and Sparrow, "How Much Light Should and IOL Transmit?" Br. J. Opthalmol., 2003, v. 87, pp. 1523-29.

Conventional approaches to blue blocking also may include cutoff or high-pass filters to reduce the transmission below a specified blue or violet wavelength to zero. For example, all light below a threshold wavelength may be blocked completely or almost completely. For example, U.S. Pub. Patent Application No. 2005/0243272 to Mainster and Mainster, "Intraocular Lenses Should Block UV Radiation and Violet but not Blue Light," Arch. Ophthal., v. 123, p. 550 (2005) describe the blocking of all light below a threshold wavelength between 400 and 450 nm. Such blocking may be undesirable, since as the edge of the long-pass filter is shifted to longer wavelengths, dilation of the pupil acts to increase the total flux. As previously described, this can degrade scotopic sensitivity and increase color distortion.

Recently there has been debate in the field of intraocular lenses (IOLs) regarding appropriate UV and blue light blocking while maintaining acceptable photopic vision, scotopic vision, color vision, and circadian rhythms.

In view of the foregoing, there is a need for an ophthalmic system that can provide one or more of the following:

1) Blue blocking with an acceptable level of blue light protection

2) Acceptable color cosmetics, i.e., it is perceived as mostly color neutral by someone observing the ophthalmic system when worn by a wearer.

3) Acceptable color perception for a user. In particular, there is a need for an ophthalmic system that will not impair the wearer's color vision and further that reflections from the back surface of the system into the eye of the wearer be at a level of not being objectionable to the wearer.

4) Acceptable level of light transmission for wavelengths other than blue light wavelengths. In particular, there is a need for an ophthalmic system that allows for selective blockage of wavelengths of blue light while at the same time transmitting in excess of 80% of visible light.

5) Acceptable photopic vision, scotopic vision, color vision, and/or circadian rhythms.

6) Improved contrast sensitivity and/or visual acuity.

This need exists as more and more data is pointing to blue light as one of the possible contributory factors in macula degeneration (the leading cause of blindness in the industrialized world) and also other retinal diseases, including cataracts (the leading cause of blindness in the non-industrialized world) and presbyopia.

BRIEF SUMMARY OF THE INVENTION

Embodiments disclosed herein relate to ophthalmic systems comprising a selective light wavelength filter.

BRIEF DESCRIPTION OF THE DRAWINGS

FIG. 49A shows a corneal inlay with micro-apertures throughout the inlay. FIG. 49B shows a corneal inlay with a central zone and a peripheral region to create a pinhole effect. FIG. 49C shows a corneal inlay with a curved and/or thickened peripheral region. FIG. 49D shows a corneal inlay having a central zone with a plurality of pixel-like index changes. FIG. 49E shows a corneal inlay having a static diffractive central zone.

DETAILED DESCRIPTION OF THE INVENTION

Figure 1A:
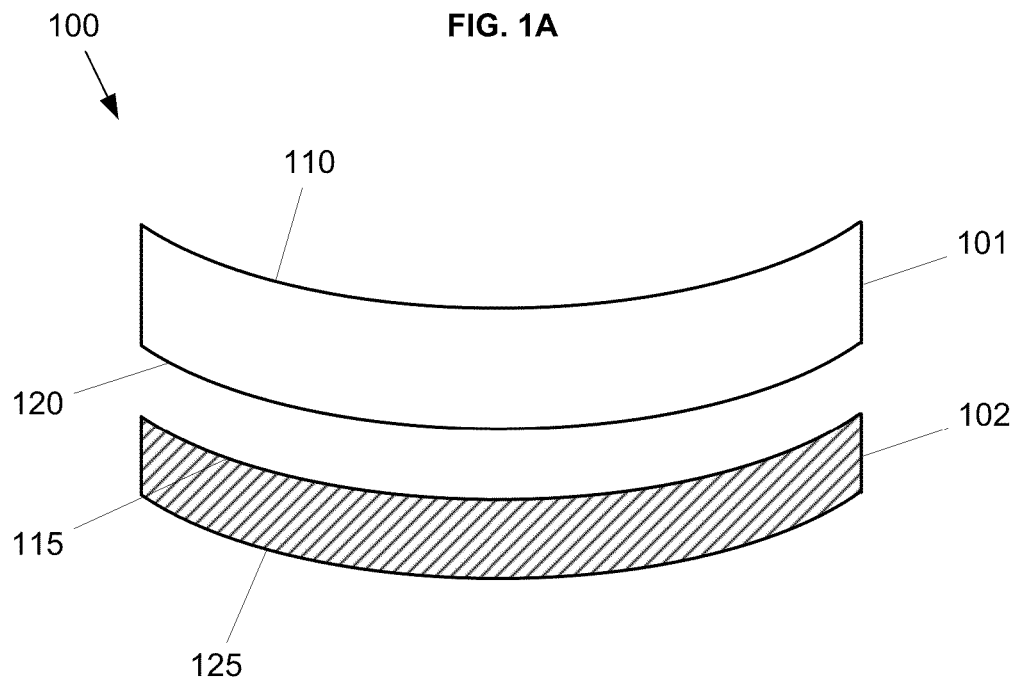
FIGS. 1A and 1B show examples of an ophthalmic system including a posterior blue blocking component and an anterior color balancing component.

Embodiments disclosed herein relate to an ophthalmic system that performs effective blue blocking while at the same time providing a cosmetically attractive product, normal or acceptable color perception for a user, and a high level of transmitted light for good visual acuity. An ophthalmic system is provided that can provide an average transmission of 80% or better transmission of visible light, inhibit selective wavelengths of blue light ("blue blocking"), allow for the wearer's proper color vision performance, and provide a mostly color neutral appearance to an observer looking at the wearer wearing such a lens or lens system. As used herein, the "average transmission" of a system refers to the average transmission at wavelengths in a range, such as the visible spectrum. A system also may be characterized by the "luminous transmission" of the system, which refers to an average in a wavelength range, that is weighted according to the sensitivity of the eye at each wavelength. Systems described herein may use various optical coatings, films, materials, and absorbing dyes to produce the desired effect.

More specifically, embodiments disclosed herein may provide effective blue blocking in combination with color balancing. "Color balancing" or "color balanced" as used herein means that the yellow or amber color, or other unwanted effect of blue blocking is reduced, offset, neutralized or otherwise compensated for so as to produce a cosmetically acceptable result, without at the same time reducing the effectiveness of the blue blocking. For example, wavelengths at or near 400 nm-460 nm may be blocked or reduced in intensity. In particular, for example, wavelengths at or near 420-440 nm may be blocked or reduced in intensity. Furthermore, transmission of unblocked wavelengths may remain at a high level, for example at least 80%. Additionally, to an external viewer, the ophthalmic system may look clear or mostly clear. For a system user, color perception may be normal or acceptable.

An "ophthalmic system" as used here includes prescription or non-prescription ophthalmic lenses used, e.g., for clear or tinted glasses (or spectacles), sunglasses, contact lenses with and without visibility and/or cosmetic tinting, intra-ocular lenses (IOLs), corneal grafts, corneal inlays, corneal on-lays, and electro-active ophthalmic devices and may be treated or processed or combined with other components to provide desired functionalities described in further detail herein. The system can be formulated so as to allow being applied directly into corneal tissue.

As used herein, an "ophthalmic material" is one commonly used to fabricate an ophthalmic system, such as a corrective lens. Exemplary ophthalmic materials include glass, plastics such as CR-39, Trivex, and polycarbonate materials, though other materials may be used and are known for various ophthalmic systems.

An ophthalmic system may include a blue blocking component posterior to a color-balancing component. Either of the blue blocking component or the color balancing component may be, or form part of, an ophthalmic component such as a lens. The posterior blue blocking component and anterior color balancing component may be distinct layers on or adjacent to or near a surface or surfaces of an ophthalmic lens. The color-balancing component may reduce or neutralize a yellow or amber tint of the posterior blue blocking component, to produce a cosmetically acceptable appearance. For example, to an external viewer, the ophthalmic system may look clear or mostly clear. For a system user, color perception may be normal or acceptable. Further, because the blue blocking and color balancing tints are not intermixed, wavelengths in the blue light spectrum may be blocked or reduced in intensity and the transmitted intensity of incident light in the ophthalmic system may be at least 80% for unblocked wavelengths.

As discussed previously, techniques for blue blocking are known. The known techniques to block blue light wavelengths include absorption, reflection, interference, or any combination thereof. As discussed earlier, according to one technique, a lens may be tinted/dyed with a blue blocking tint, such as BPI Filter Vision 450 or BPI Diamond Dye 500, in a suitable proportion or concentration. The tinting may be accomplished, for example, by immersing the lens in a heated tint pot containing a blue blocking dye solution for some predetermined period of time. According to another technique, a filter is used for blue blocking. The filter could include, for example, organic or inorganic compounds exhibiting absorption and/or reflection of and/or interference with blue light wavelengths. The filter could comprise multiple thin layers or coatings of organic and/or inorganic substances. Each layer may have properties, which, either individually or in combination with other layers, absorbs, reflects or interferes with light having blue light wavelengths. Rugate notch filters are one example of blue blocking filters. Rugate filters are single thin films of inorganic dielectrics in which the refractive index oscillates continuously between high and low values. Fabricated by the co-deposition of two materials of different refractive index (e.g. $SiO_2$ and $TiO_2$), rugate filters are known to have very well defined stop-bands for wavelength blocking, with very little attenuation outside the band. The construction parameters of the filter (oscillation period, refractive index modulation, number of refractive index oscillations) determine the performance parameters of the filter (center of the stop-band, width of the stop band, transmission within the band). Rugate filters are disclosed in more detail in, for example, U.S. Pat. Nos. 6,984,038 and 7,066,596, each of which is by reference in its entirety. Another technique for blue blocking is the use of multi-layer dielectric stacks. Multi-layer dielectric stacks are fabricated by depositing discrete layers of alternating high and low refractive index materials. Similarly to rugate filters, design parameters such as individual layer thickness, individual layer refractive index, and number of layer repetitions determine the performance parameters for multi-layer dielectric stacks.

Color balancing may comprise imparting, for example, a suitable proportion or concentration of blue tinting/dye, or a suitable combination of red and green tinting/dyes to the color-balancing component, such that when viewed by an external observer, the ophthalmic system as a whole has a cosmetically acceptable appearance. For example, the ophthalmic system as a whole may look clear or mostly clear.

FIG. 1A shows an ophthalmic system including a posterior blue blocking component 101 and an anterior color-balancing component 102. Each component has a concave posterior side or surface 110, 115 and a convex anterior side or surface 120, 125. In system 100, the posterior blue blocking component 101 may be or include an ophthalmic component, such as a single vision lens, wafer or optical pre-form. The single vision lens, wafer or optical pre-form may be tinted or dyed to perform blue blocking. The anterior color-balancing component 102 may comprise a surface cast layer, applied to the single vision lens, wafer or optical pre-form according to known techniques. For example, the surface cast layer may be affixed or bonded to the single vision lens, wafer or optical pre-form using visible or UV light, or a combination of the two.

The surface cast layer may be formed on the convex side of the single vision lens, wafer or optical pre-form. Since the single vision lens, wafer or optical pre-form has been tinted or dyed to perform blue blocking, it may have a yellow or amber color that is undesirable cosmetically. Accordingly, the surface cast layer may, for example, be tinted with a suitable proportion of blue tinting/dye, or a suitable combination of red and green tinting/dyes.

Figure 2:
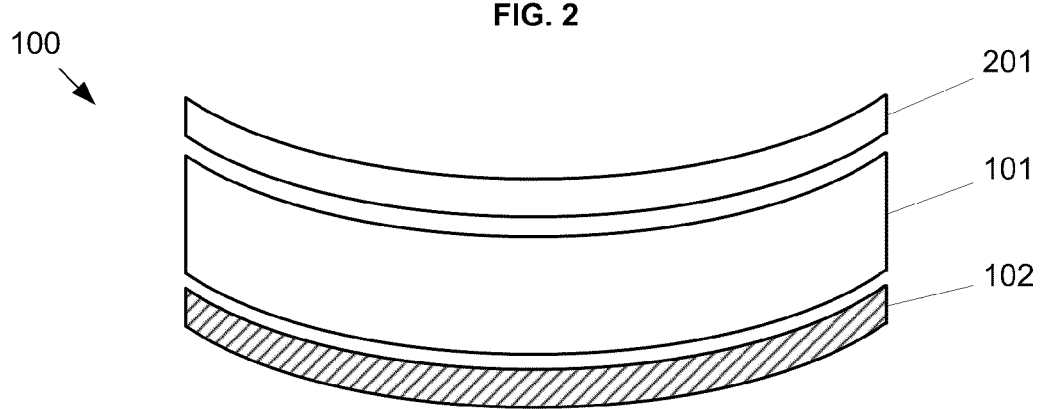
FIG. 2 shows an example of using a dye resist to form an ophthalmic system.

The surface cast layer may be treated with color balancing additives after it is applied to the single vision lens, wafer or optical pre-form that has already been processed to make it blue blocking. For example, the blue blocking single vision lens, wafer or optical pre-form with the surface cast layer on its convex surface may be immersed in a heated tint pot which has the appropriate proportions and concentrations of color balancing dyes in a solution. The surface cast layer will take up the color balancing dyes from the solution. To prevent the blue blocking single vision lens, wafer or optical pre-form from absorbing any of the color balancing dyes, its concave surface may be masked or sealed off with a dye resist, e.g. tape or wax or other coating. This is illustrated in FIG. 2, which shows an ophthalmic system 100 with a dye resist 201 on the concave surface of the single vision lens, wafer or optical pre-form 101. The edges of the single vision lens, wafer or optical pre-form may be left uncoated to allow them to become cosmetically color adjusted. This may be important for negative focal lenses having thick edges.

Figure 1B:
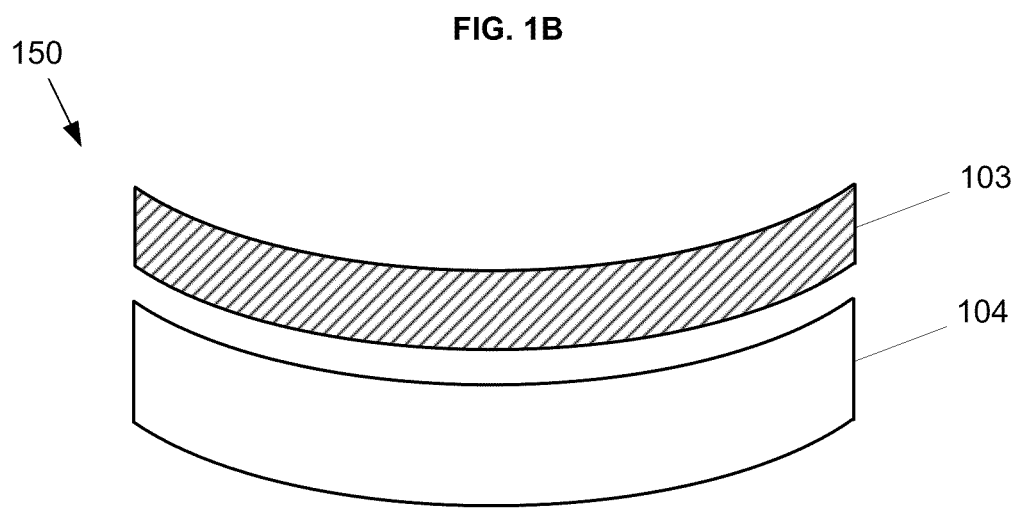

FIG. 1B shows another ophthalmic system 150 in which the anterior color-balancing component 104 may be or include an ophthalmic component, such as a single vision or multi-focal lens, wafer or optical pre-form. The posterior blue blocking component 103 may be a surface cast layer. To make this combination, the convex surface of the color balancing single vision lens, wafer or optical pre-form may be masked with a dye resist as described above, to prevent it taking up blue blocking dyes when the combination is immersed in a heated tint pot containing a blue blocking dye solution. Meanwhile, the exposed surface cast layer will take up the blue blocking dyes.

It should be understood that the surface cast layer could be used in combination with a multi-focal, rather than a single vision, lens, wafer or optical pre-form. In addition, the surface cast layer could be used to add power to a single vision lens, wafer or optical pre-form, including multi-focal power, thus converting the single vision lens, wafer or optical pre-form to a multi-focal lens, with either a lined or progressive type addition. Of course, the surface cast layer could also be designed to add little or no power to the single vision lens, wafer or optical pre-form.

Figure 3:
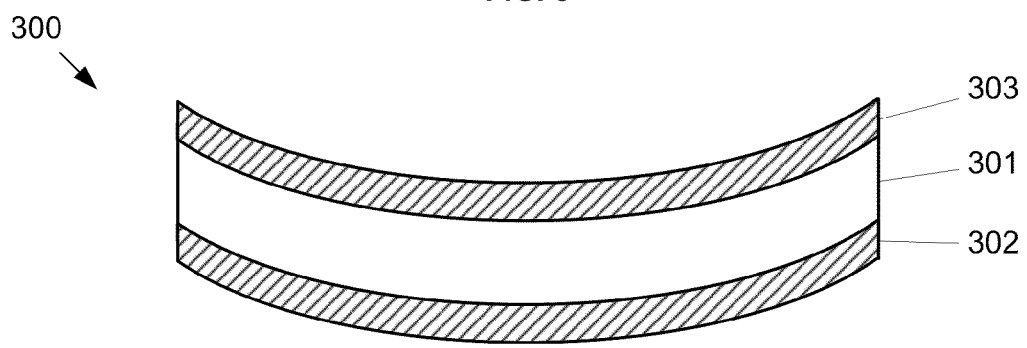
FIG. 3 illustrates an exemplary system with a blue blocking component and a color balancing component integrated into a clear or mostly clear ophthalmic lens.

FIG. 3 shows blue blocking and color balancing functionality integrated into an ophthalmic component. More specifically, in ophthalmic lens 300, a portion 303 corresponding to a depth of tint penetration into an otherwise clear or mostly clear ophthalmic component 301 at a posterior region thereof may be blue blocking. Further, a portion 302, corresponding to a depth of tint penetration into the otherwise clear or mostly clear ophthalmic component 301 at a frontal or anterior region thereof may be color balancing. The system illustrated in FIG. 3 may be produced as follows. The ophthalmic component 301 may, for example, initially be a clear or mostly clear single vision or multi-focal lens, wafer or optical pre-form. The clear or mostly clear single vision or multi-focal lens, wafer or optical pre-form may be tinted with a blue blocking tint while its front convex surface is rendered nonabsorptive, e.g., by masking or coating with a dye resist as described previously. As a result, a portion 303, beginning at the posterior concave surface of the clear or mostly clear single vision or multi-focal lens, wafer or optical pre-form 301 and extending inwardly, and having blue blocking functionality, may be created by tint penetration. Then, the anti-absorbing coating of the front convex surface may be removed. An anti-absorbing coating may then be applied to the concave surface, and the front convex surface and peripheral edges of the single vision or multi-focal lens, wafer or optical pre-form may be tinted (e.g. by immersion in a heated tint pot) for color balancing. The color balancing dyes will be absorbed by the peripheral edges and a portion 302 beginning at the front convex surface and extending inwardly, that was left untinted due to the earlier coating. The order of the foregoing process could be reversed, i.e., the concave surface could first be masked while the remaining portion was tinted for color balancing. Then, the coating could be removed and a depth or thickness at the concave region left untinted by the masking could be tinted for blue blocking.

Figure 4:
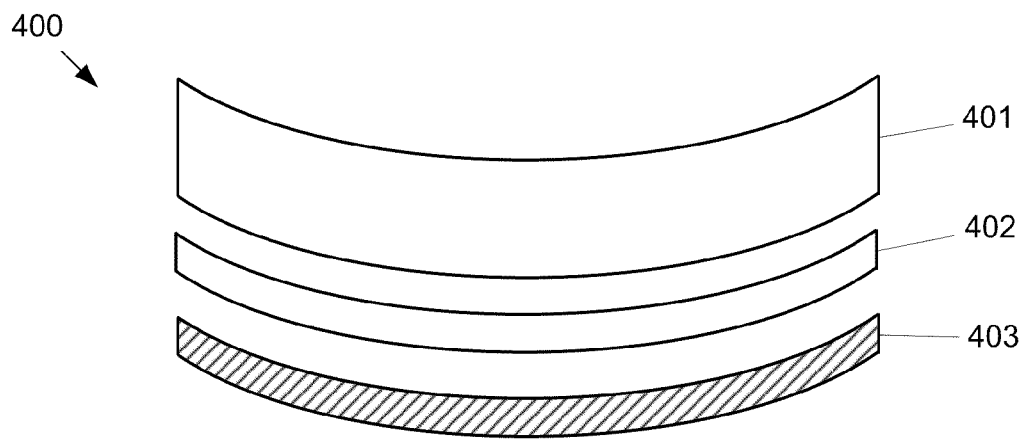
FIG. 4 illustrates an exemplary ophthalmic system formed using an in-mold coating.

Referring now to FIG. 4, an ophthalmic system 400 may be formed using an in-mold coating. More specifically, an ophthalmic component 401 such as a single vision or multi-focal lens, wafer or optical pre-form which has been dyed/tinted with a suitable blue blocking tint, dye or other additive may be color balanced via surface casting using a tinted in-mold coating 403. The in-mold coating 403, comprising a suitable level and/or mixtures of color balancing dyes, may be applied to the convex surface mold (i.e., a mold, not shown, for applying the coating 403 to the convex surface of the ophthalmic component 401). A colorless monomer 402 may be filled in and cured between the coating 403 and ophthalmic component 401. The process of curing the monomer 402 will cause the color balancing in-mold coating to transfer itself to the convex surface of the ophthalmic component 401. The result is a blue blocking ophthalmic system with a color balancing surface coating. The in-mold coating could be, for example, an anti-reflective coating or a conventional hard coating.

Figure 5:
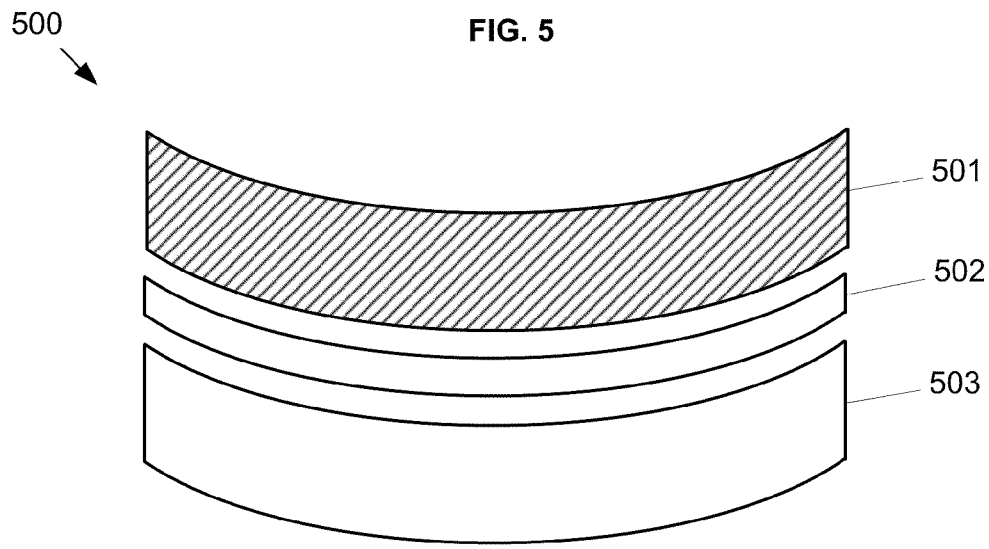
FIG. 5 illustrates the bonding of two ophthalmic components.

Referring now to FIG. 5, an ophthalmic system 500 may comprise two ophthalmic components, one blue blocking and the other color balancing. For example, a first ophthalmic component 501 could be a back single vision or concave surface multi-focal lens, wafer or optical pre-form, dyed/tinted with the appropriate blue blocking tint to achieve the desired level of blue blocking. A second ophthalmic component 503 could be a front single vision or convex surface multi-focal lens, wafer or optical pre-form, bonded or affixed to the back single vision or concave surface multi-focal lens, wafer or optical pre-form, for example using a UV or visible curable adhesive 502. The front single vision or convex surface multi-focal lens, wafer or optical pre-form could be rendered color balancing either before or after it was bonded with the back single vision or concave surface multi-focal lens, wafer or optical pre-form. If after, the front single vision or convex surface multi-focal lens, wafer or optical pre-form could be rendered color balancing, for example, by techniques described above. For example, the back single vision or concave surface multi-focal lens, wafer or optical pre-form may be masked or coated with a dye resist to prevent it taking up color balancing dyes. Then, the bonded back and front portions may be together placed in a heated tint pot containing a suitable solution of color balancing dyes, allowing the front portion to take up color balancing dyes.

Figure 6:
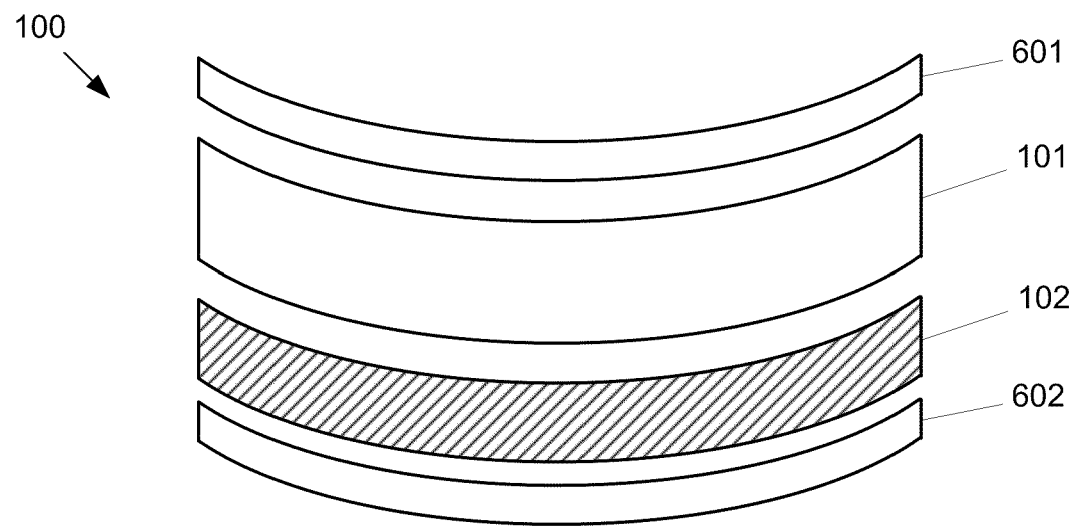
FIG. 6 illustrates exemplary ophthalmic systems using anti-reflective coatings.
Figure 6:
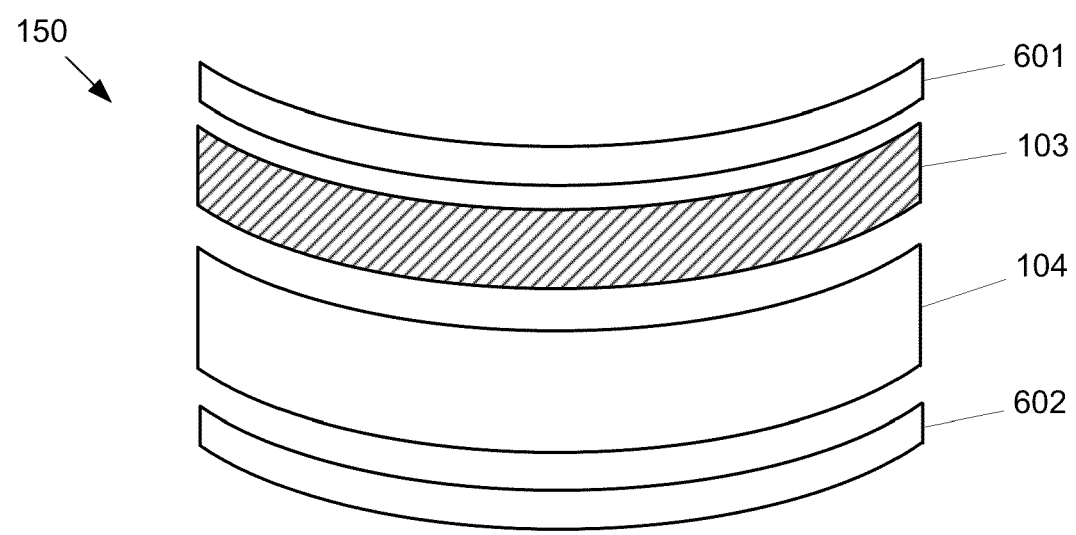

Any of the above-described embodiments systems, may be combined with one or more anti-reflective (AR) components. This is shown in FIG. 6, by way of example, for the ophthalmic lenses 100 and 150 shown in FIGS. 1A and 1B. In FIG. 6, a first AR component 601, e.g. a coating, is applied to the concave surface of posterior blue blocking element 101, and a second AR component 602 is applied to the convex surface of color balancing component 102. Similarly, a first AR component 601 is applied to the concave surface of posterior blue blocking component 103, and a second AR component 602 is applied to the convex surface of color balancing component 104.

Figure 7A:
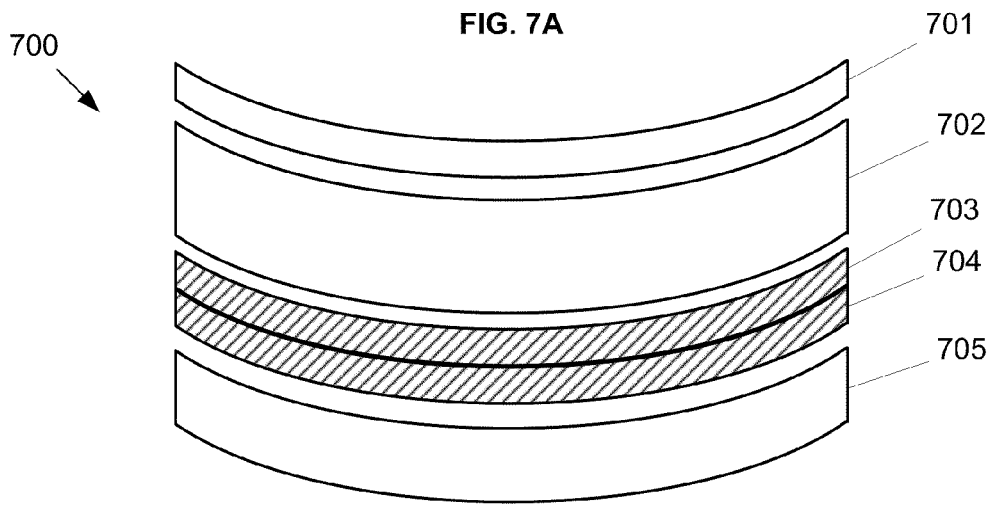
FIGS. 7A-7C illustrate various exemplary combinations of a blue blocking component, a color balancing component, and an ophthalmic component.
Figure 7B:
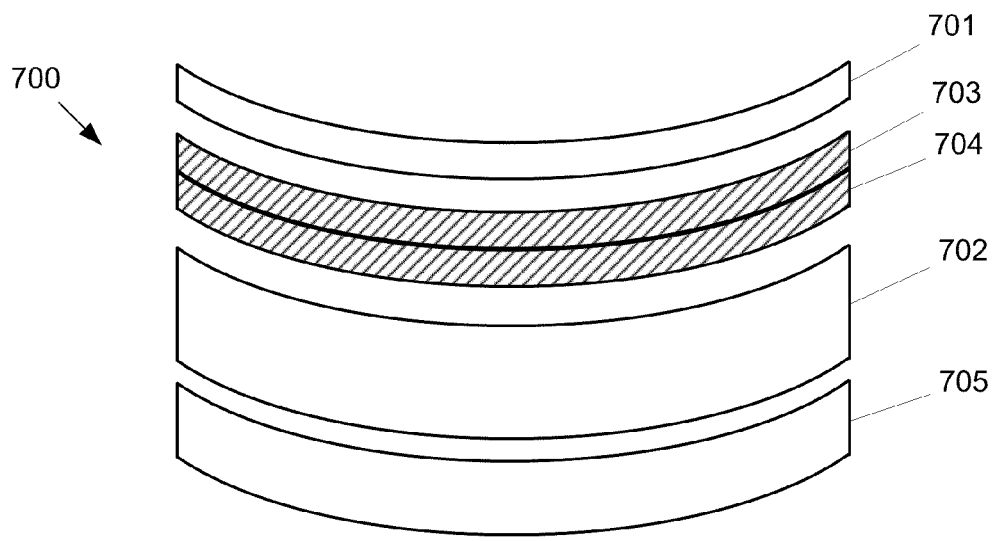
Figure 7C:
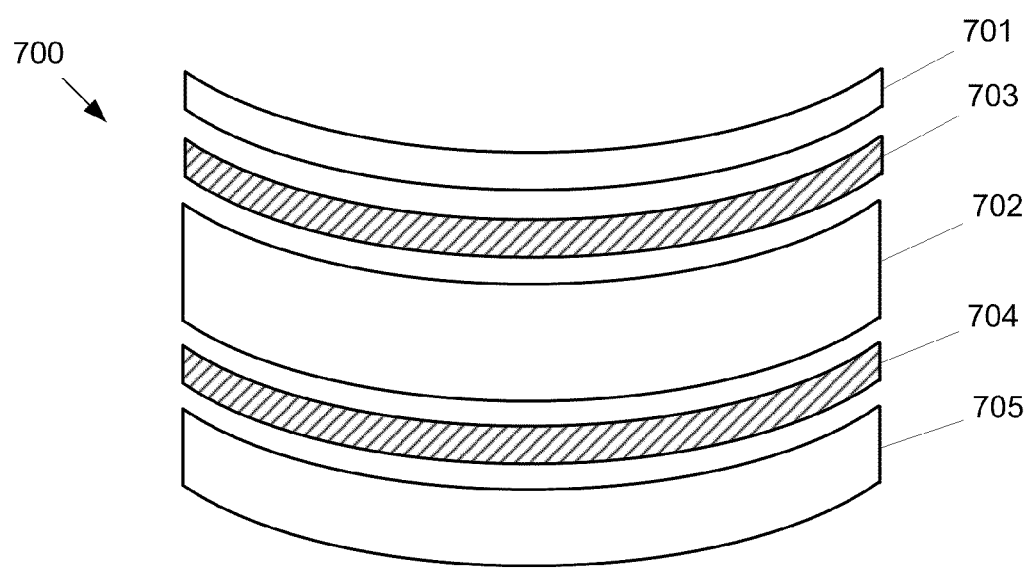

FIGS. 7A-7C show further exemplary systems including a blue blocking component and a color-balancing component. In FIG. 7A, an ophthalmic system 700 includes a blue blocking component 703 and a color balancing component 704 that are formed as adjacent, but distinct, coatings or layers on or adjacent to the anterior surface of a clear or mostly clear ophthalmic lens 702. The blue blocking component 703 is posterior to the color-balancing component 704. On or adjacent to the posterior surface of the clear or mostly clear ophthalmic lens, an AR coating or other layer 701 may be formed. Another AR coating or layer 705 may be formed on or adjacent to the anterior surface of the color-balancing layer 704.

In FIG. 7B, the blue blocking component 703 and color-balancing component 704 are arranged on or adjacent to the posterior surface of the clear or mostly clear ophthalmic lens 702. Again, the blue blocking component 703 is posterior to the color-balancing component 704. An AR component 701 may be formed on or adjacent to the posterior surface of the blue blocking component 703. Another AR component 705 may be formed on or adjacent to the anterior surface of the clear or mostly clear ophthalmic lens 702.

In FIG. 7C, the blue blocking component 703 and the color-balancing component 704 are arranged on or adjacent to the posterior and the anterior surfaces, respectively, of the clear ophthalmic lens 702. Again, the blue blocking component 703 is posterior to the color-balancing component 704. An AR component 701 may be formed on or adjacent to the posterior surface of the blue blocking component 703, and another AR component 705 may be formed on or adjacent to the anterior surface of the color-balancing component 704.

Figure 8A:
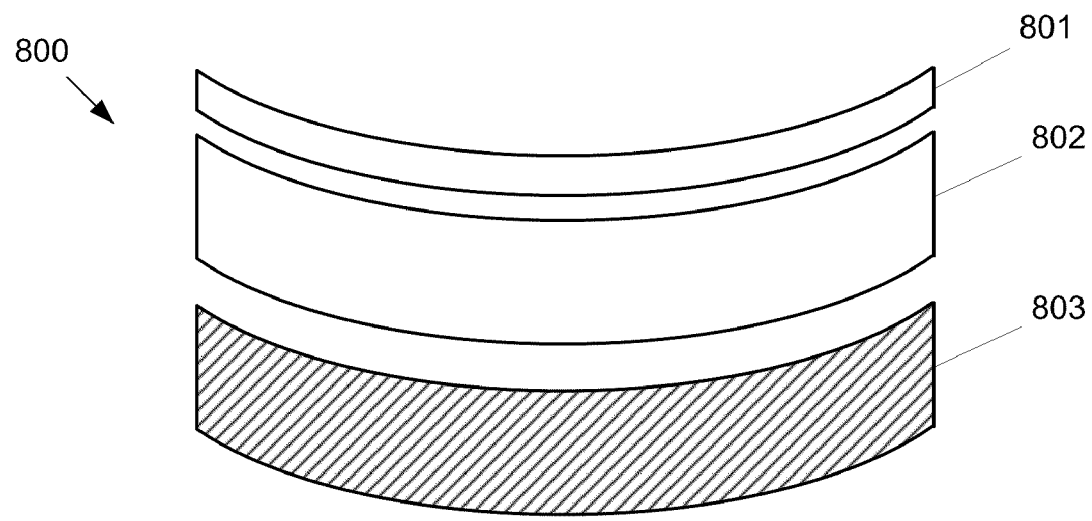
FIGS. 8A and 8B show examples of an ophthalmic system including a multi-functional blue blocking and color-balancing component.
Figure 8B:
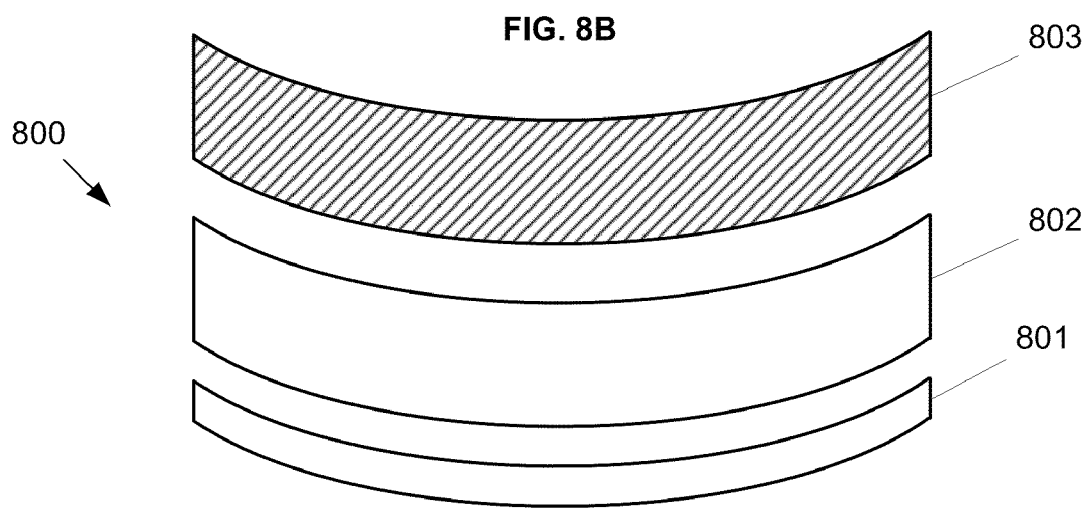

FIGS. 8A and 8B show an ophthalmic system 800 in which functionality to both block blue light wavelengths and to perform color balancing may be combined in a single component 803. For example, the combined functionality component may block blue light wavelengths and reflect some green and red wavelengths as well, thus neutralizing the blue and eliminating the appearance of a dominant color in the lens. The combined functionality component 803 may be arranged on or adjacent to either the anterior or the posterior surface of a clear ophthalmic lens 802. The ophthalmic lens 800 may further include an AR component 801 on or adjacent to either the anterior or the posterior surface of the clear ophthalmic lens 802.

To quantify the effectiveness of a color balancing component, it may be useful to observe light reflected and/or transmitted by a substrate of an ophthalmic material. The observed light may be characterized by its CIE coordinates to indicate the color of observed light; by comparing these coordinates to the CIE coordinates of the incident light, it is possible to determine how much the color of the light was shifted due to the reflection/transmission. White light is defined to have CIE coordinates of (0.33, 0.33). Thus, the closer an observed light's CIE coordinates are to (0.33, 0.33), the "more white" it will appear to an observer. To characterize the color shifting or balancing performed by a lens, (0.33, 0.33) white light may be directed at the lens, and the CIE of reflected and transmitted light observed. If the transmitted light has a CIE of about (0.33, 0.33), there will be no color shifting, and items viewed through the lens will have a natural appearance, i.e., the color will not be shifted relative to items observed without the lens. Similarly, if the reflected light has a CIE of about (0.33, 0.33), the lens will have a natural cosmetic appearance, i.e., it will not appear tinted to an observer viewing a user of the lens or ophthalmic system. Thus, it is desirable for transmitted and reflected light to have a CIE as close to (0.33, 0.33) as possible.

Figure 9:
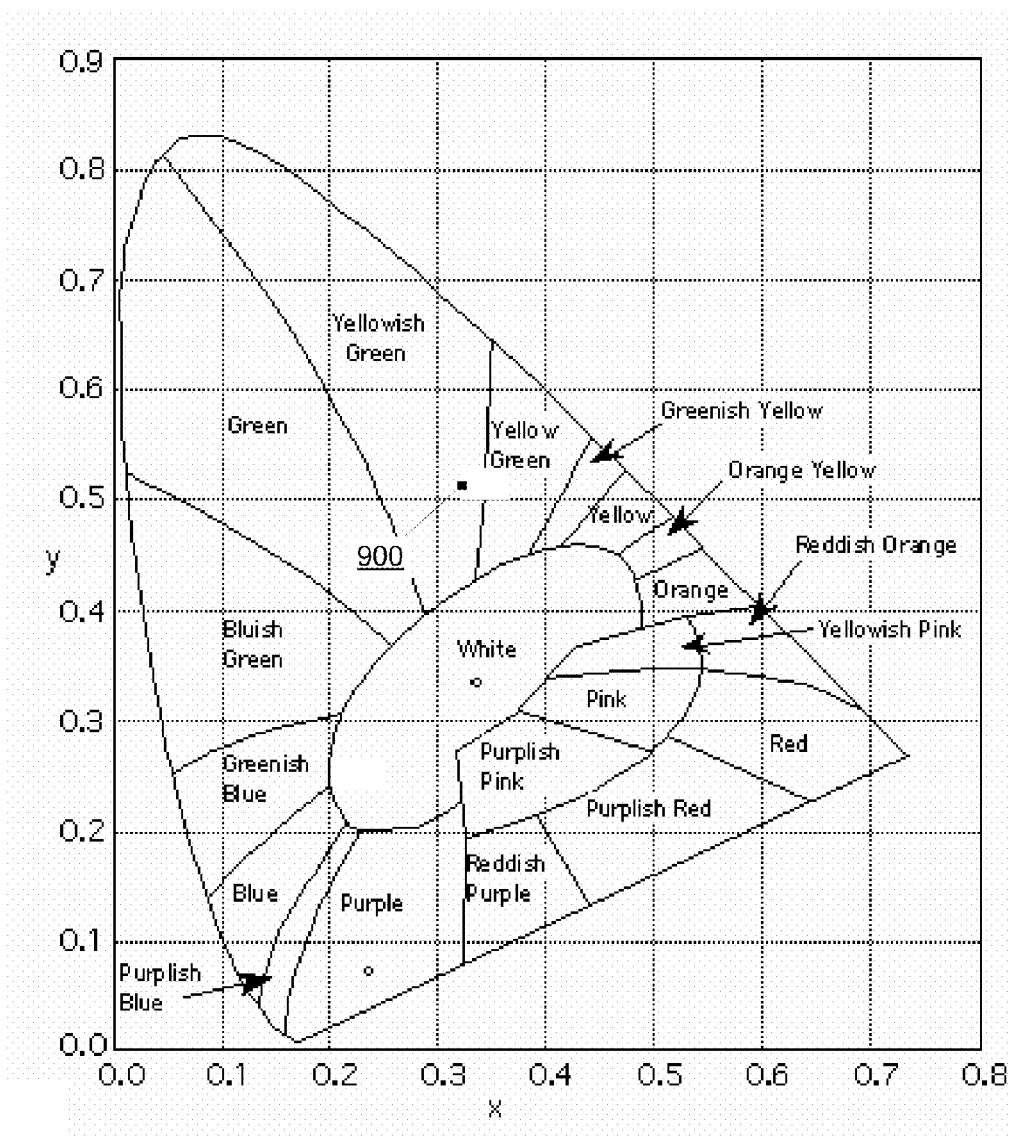
FIG. 9 shows a reference of observed colors that correspond to various CIE coordinates.

FIG. 9 shows a CIE plot indicating the observed colors corresponding to various CIE coordinates. A reference point 900 indicates the coordinates (0.33, 0.33). Although the central region of the plot typically is designated as "white," some light having CIE coordinates in this region can appear slightly tinted to a viewer. For example, light having CIE coordinates of (0.4, 0.4) will appear yellow to an observer. Thus, to achieve a color-neutral appearance in an ophthalmic system, it is desirable for (0.33, 0.33) light (i.e., white light) that is transmitted and/or reflected by the system to have CIE coordinates as close to (0.33, 0.33) as possible after the transmission/reflection. The CIE plot shown in FIG. 9 will be used herein as a reference to show the color shifts observed with various systems, though the labeled regions will be omitted for clarity.

Absorbing dyes may be included in the substrate material of an ophthalmic lens by injection molding the dye into the substrate material to produce lenses with specific light transmission and absorption properties. These dye materials can absorb at the fundamental peak wavelength of the dye or at shorter resonance wavelengths due to the presence of a Soret band typically found in porphyrin materials. Exemplary ophthalmic materials include various glasses and polymers such as CR-39®, TRIVEX®, polycarbonate, polymethylmethacrylate, silicone, and fluoropolymers, though other materials may be used and are known for various ophthalmic systems.

Figure 10:
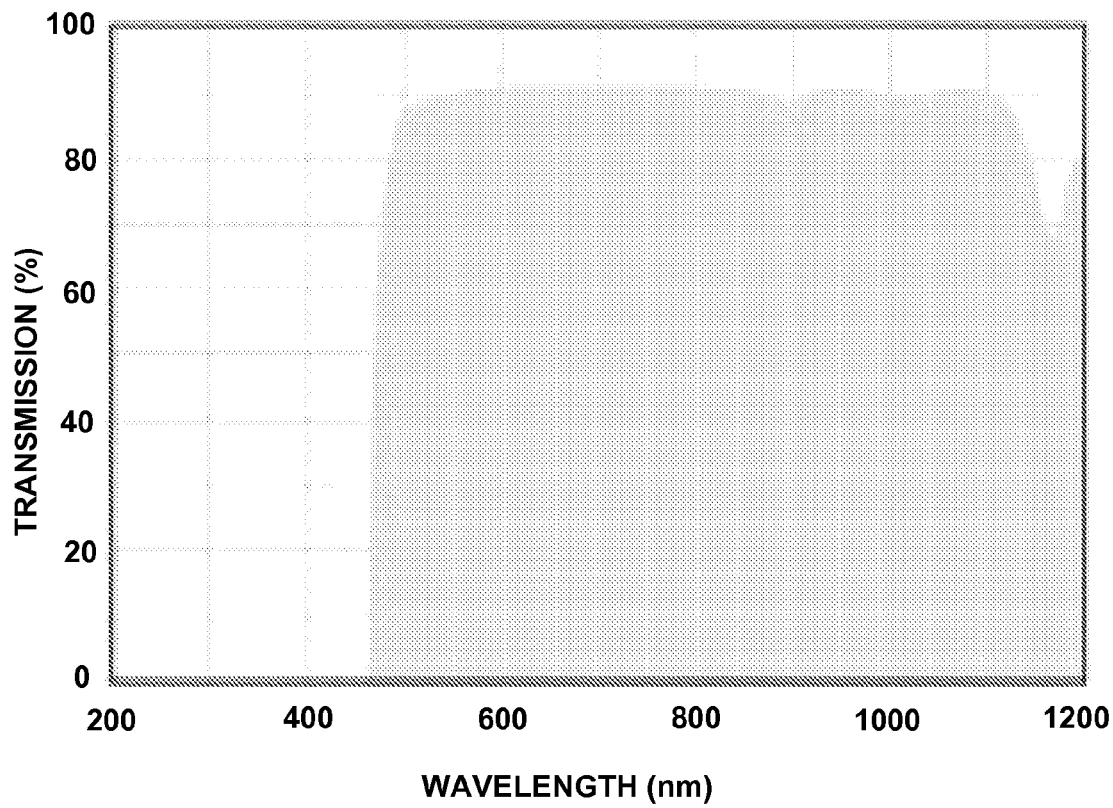
FIG. 10 shows the transmission of the GENTEX E465 absorbing dye.
Figure 11:
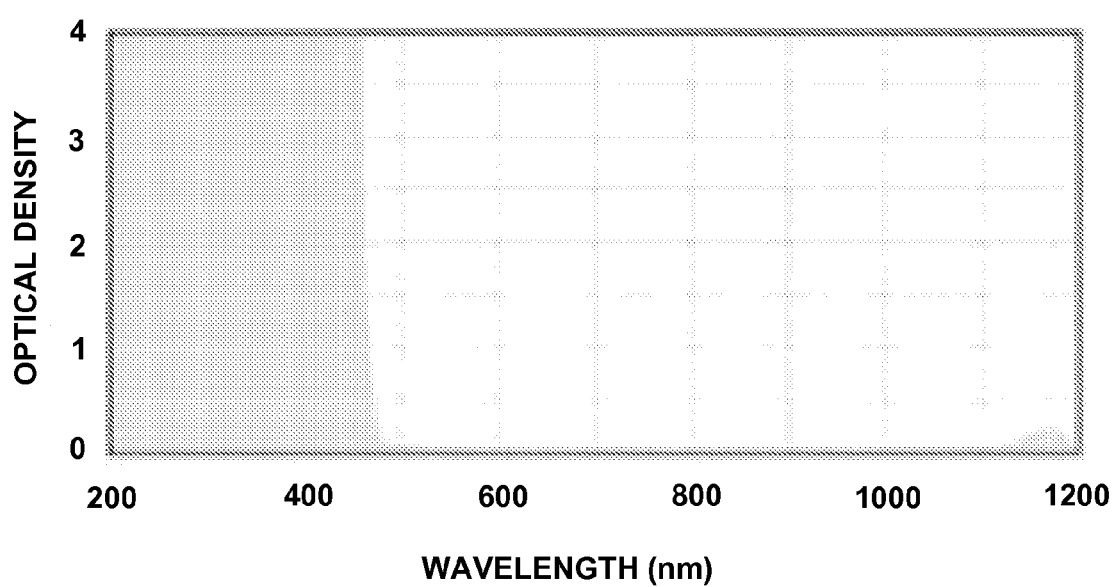
FIG. 11 shows the absorbance of the GENTEX E465 absorbing dye.

By way of example only, GENTEX dye material E465 transmittance and absorbance is shown in FIGS. 10-11. The Absorbance (A) is related to the transmittance (T) by the equation, $A=\log_{10}(1/T)$. In this case, the transmittance is between 0 and 1 ($0<T<1$). Often transmittance is express as a percentage, i.e., $0\%<T<100\%$. The E465 dye blocks those wavelengths less than 465 and is normally provided to block these wavelengths with high optical density (OD>4). Similar products are available to block other wavelengths. For example, E420 from GENTEX blocks wavelengths below 420 nm. Other exemplary dyes include porphyrins, perylene, and similar dyes that can absorb at blue wavelengths.

Figure 12:
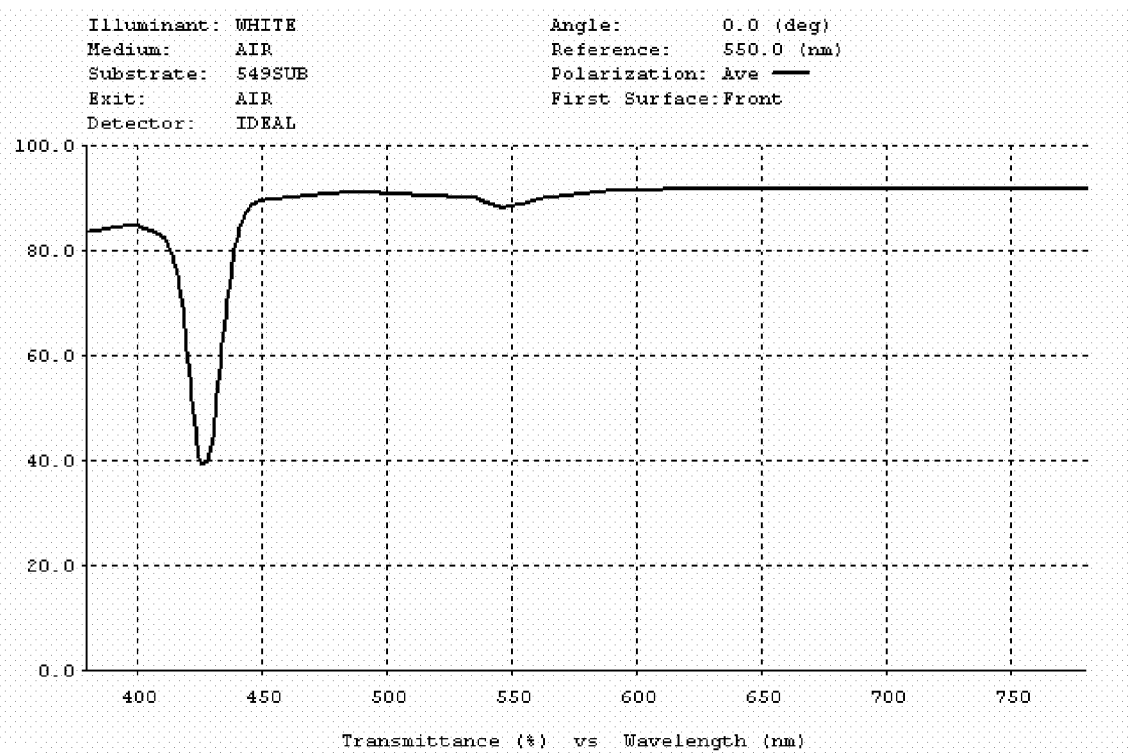
FIG. 12 shows the transmittance of a polycarbonate substrate with a dye concentration suitable for absorbing in the 430 nm range.

The absorbance at shorter wavelengths can be reduced by a reduction of the dye concentration. This and other dye materials can achieve a transmittance of 50% in the 430 nm region. FIG. 12 shows the transmittance of a polycarbonate substrate with a dye concentration suitable for absorbing in the 430 nm range, and with some absorption in the range of 420 nm-440 nm. This was achieved by reducing the concentration of the dye and including the effects of a polycarbonate substrate. The rear surface is at this point not antireflection coated.

The concentration of dye also may affect the appearance and color shift of an ophthalmic system. By reducing the concentration, systems with varying degrees of color shift may be obtained. A "color shift" as used herein refers to the amount by which the CIE coordinates of a reference light change after transmission and/or reflection of the ophthalmic system. It also may be useful to characterize a system by the color shift causes by the system due to the differences in various types of light typically perceived as white (e.g., sunlight, incandescent light, and fluorescent light). It therefore may be useful to characterize a system based on the amount by which the CIE coordinates of incident light are shifted when the light is transmitted and/or reflected by the system. For example, a system in which light with CIE coordinates of (0.33, 0.33) becomes light with a CIE of (0.30, 0.30) after transmission may be described as causing a color shift of (−0.03, −0.03), or, more generally, (±0.03, ±0.03). Thus the color shift caused by a system indicates how "natural" light and viewed items appear to a wearer of the system. As further described below, systems causing color shifts of less than (±0.05, ±0.05) to (±0.02, ±0.02) have been achieved.

A reduction in short-wavelength transmission in an ophthalmic system may be useful in reducing cell death due to photoelectric effects in the eye, such as excitation of A2E. It has been shown that reducing incident light at 430±30 nm by about 50% can reduce cell death by about 80%. See, for example, Janet R. Sparrow et al., "Blue light-absorbing intraocular lens and retinal pigment epithelium protection in vitro," J. Cataract Refract. Surg. 2004, vol. 30, pp. 873-78, the disclosure of which is incorporated by reference in its entirety. It is further believed that reducing the amount of blue light, such as light in the 430-460 nm range, by as little as 5% may similarly reduce cell death and/or degeneration, and therefore prevent or reduce the adverse effects of conditions such as atrophic age-related macular degeneration.

Although an absorbing dye may be used to block undesirable wavelengths of light, the dye may produce a color tint in the lens as a side effect. For example, many blue-blocking ophthalmic lenses have a yellow coloring that is often undesirable and/or aesthetically displeasing. To offset this coloring, a color balancing coating may be applied to one or both surfaces of a substrate including the absorbing dye therein.

Figure 13:
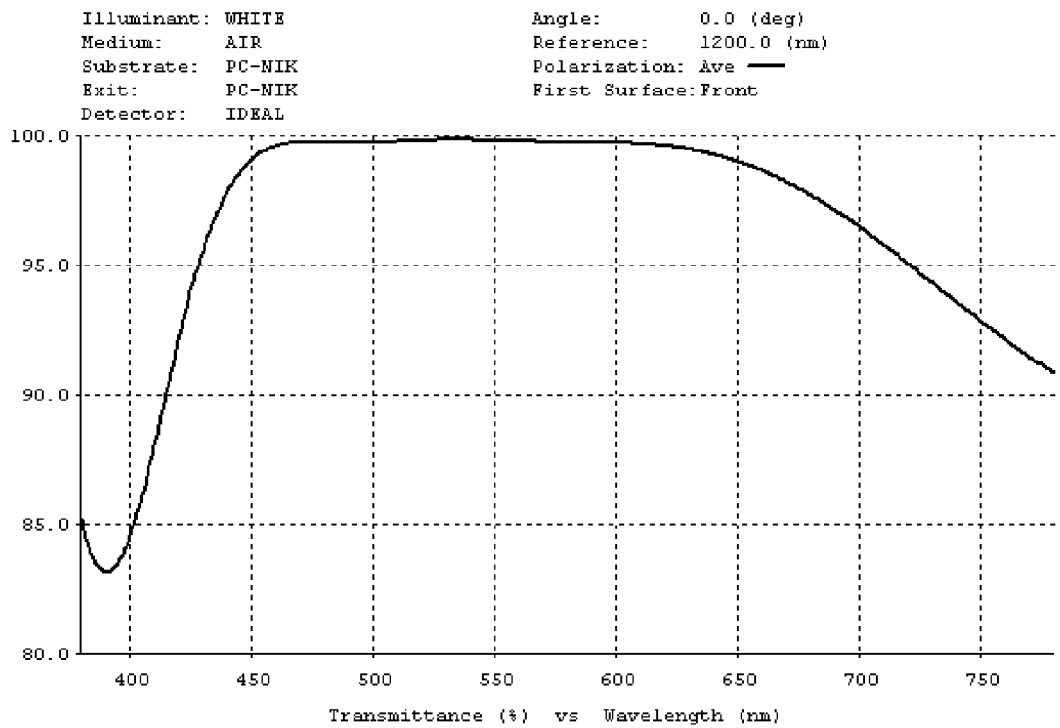
FIG. 13 shows the transmittance as a function of wavelength of a polycarbonate substrate with an antireflective coating.
Figure 14:
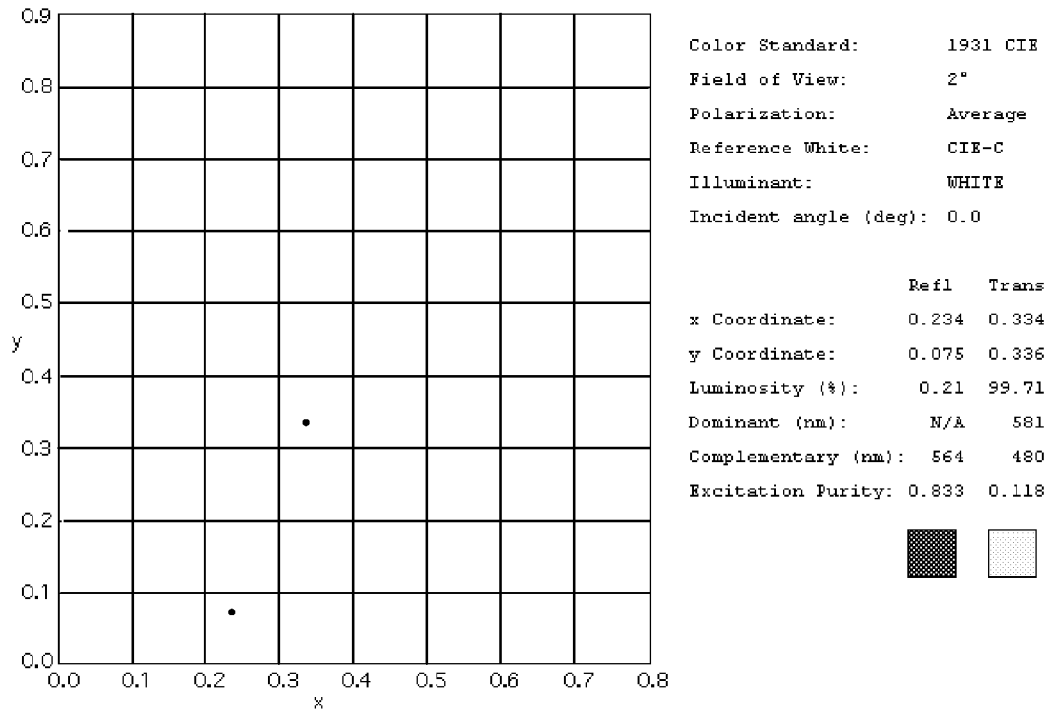
FIG. 14 shows the color plot of a polycarbonate substrate with an antireflective coating.

Antireflection (AR) coatings (which are interference filters) are well-established within the commercial ophthalmic coating industry. The coatings typically are a few layers, often less than 10, and typically are used to reduce the reflection from the polycarbonate surface to less than 1%. An example of such a coating on a polycarbonate surface is shown in FIG. 13. The color plot of this coating is shown in FIG. 14 and it is observed that the color is quite neutral. The total reflectance was observed to be 0.21%. The reflected light was observed to have CIE coordinates of (0.234, 0.075); the transmitted light had CIE coordinates of (0.334, 0.336).

Figure 15:
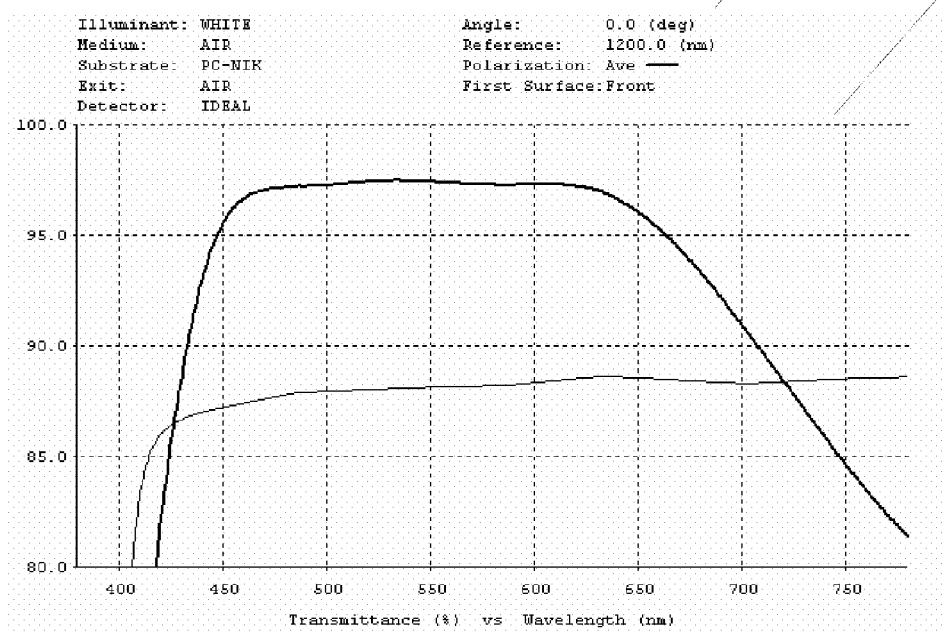
FIG. 15 shows the transmittance as a function of wavelength of an uncoated polycarbonate substrate and a polycarbonate substrate with an antireflective coating on both surfaces.

AR coatings may be applied to both surfaces of a lens or other ophthalmic device to achieve a higher transmittance. Such a configuration is shown in FIG. 15 where the darker line 1510 is the AR coated polycarbonate and the thinner line 1520 is an uncoated polycarbonate substrate. This AR coating provides a 10% increase in total transmitted light. There is some natural loss of light due to absorption in the polycarbonate substrate. The particular polycarbonate substrate used for this example has a transmittance loss of approximately 3%. In the ophthalmic industry AR coatings generally are applied to both surfaces to increase the transmittance of the lens.

In one embodiment, AR coatings or other color balancing films may be combined with an absorbing dye to allow for simultaneous absorption of blue wavelength light, typically in the 430 nm region, and increased transmittance. As previously described, elimination of the light in the 430 nm region alone typically results in a lens that has some residual color cast. To spectrally tailor the light to achieve a color neutral transmittance, at least one of the AR coatings may be modified to adjust the overall transmitted color of the light. This adjustment may be performed on the front surface of the lens to create the following lens structure:

Air (farthest from the user's eye)/Front convex lens coating/Absorbing ophthalmic lens substrate/rear concave antireflection coating/Air (closest to the user's eye).

In such a configuration, the front coating may provide spectral tailoring to offset the color cast resulting from the absorption in the substrate in addition to the antireflective function typically performed in conventional lenses. The lens therefore may provide an appropriate color balance for both transmitted and reflected light. In the case of transmitted light the color balance allows for proper color vision; in the case reflected light the color balance may provide the appropriate lens aesthetics.

In some cases, a color balancing film may be disposed between two layers of other ophthalmic material. For example, a filter, AR film, or other film may be disposed within an opthalmic material. For example, the following configuration may be used:

Air (farthest from the user's eye)/ophthalmic material/film/ophthalmic material/air (closest to user's eye).

The color balancing film also may be a coating, such as a hardcoat, applied to the outer and/or inner surface of a lens. Other configurations are possible. For example, referring to FIG. 3, an ophthalmic system may include an ophthalmic material 301 doped with a blue-absorbing dye and one or more color balancing layers 302, 303. In another configuration, an inner layer 301 may be a color balancing layer surrounded by ophthalmic material 302, 303 doped with a blue-absorbing dye. Additional layers and/or coatings, such as AR coatings, may be disposed on one or more surfaces of the system. It will be understood how similar materials and configurations may be used, for example in the systems described with respect to FIGS. 4-8B.

Thus, optical films and/or coatings such as AR coatings may be used to fine-tune the overall spectral response of a lens having an absorbing dye. Transmission variation across the visible spectrum is well known and varies as a function of the thickness and number of layers in the optical coating. One or more layers can be used to provide the needed adjustment of the spectral properties.

Figure 16:
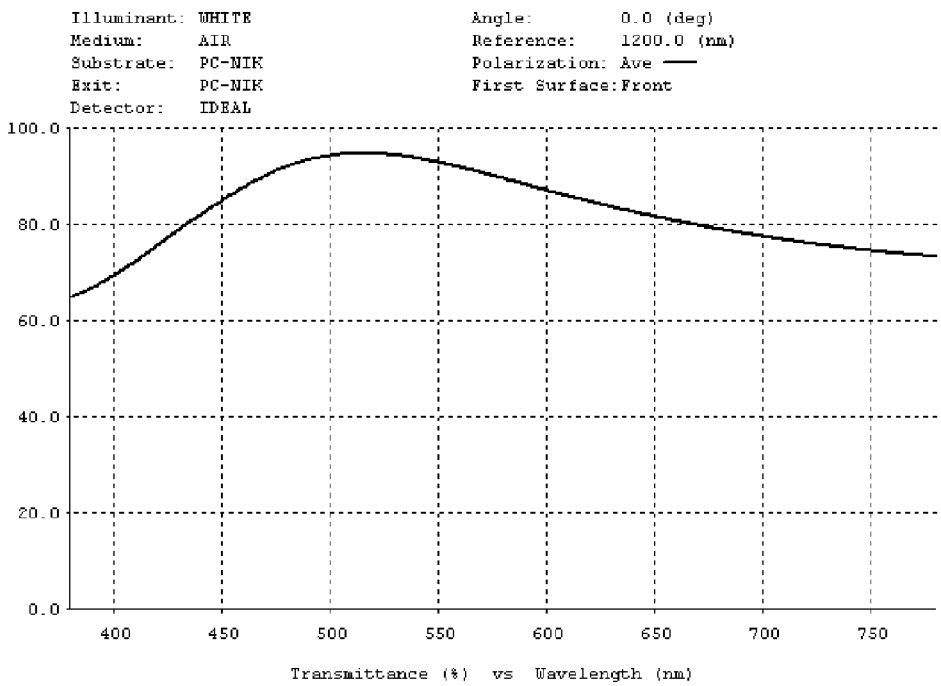
FIG. 16 shows the spectral transmittance of a 106 nm layer of TiO2 on a polycarbonate substrate.
Figure 17:
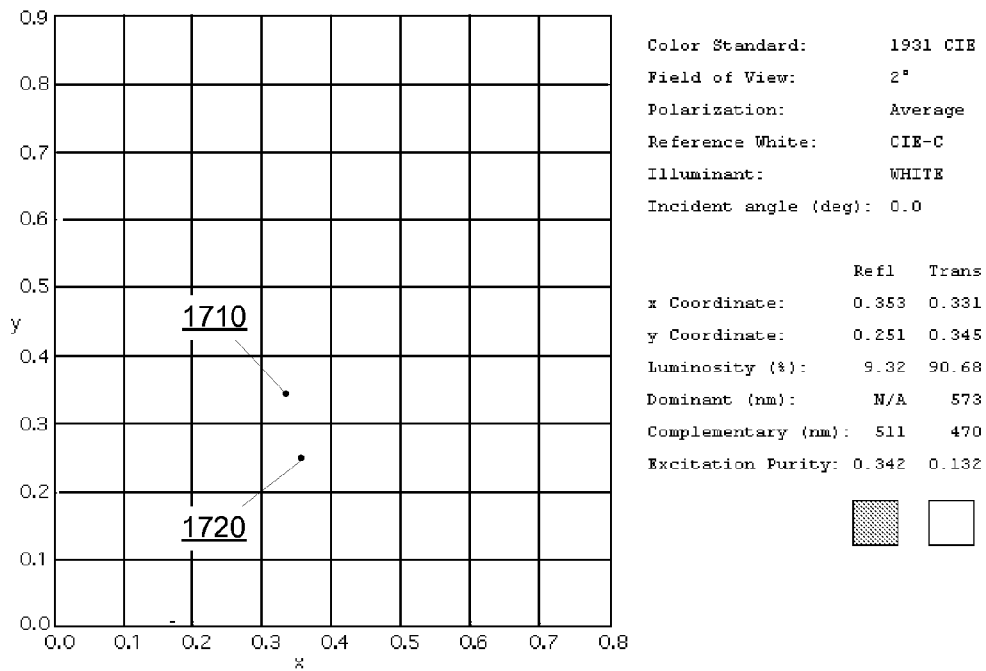
FIG. 17 shows the color plot of a 106 nm layer of TiO2 on a polycarbonate substrate.

In an exemplary system, color variation is produced by a single layer of $TiO_2$ (a common AR coating material). FIG. 16 shows the spectral transmittance of a 106 nm thick single layer of $TiO_2$. The color plot of this same layer is shown in FIG. 17. The CIE color coordinates (x, y) 1710 shown for the transmitted light are (0.331, 0.345). The reflected light had CIE coordinates of (0.353, 0.251) 1720, resulting in a purplish-pink color.

Figure 18:
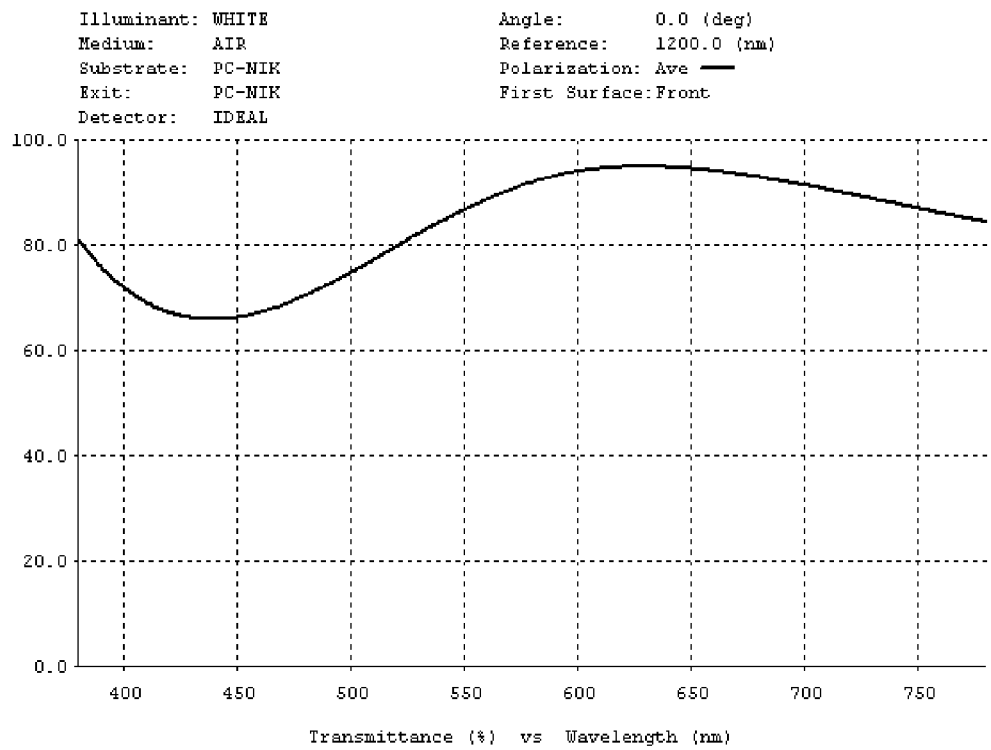
FIG. 18 shows the spectral transmittance of a 134 nm layer of TiO2 on a polycarbonate substrate.
Figure 19:
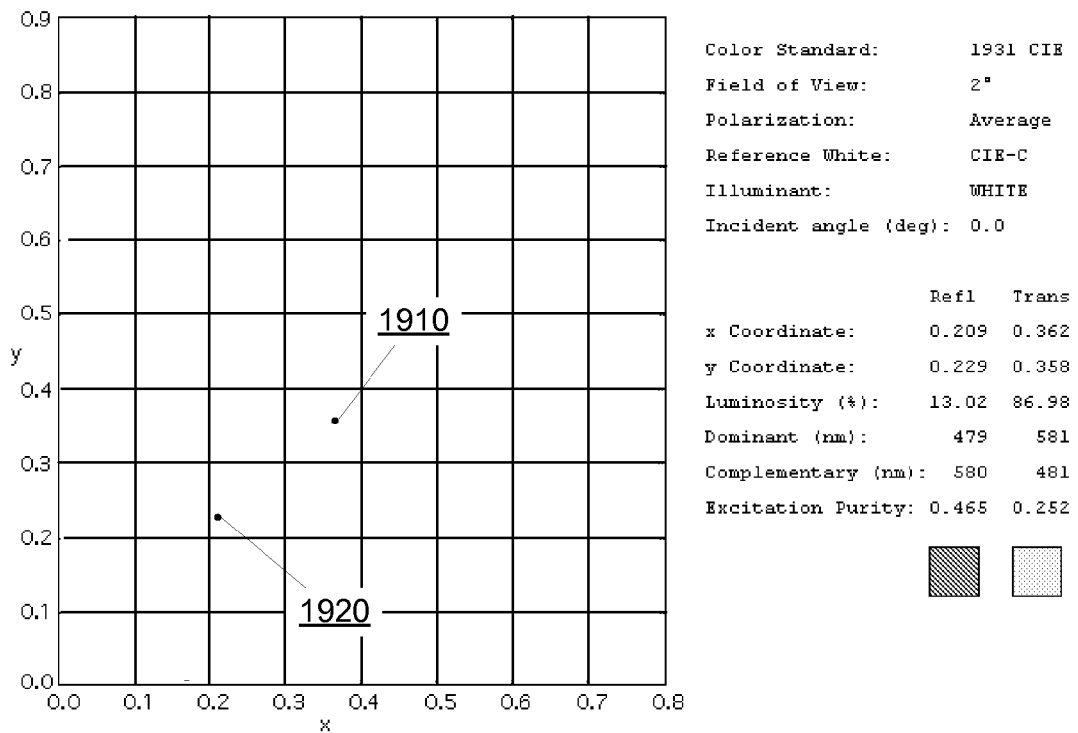
FIG. 19 shows the color plot of a 134 nm layer of TiO2 on a polycarbonate substrate.

Changing the thickness of the $TiO_2$ layer changes the color of the transmitted light as shown in the transmitted spectra and color plot for a 134 nm layer, shown in FIGS. 18 and 19 respectively. In this system, the transmitted light exhibited CIE coordinates of (0.362, 0.368) 1910, and the reflected light had CIE coordinates of (0.209, 0.229) 1920. The transmission properties of various AR coatings and the prediction or estimation thereof are known in the art. For example, the transmission effects of an AR coating formed of a known thickness of an AR material may be calculated and predicted using various computer programs. Exemplary, non-limiting programs include Essential Macleod Thin Films Software available from Thin Film Center, Inc., TFCalc available from Software Spectra, Inc., and FilmStar Optical Thin Film Software available from FTG Software Associates. Other methods may be used to predict the behavior of an AR coating or other similar coating or film.

Figure 20:
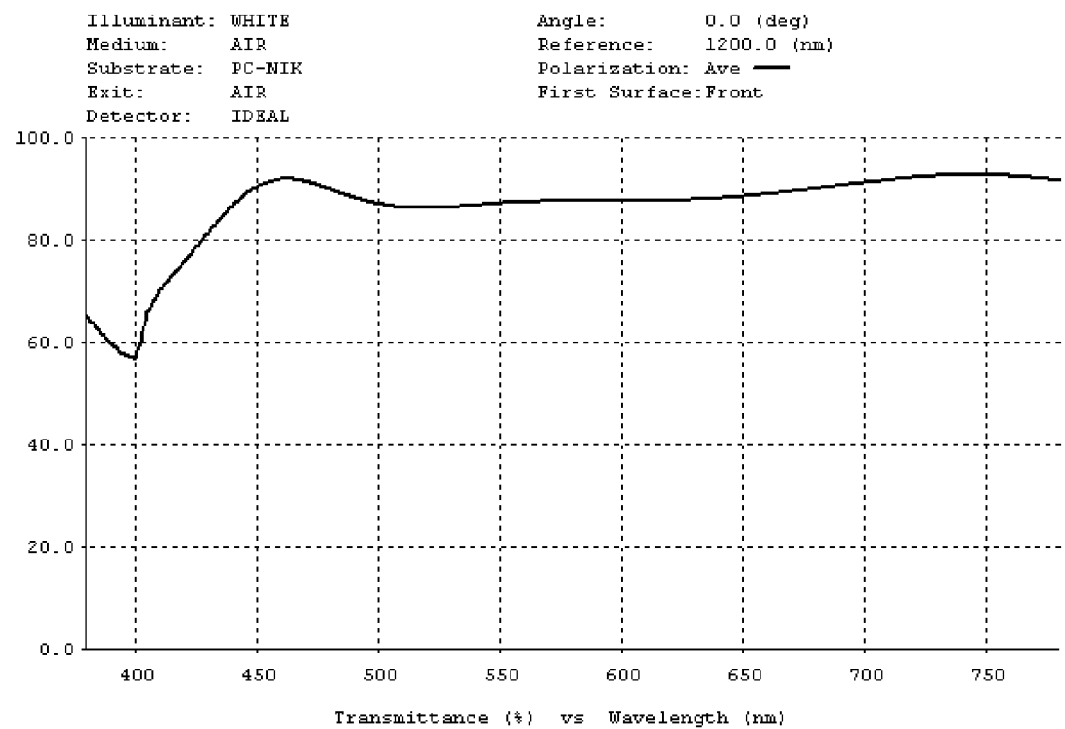
FIG. 20 shows the spectral transmittance of a modified AR coating suitable for color balancing a substrate having a blue absorbing dye.
Figure 21:
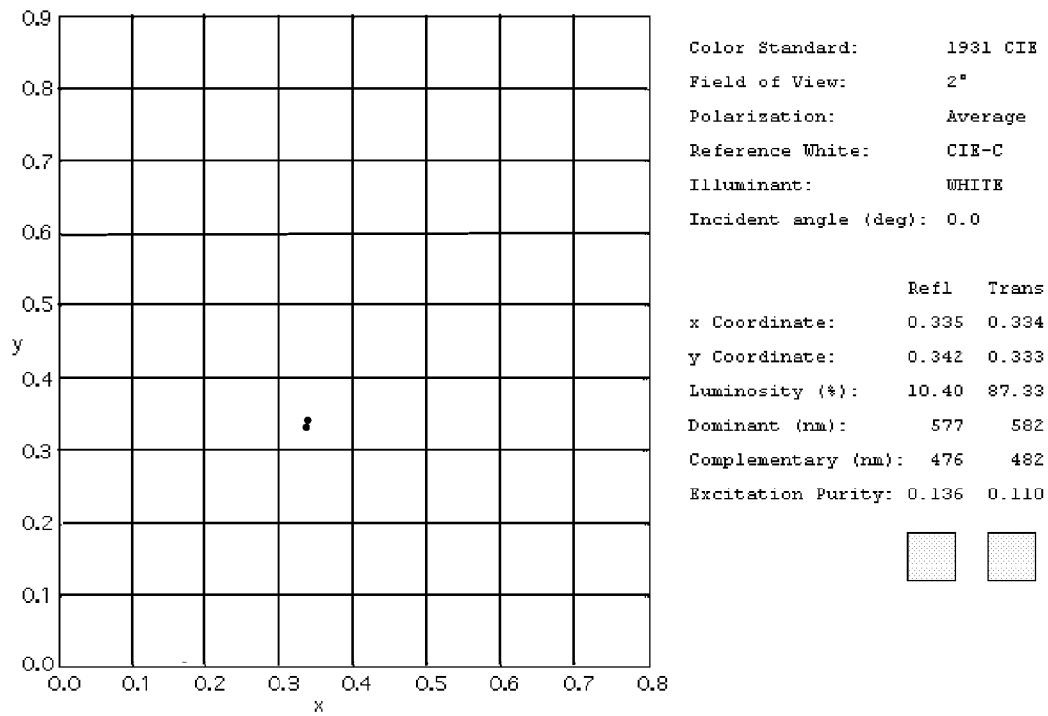
FIG. 21 shows the color plot of a modified AR coating suitable for color balancing a substrate having a blue absorbing dye.
Figure 22:
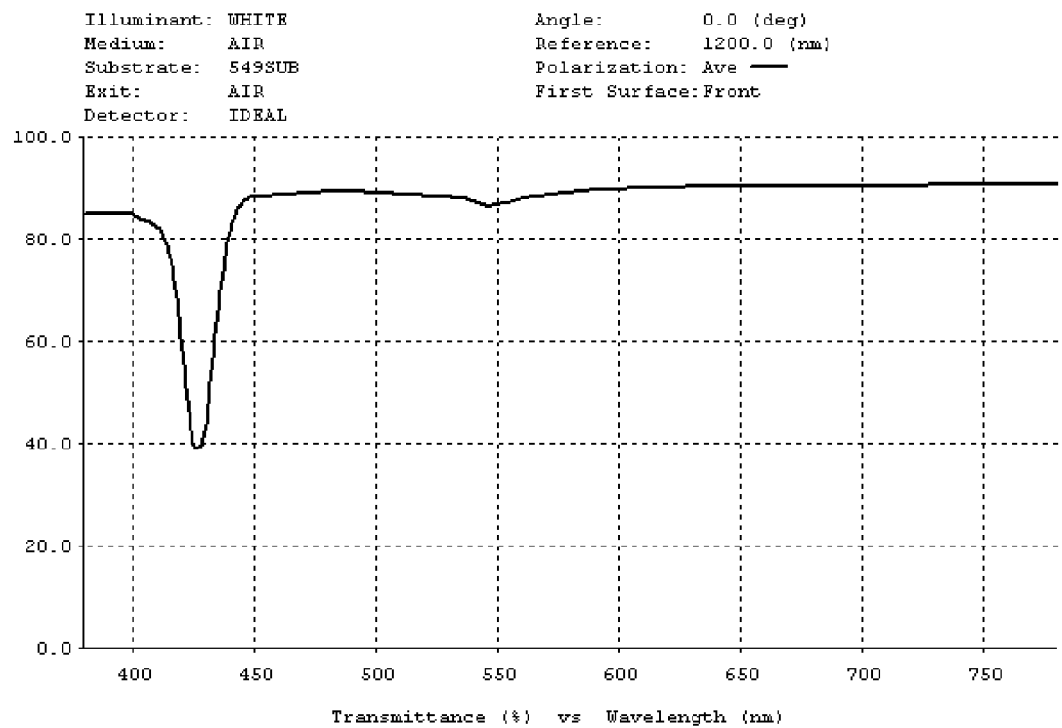
FIG. 22 shows the spectral transmittance of a substrate having a blue absorbing dye.
Figure 23:
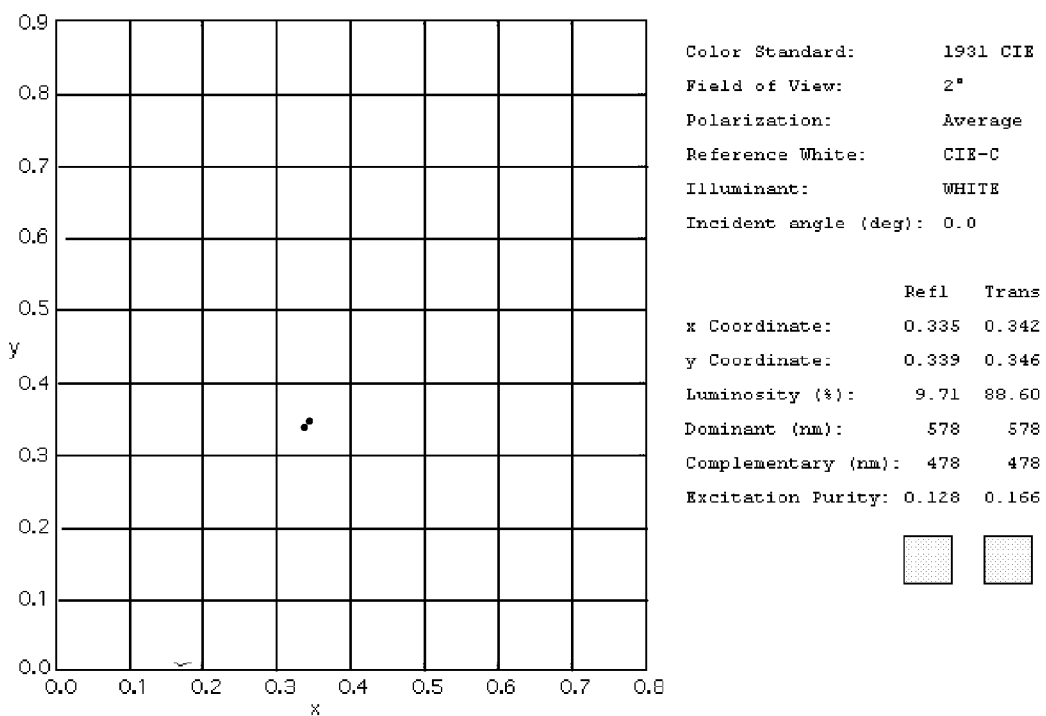
FIG. 23 shows the color plot of a substrate having a blue absorbing dye.
Figure 24:
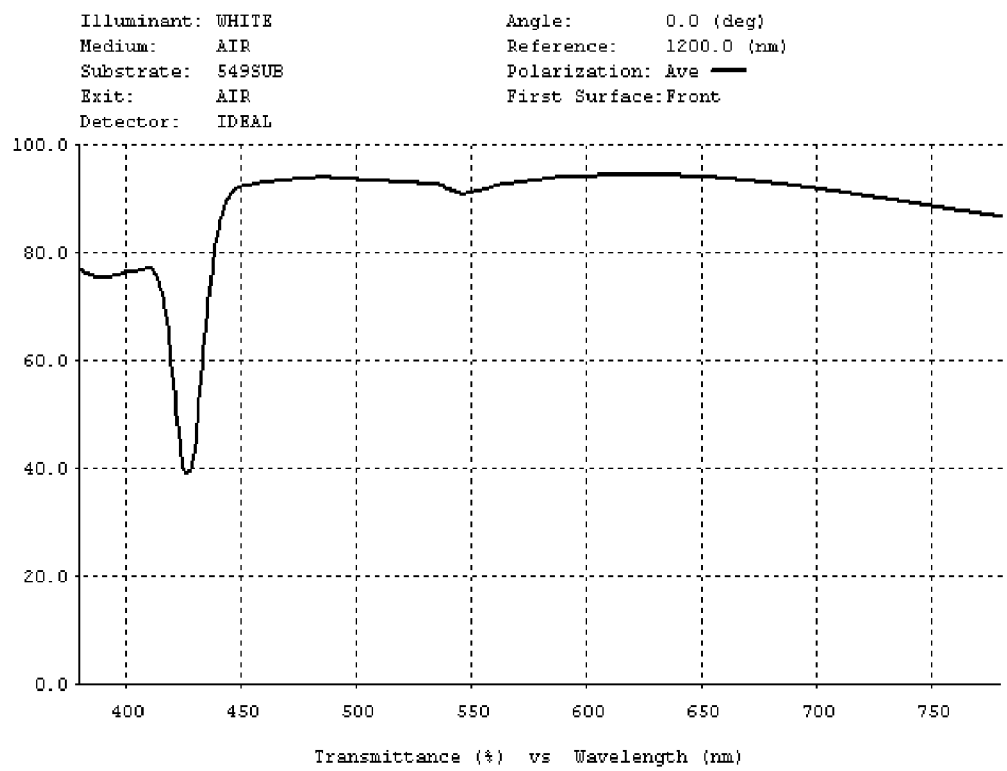
FIG. 24 shows the spectral transmittance of a substrate having a blue absorbing dye and a rear AR coating.
Figure 25:
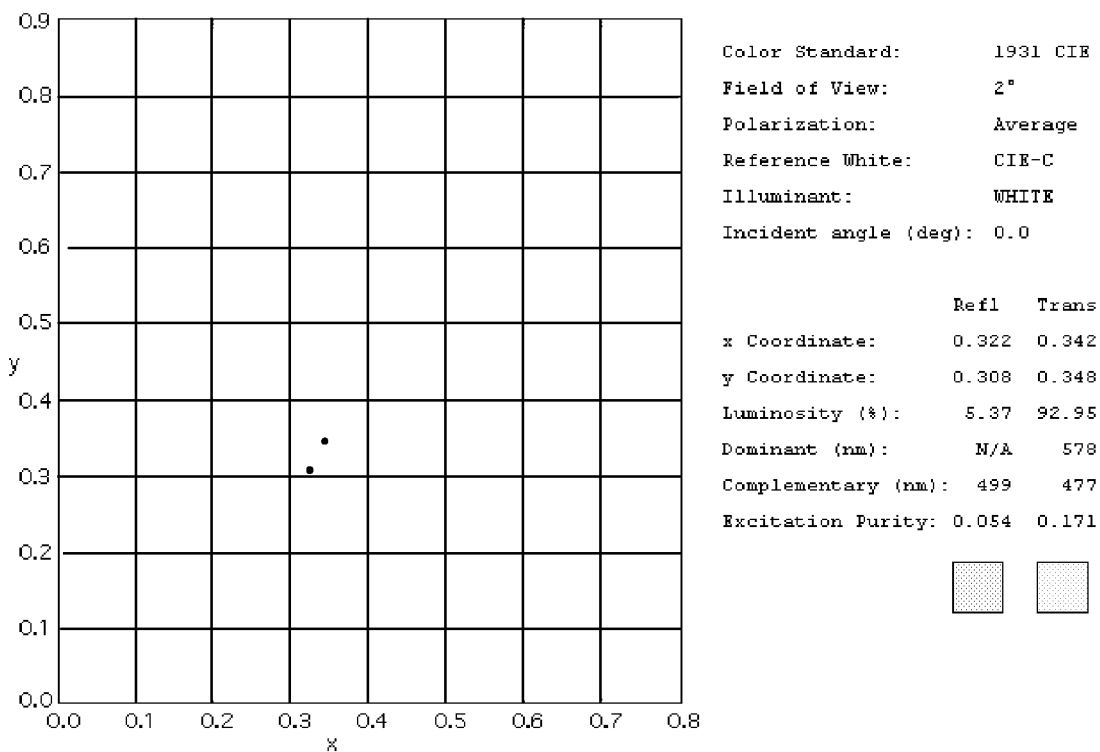
FIG. 25 shows the color plot of a substrate having a blue absorbing dye and a rear AR coating.

In one embodiment, a blue-absorbing dye may be combined with a coating or other film to provide a blue blocking, color balanced system. The coating may be an AR coating on the front surface that is modified to correct the color of the transmitted and/or reflected light. The transmittance and color plot of an exemplary AR coating are shown in FIGS. 20 and 21, respectively. FIGS. 22 and 23 show the transmittance and color plot, respectively, for a polycarbonate substrate having a blue absorbing dye without an AR coating. The dyed substrate absorbs most strongly in the 430 nm region, including some absorption in the 420-440 nm region. The dyed substrate may be combined with an appropriate AR coating as illustrated in FIGS. 20-21 to increase the overall transmittance of the system. The transmittance and color plot for a dyed substrate having a rear AR coating are shown in FIGS. 24 and 25, respectively.

Figure 26:
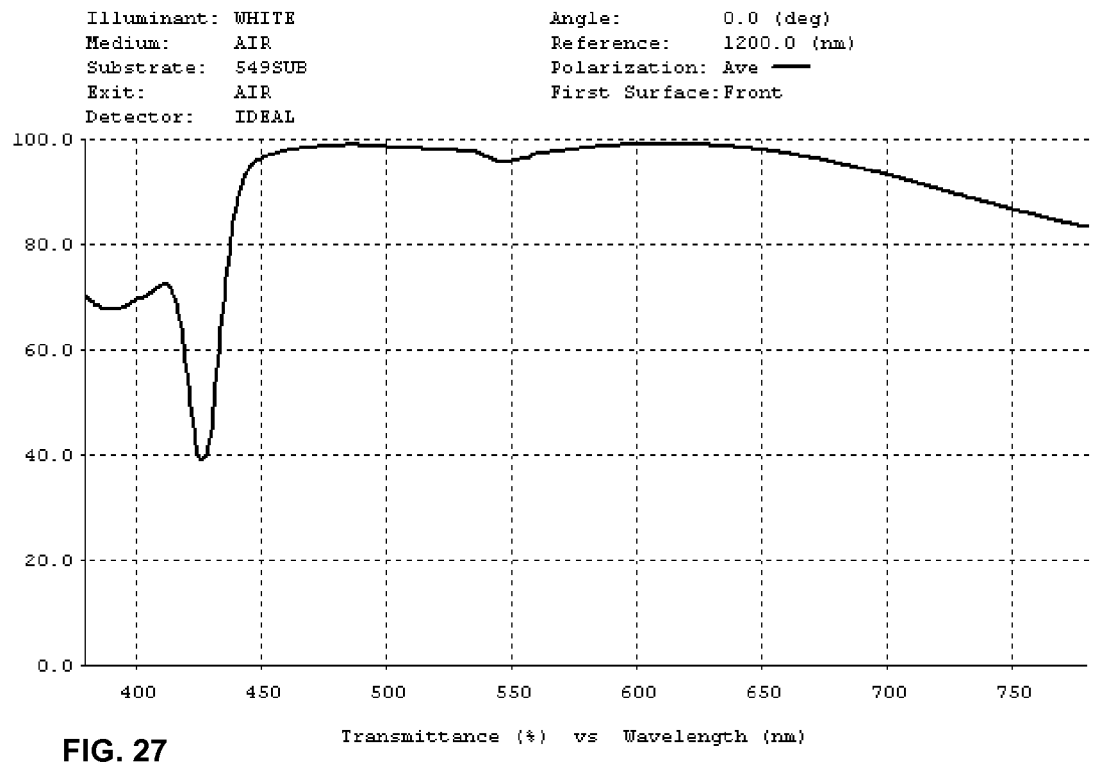
FIG. 26 shows the spectral transmittance of a substrate having a blue absorbing dye and AR coatings on the front and rear surfaces.
Figure 27:
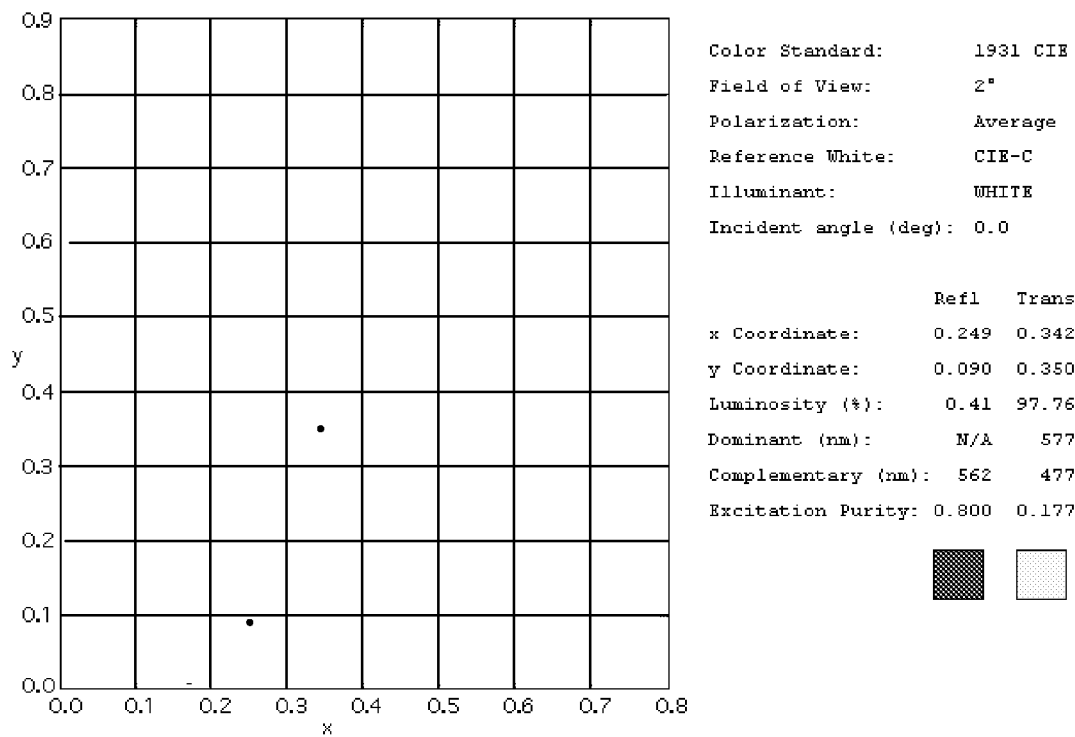
FIG. 27 shows the color plot of a substrate having a blue absorbing dye and AR coatings on the front and rear surfaces.
Figure 28:
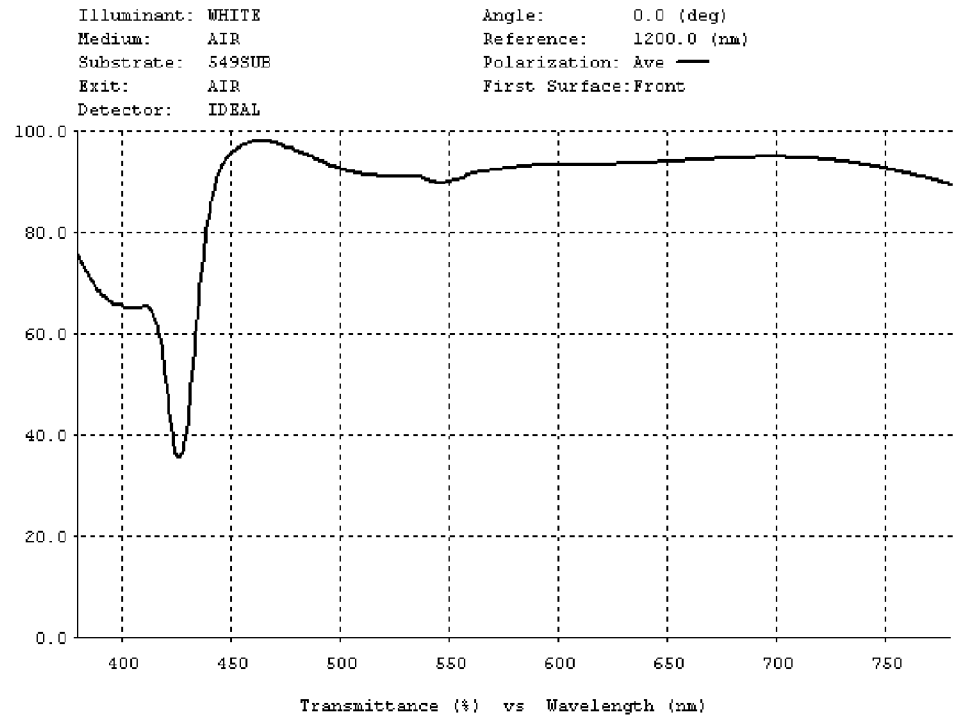
FIG. 28 shows the spectral transmittance of a substrate having a blue absorbing dye and a color balancing AR coating.
Figure 29:
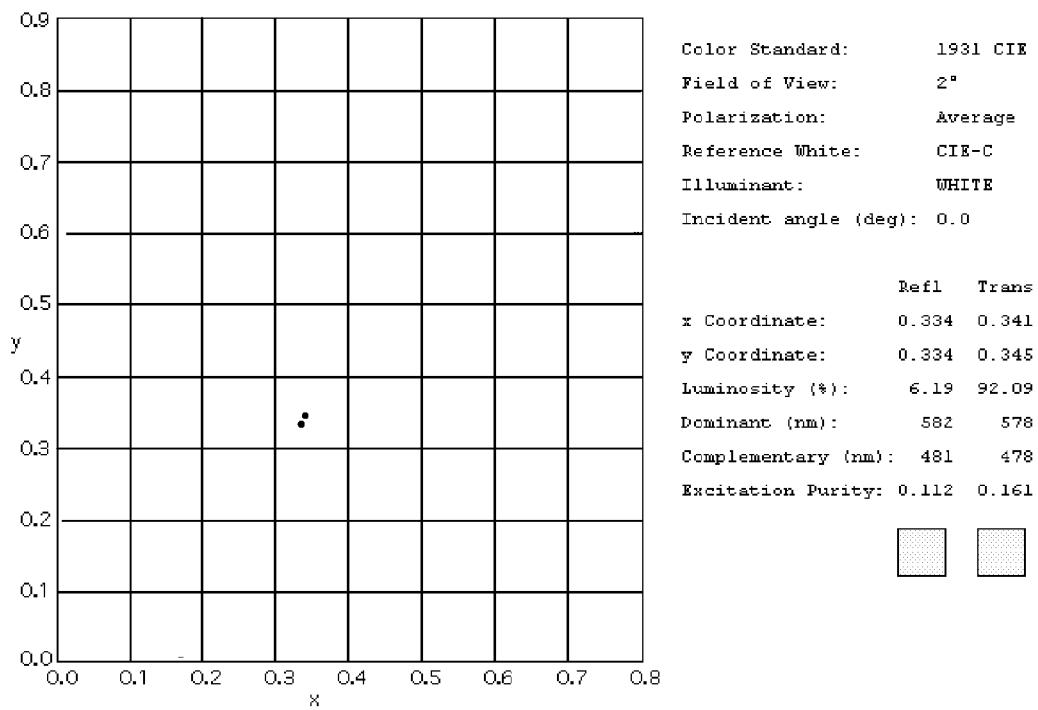
FIG. 29 shows the color plot of a substrate having a blue absorbing dye and a color balancing AR coating.

An AR coating also may be applied to the front of an ophthalmic system (i.e., the surface farthest from the eye of a wearer of the system), resulting in the transmittance and color plot shown in FIGS. 26 and 27, respectively. Although the system exhibits a high transmission and transmitted light is relatively neutral, the reflected light has a CIE of (0.249, 0.090). Therefore, to more completely color balance the effects of the blue absorbing dye, the front AR coating may be modified to achieve the necessary color balance to produce a color neutral configuration. The transmittance and the color plot of this configuration are shown in FIGS. 28 and 29 respectively. In this configuration, both the transmitted and reflected light may be optimized to achieve color neutrality. It may be preferred for the interior reflected light to be about 6%. Should the reflectivity level be annoying to the wearer of the system, the reflection can be further reduced by way of adding an additional different absorbing dye into the lens substrate that would absorb a different wavelength of visible light. However, the design of this configuration achieves remarkable performance and satisfies the need for a blue blocking, color balanced ophthalmic system as described herein. The total transmittance is over 90% and both the transmitted and reflected colors are quite close to the color neutral white point. As shown in FIG. 27, the reflected light has a CIE of (0.334, 0.334), and the transmitted light has a CIE of (0.341, 0.345), indicating little or no color shifting.

In some configurations, the front modified anti-reflection coating can be designed to block 100% of the blue light wave length to be inhibited. However, this may result in a back reflection of about 9% to 10% for the wearer. This level of reflectivity can be annoying to the wearer. Thus by combining an absorbing dye into the lens substrate this reflection with the front modified anti-reflection coating the desired effect can be achieved along with a reduction of the reflectivity to a level that is well accepted by the wearer. The reflected light observed by a wearer of a system including one or more AR coatings may be reduced to 8% or less, or more preferably 3% or less.

The combination of a front and rear AR coating may be referred to as a dielectric stack, and various materials and thicknesses may be used to further alter the transmissive and reflective characteristics of an ophthalmic system. For example, the front AR coating and/or the rear AR coating may be made of different thicknesses and/or materials to achieve a particular color balancing effect. In some cases, the materials used to create the dielectric stack may not be materials traditionally used to create antireflective coatings. That is, the color balancing coatings may correct the color shift caused by a blue absorbing dye in the substrate without performing an antireflective function.

As discussed previously, filters are another technique for blue blocking. Accordingly, any of the blue blocking components discussed could be or include or be combined with blue blocking filters. Such filters may include rugate filters, interference filters, band-pass filters, band-block filters, notch filters or dichroic filters.

In one embodiment, one or more of the above-disclosed blue-blocking techniques may be used in conjunction with other blue-blocking techniques. By way of example only, a lens or lens component may utilize both a dye/tint and a rugate notch filter to effectively block blue light.

Any of the above-disclosed structures and techniques may be employed in an ophthalmic system to perform blocking of blue light wavelengths at or near 400-460 nm. For example, in embodiments the wavelengths of blue light blocked may be within a predetermined range. In embodiments, the range may be 430 nm±30 nm. In other embodiments, the range may be 430 nm±20 nm. In still other embodiments, the range may be 430 nm±10 nm. The term "X±Y nm" means inhibiting wavelengths of light from X nm minus Y nm to X nm plus Y nm. For example, "430 nm±10 nm" means inhibiting wavelengths of light from 420 nm to 440 nm. In embodiments, the ophthalmic system may limit transmission of blue wavelengths within the above-defined ranges to substantially 90% of incident wavelengths. In other embodiments, the ophthalmic system may limit transmission of the blue wavelengths within the above-defined ranges to substantially 80% of incident wavelengths. In other embodiments, the ophthalmic system may limit transmission of the blue wavelengths within the above-defined ranges to substantially 70% of incident wavelengths. In other embodiments, the ophthalmic system may limit transmission of the blue wavelengths within the above-defined ranges to substantially 60% of incident wavelengths. In other embodiments, the ophthalmic system may limit transmission of the blue wavelengths within the above-defined ranges to substantially 50% of incident wavelengths. In other embodiments, the ophthalmic system may limit transmission of the blue wavelengths within the above-defined ranges to substantially 40% of incident wavelengths. In still other embodiments, the ophthalmic system may limit transmission of the blue wavelengths within the above-defined ranges to substantially 30% of incident wavelengths. In still other embodiments, the ophthalmic system may limit transmission of the blue wavelengths within the above-defined ranges to substantially 20% of incident wavelengths. In still other embodiments, the ophthalmic system may limit transmission of the blue wavelengths within the above-defined ranges to substantially 10% of incident wavelengths. In still other embodiments, the ophthalmic system may limit transmission of the blue wavelengths within the above-defined ranges to substantially 5% of incident wavelengths. In still other embodiments, the ophthalmic system may limit transmission of the blue wavelengths within the above-defined ranges to substantially 1% of incident wavelengths. In still other embodiments, the ophthalmic system may limit transmission of the blue wavelengths within the above-defined ranges to substantially 0% of incident wavelengths. Stated otherwise, attenuation by the ophthalmic system of the electromagnetic spectrum at wavelengths in the above-specified ranges may be at least 10%; or at least 20%; or at least 30%; or at least 40%; or at least 50%; or at least 60%; or at least 70%; or at least 80%; or at least 90%; or at least 95%; or at least 99%; or substantially 100%.

In some cases it may be particularly desirable to filter a relatively small portion of the blue spectrum, such as the 400 nm-460 nm region. For example, it has been found that blocking too much of the blue spectrum can interfere with scotopic vision and circadian rhythms. Conventional blue blocking ophthalmic lenses typically block a much larger amount of a wide range of the blue spectrum, which can adversely affect the wearer's "biological clock" and have other adverse effects. Thus, it may be desirable to block a relatively narrow range of the blue spectrum as described herein. Exemplary systems that may filter a relatively small amount of light in a relatively small range include system that block or absorb 5-50%, 5-20%, and 5-10% of light having a wavelength of 400 nm-460 nm, 410 nm-450 nm, and 420 nm-440 nm.

In one embodiment, the ophthalmic system, e.g., a corneal inlay, selectively inhibits light within a range of blue light wavelengths. The inhibited range of blue light wavelengths can be any range within, including the endpoints of, 400 nm to 500 nm. Thus, the inhibited wavelengths can be, for example, 400 to 500 nm, 400 to 475 nm, 400 nm to 470 nm, 400 to 450 nm, 400 to 460 nm, 410 to 450 nm, 420 to 440 nm, or about 430 nm. In another embodiment, the size of the inhibited range of blue light wavelengths, as measured by full-width at half-maximum (FWHM), is no more than about 100 nm, about 75 nm, about 60 nm, about 50 nm, about 40 nm, about 30 nm, about 20 nm, about 10 nm, or about 5 nm.

In one embodiment, the inhibited range of blue light wavelengths includes 430 nm because blue light having a wavelength of 430 nm is known to excite chromophore A2E. In another embodiment, the inhibited range of blue light wavelengths includes and/or peaks at one or more singularly damaging wavelengths. By selectively filtering particular wavelength ranges, the ophthalmic systems described herein can optimize the trade-off between achieving protection from harmful wavelengths and maintaining acceptable color cosmetics, color perception, overall light transmission, photopic vision, scotopic vision, color vision, and/or cirdadian rhythms.

To selectively inhibit light within a range of blue light wavelengths, the ophthalmic system transmits less than about 90%, less than about 80%, less than about 70%, less than about 60%, or less than about 50%, of light within the range of blue light wavelengths. In one embodiment, the system transmits about 0% to about 90% or increments therein, of light within the range of blue light wavelengths. In another embodiment, the system transmits about 20% to about 30% of light within the range of blue light wavelengths.

The term "increments therein" is meant to explicitly enumerate all values and ranges from the lower value to the upper value in increments of any measurable degree of precision. For example, if a variable is from 0 to 90 or increments therein, values and ranges such as 0 to 80, 30 to 75, 22 to 68, 43 to 51, 32, 30.3, etc. are expressly contemplated as part of this invention.

At the same time as wavelengths of blue light are selectively blocked as described above, at least 80%, at least 85%, at least 90%, or at least 95% of other portions of the visual electromagnetic spectrum may be transmitted by the ophthalmic system. Stated otherwise, attenuation by the ophthalmic system of the electromagnetic spectrum at wavelengths outside the blue light spectrum, e.g. wavelengths other than those in a range around 430 nm may be 20% or less, 15% or less, 10% or less, and in other embodiments, 5% or less.

Additionally, some embodiments may further block ultraviolet radiation the UVA and UVB spectral bands as well as infra-red radiation with wavelengths greater than 700 nm.

Any of the above-disclosed ophthalmic system may be incorporated into an article of eyewear, including externally-worn eyewear such as eyeglasses, sunglasses, goggles or contact lenses. In such eyewear, because the blue-blocking component of the systems is posterior to the color balancing component, the blue-blocking component will always be closer to the eye than the color-balancing component when the eyewear is worn. The ophthalmic system may also be used in such articles of manufacture as surgically implantable intra-ocular lenses.

Several embodiments use a film to block the blue light. The film in an ophthalmic or other system may selectively inhibit at least 5%, at least 10%, at least 20%, at least 30%, at least 40%, and/or at least 50% of blue light within the 400 nm-460 nm range. As used herein, a film "selectively inhibits" a wavelength range if it inhibits at least some transmission within the range, while having little or no effect on transmission of visible wavelengths outside the range. The film and/or a system incorporating the film may be color balanced to allow for being perception by an observer and/or user as colorless. Systems incorporating a film may have a scotopic luminous transmission of 85% or better of visible light, and further allow someone looking through the film or system to have mostly normal color vision.

Figure 30:
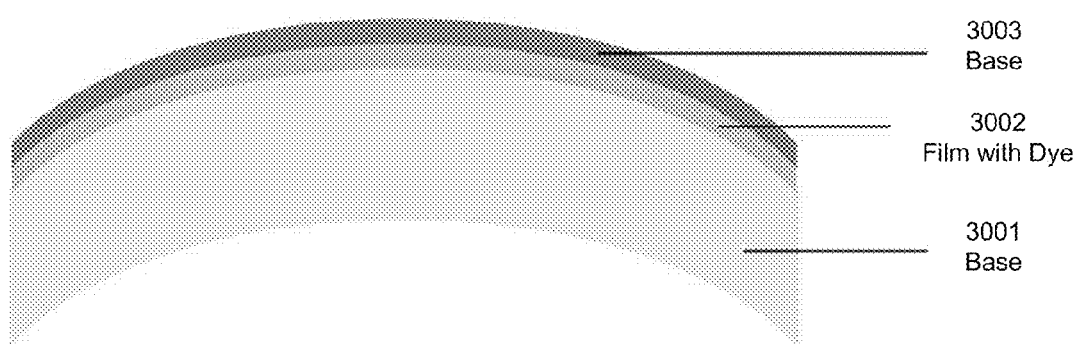
FIG. 30 shows an exemplary ophthalmic device comprising a film.

FIG. 30 shows an exemplary embodiment. A film 3002 may be disposed between two layers or regions of one or more base materials 3001, 3003. As further described herein, the film may contain a dye that selectively inhibits certain wavelengths of light. The base material or materials may be any material suitable for a lens, ophthalmic system, window, or other system in which the film may be disposed.

Figure 31:
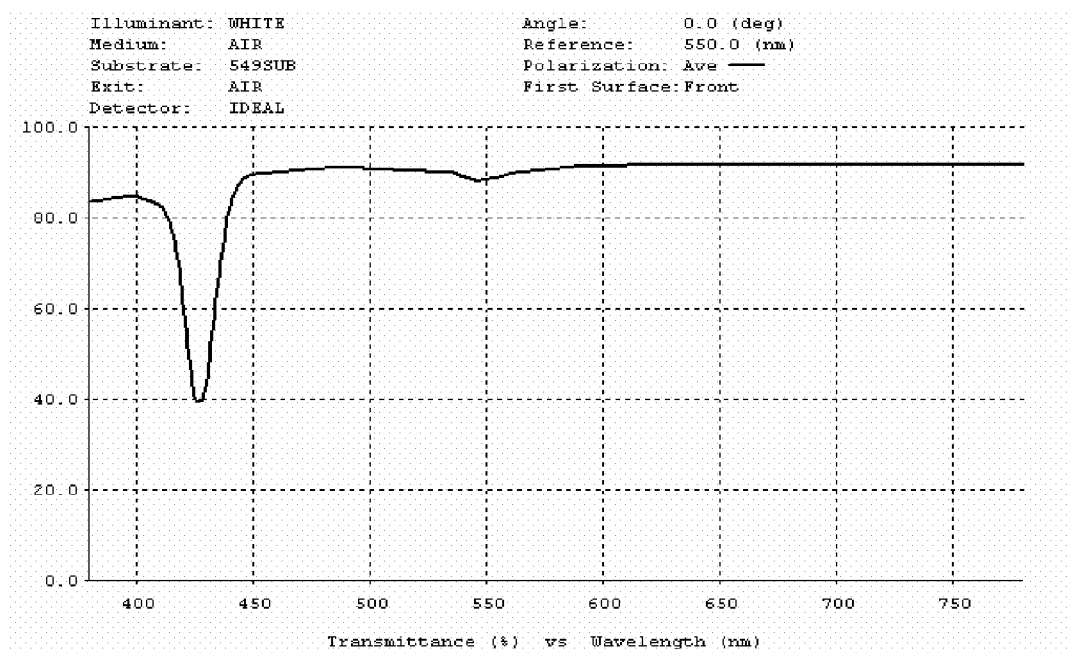
FIG. 31 shows the optical transmission characteristic of an exemplary film.

The optical transmission characteristic of an exemplary film is shown in FIG. 31 where about 50% of blue light in the range of 430 nm+10 nm is blocked, while imparting minimal losses on other wavelengths within the visible spectrum. The transmission shown in FIG. 31 is exemplary, and it will be understood that for many applications it may be desirable to selectively inhibit less than 50% of blue light, and/or the specific wavelengths inhibited may vary. It is believed that in many applications cell death may be reduced or prevented by blocking less than 50% of blue light. For example, it may be preferred to selectively inhibit about 40%, more preferably about 30%, more preferably about 20%, more preferably about 10%, and more preferably about 5% of light in the 400-460 nm range. Selectively inhibiting a smaller amount of light may allow for prevention of damage due to high-energy light, while being minimal enough that the inhibition does not adversely affect scotopic vision and/or circadian cycles in a user of the system.

Figure 32:
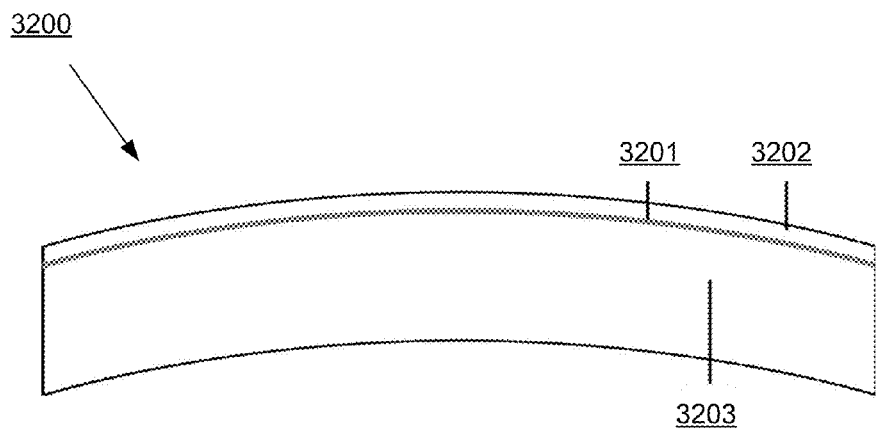
FIG. 32 shows an exemplary ophthalmic system comprising a film.

FIG. 32 shows a film 3201 incorporated into an ophthalmic lens 3200, where it is sandwiched between layers of ophthalmic material 3202, 3203. The thickness of the front layer of ophthalmic material is, by way of example only, in the range of 200 microns to 1,000 microns.

Figure 33:
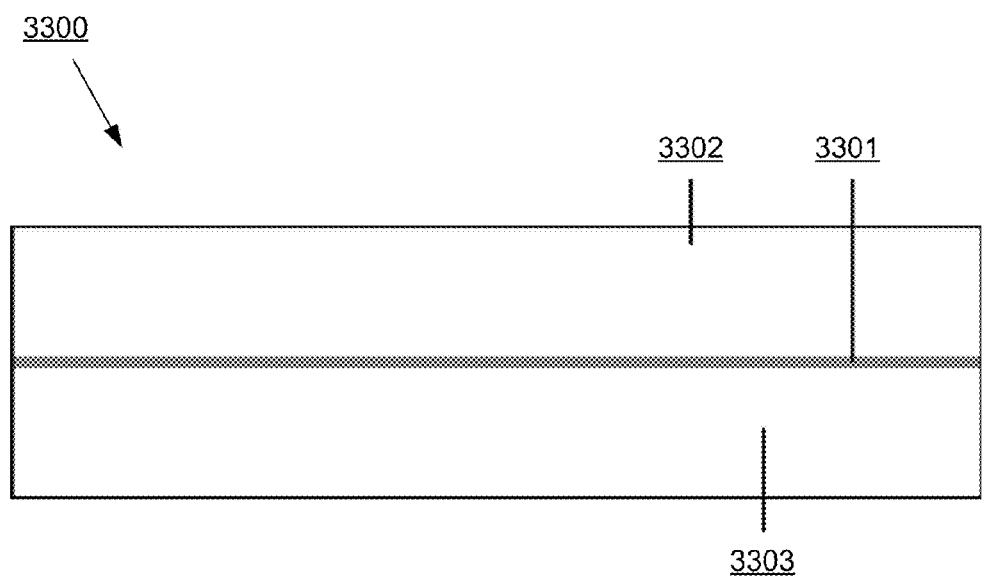
FIG. 33 shows an exemplary system comprising a film.

Similarly, FIG. 33 shows an exemplary system 3300, such as an automotive windshield. A film 3301 may be incorporated into the system 3300, where it is sandwiched between layers of base material 3302, 3303. For example, where the system 3300 is an automotive windshield, the base material 3302, 3303 may be windshield glass as is commonly used. It will be understood that in various other systems, including visual, display, ophthalmic, and other systems, different base materials may be used without departing from the scope of the present invention.

In an embodiment, a system may be operated in an environment where the relevant emitted visible light has a very specific spectrum. In such a regime, it may be desirable to tailor a film's filtering effect to optimize the light transmitted, reflected, or emitted by the item. This may be the case, for example, where the color of the transmitted, reflected, or emitted light is of primary concern. For example, when a film is used in or with a camera flash or flash filter, it may be desirable for the perceived color of the image or print to be as close to true color as possible. As another example, a film may be used in instrumentation for observing the back of a patient's eye for disease. In such a system, it may be important for the film not to interfere with the true and observed color of the retina. As another example, certain forms of artificial lighting may benefit from a wavelength-customized filter utilizing the inventive film.

In an embodiment, the inventive film may be utilized within a photochromatic, electrochromic, or changeable tint ophthalmic lens, window or automotive windshield. Such a system may allow for protection from UV light wavelengths, direct sunlight intensity, and blue light wavelengths in an environment where the tinting is not active. In this embodiment the film's blue light wavelengths protective attributes may be effective regardless of whether the tinting is active.

In an embodiment, a film may allow for selective inhibition of blue light while being color balanced and will have an 85% or greater scotopic luminous transmission of visible light. Such a film may be useful for lower light transmission uses such as driving glasses or sport glasses, and may provide increased visual performance due to increased contrast sensitivity.

For some applications, it may be desirable for a system to selectively inhibit blue light as described herein, and have a luminous transmission of less than about 85%, typically about 80-85%, across the visible spectrum. This may be the case where, for example, a base material used in the system inhibits more light across all visible wavelengths due to its higher index of refraction. As a specific example, high index (e.g., 1.7) lenses may reflect more light across wavelengths leading to a luminous transmission less than 85%.

To avoid, reduce, or eliminate problems present in conventional blue-blocking systems, it may be desirable to reduce, but not eliminate, transmission of phototoxic blue light. The pupil of the eye responds to the photopic retinal illuminance, in trolands, which is the product of the incident flux with the wavelength-dependent sensitivity of the retina and the projected area of the pupil. A filter placed in front of the retina, whether within the eye, as in an intraocular lens, attached to the eye, as in a contact lens or corneal replacement, or otherwise in the optical path of the eye as in a spectacle lens, may reduce the total flux of light to the retina and stimulate dilation of the pupil, and thus compensate for the reduction in field illuminance. When exposed to a steady luminance in the field the pupil diameter generally fluctuates about a value that increases as the luminance falls.

Figure 34A:
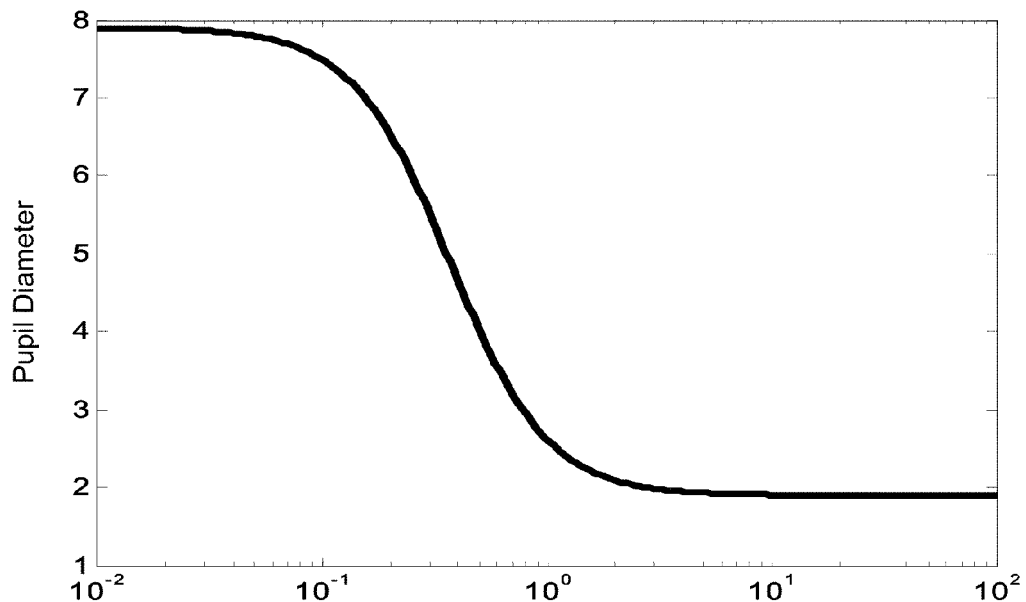
FIGS. 34A and B show pupil diameter and pupil area, respectively, as a function of field illuminance.
Figure 34B:
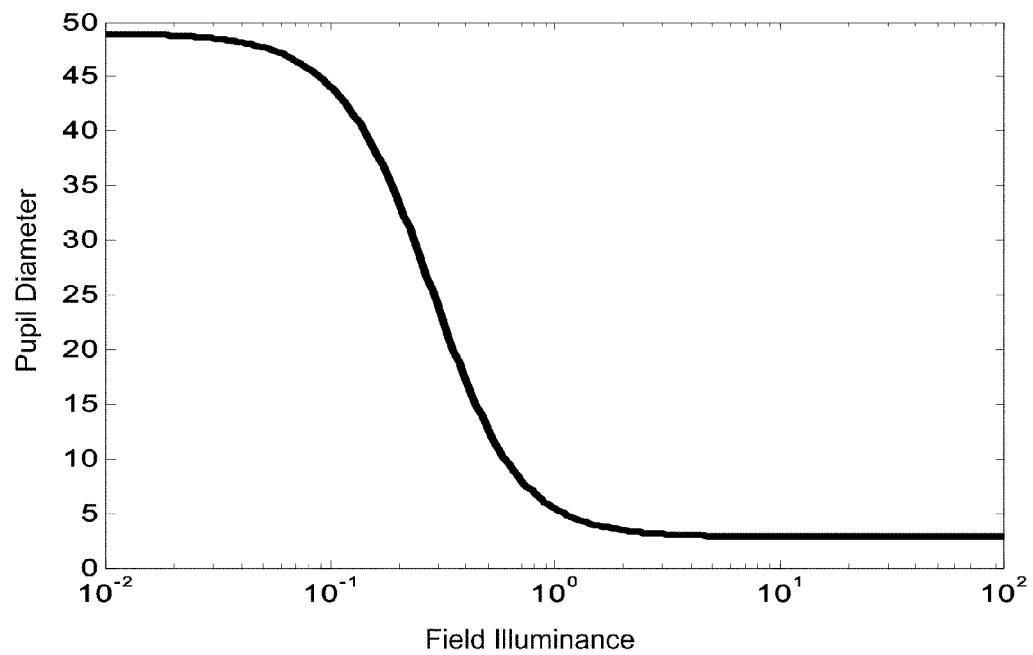

A functional relationship between pupil area and field illuminance described by Moon and Spencer, J. Opt. Soc. Am. v. 33, p. 260 (1944) using the following equation for pupil diameter:

$$d = 4.9 - 3 \tan h(\text{Log}(L)+1) \quad (0.1)$$

where d is in millimeters and L is the illuminance in cd/m². FIG. 34A shows pupil diameter (mm) as a function of field illuminance (cd/m²). FIG. 34B shows pupil area (mm²) as a function of field illuminance.

The illuminance is defined by the international CIE standards as a spectrally weighted integration of visual sensitivity over wavelength:

$$L = K_m \int L_{e,\lambda} V_\lambda d\lambda \text{ photopic}$$

$$L' = K'_m \int L_{e,\lambda} V'_\lambda d\lambda \text{ scotopic} \quad (0.2)$$

where $K_m'$ is equal to 1700.06 lm/W for scotopic (night) vision, $K_m = 683.2$ μm/W for photopic (day) vision and the spectral luminous efficiency functions $V_\lambda$ and $V_\lambda'$ define the standard photopic and scotopic observers. The luminous efficiency functions $V_\lambda$ and $V_\lambda'$ are illustrated in, e.g., FIG. 9 of Michael Kalloniatis and Charles Luu, "Psychophysics of Vision," available at http://webvision.med.utah.edu/Phych1.html, last visited Aug. 8, 2007, which is incorporated by reference herein.

Interposition of an absorptive ophthalmic element in the form of an intraocular, contact, or spectacle lens reduces the illuminance according to the formula:

$$L = K_m \int T_\lambda L_{e,\lambda} V_\lambda d\lambda \text{ photopic}$$

$$L' = K'_m \int T_\lambda L_{e,\lambda} V'_\lambda d\lambda \text{ scotopic}$$

where $T_\lambda$ is the wavelength-dependent transmission of the optical element. Values for the integrals in equation 1.3 normalized to the unfiltered illuminance values computed from equation 1.2 for each of the prior-art blue blocking lenses are shown in Table I.

TABLE I

| Reference | FIG. | Photopic Ratio | Scotopic Ratio |
|---|---|---|---|
| Unfiltered | | 1.000 | 1.000 |
| Pratt '430 | | 0.280 | 0.164 |
| Mainster 2005/0243272 | | 0.850 | 0.775 |
| Present System | 35 | 0.996 | 0.968 |
| Present System | 36 (solid line) | 0.993 | 0.947 |
| Present System | 37 | 0.978 | 0.951 |

Referring to Table I, the ophthalmic filter according to Pratt reduces scotopic sensitivity by 83.6% of its unfiltered value, an attenuation that will both degrade night vision and stimulate pupil dilation according to equation 1.1. The device described by Mainster reduces scotopic flux by 22.5%, which is less severe than the Pratt device but still significant.

In contrast, a film as disclosed herein may partially attenuates violet and blue light using absorptive or reflective ophthalmic elements while reducing the scotopic illuminance by no more than 15% of its unfiltered value. Surprisingly, such systems were found to selectively inhibit a desired region of blue light, while having little to no effect on photopic and scotopic vision.

Figure 35:
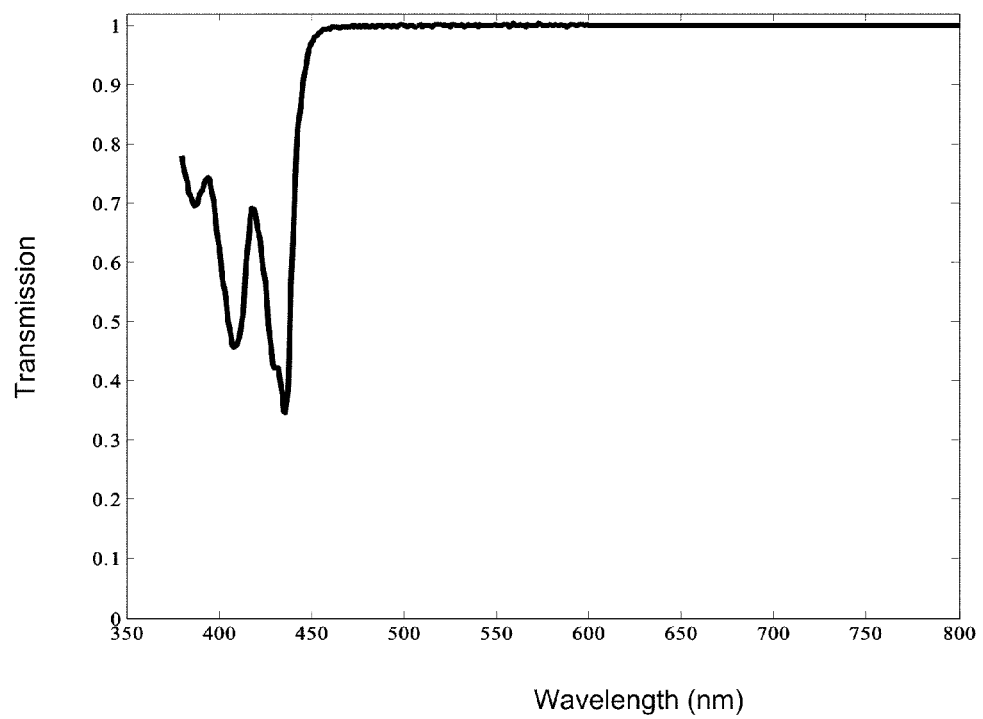
FIG. 35 shows the transmission spectrum of a film that is doped with perylene dye where the product of concentration and path length yield about 33% transmission at about 437 nm.
Figure 36:
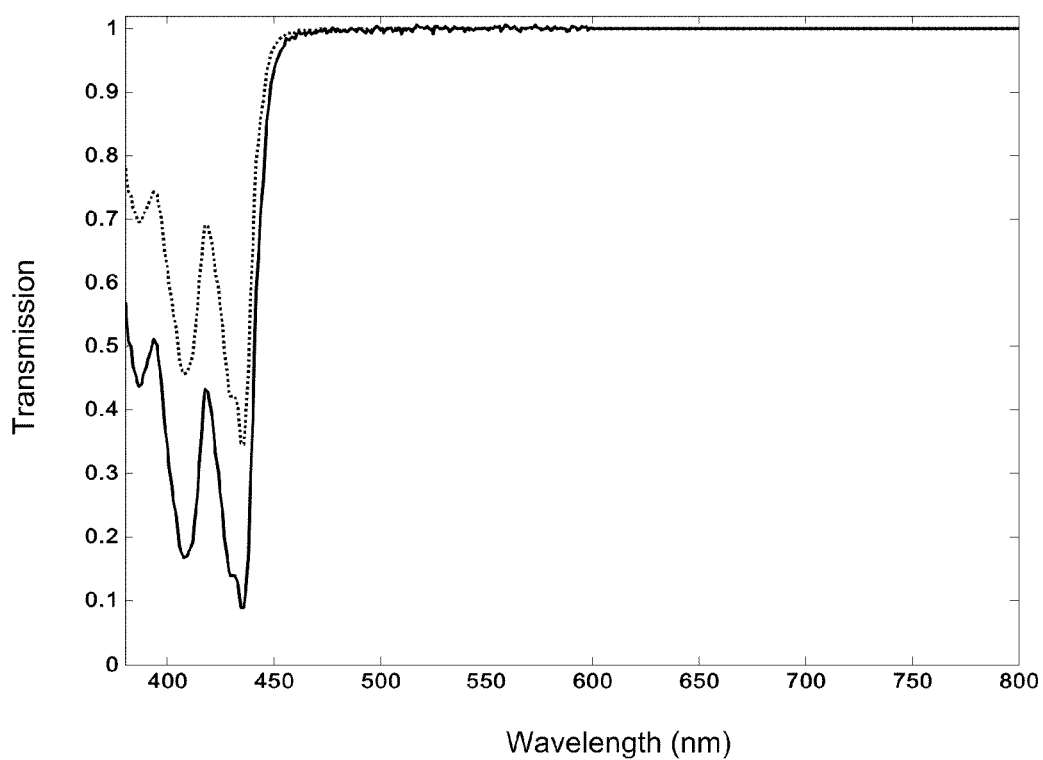
FIG. 36 shows the transmission spectrum of a film with a perylene concentration about 2.27 times higher than that illustrated in the previous figure.

In an embodiment, perylene ($C_{20}H_{12}$, CAS # 198-55-0) is incorporated into an ophthalmic device at a concentration and thickness sufficient to absorb about two-thirds of the light at its absorption maximum of 437 nm. The transmission spectrum of this device is shown in FIG. 35. Perylene provides selective filtering of high energy visible blue light wavelengths in the range of 430 nm±20 nm. More specifically, perylene provides a notch at 420 nm. Perylene can also provide increased contrast sensitivity. The loading level of perylene dye is selected to minimize any effect on the scoptopic vision, bio-rhythms, color vision, and pupil dilation of the wearer. The change in illuminance that results from this filter is only about 3.2% for scotopic viewing conditions and about 0.4% under photopic viewing conditions, as displayed in Table I. Increasing the concentration or thickness of perylene in the device decreases the transmission at each wavelength according to Beer's law. FIG. 36 shows the transmission spectrum of a device with a perylene concentration 2.27 times higher than that for FIG. 35. Although this device selectively blocks more of the phototoxic blue light than the device in FIG. 35, it reduces scotopic illuminance by less than 6% and photopic illuminance by less than 0.7%. Note that reflection has been removed from the spectra in FIGS. 35 and 36 to show only the effect of absorption by the dye.

Figure 46:
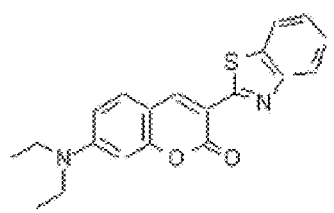
FIG. 46 shows exemplary dyes.
Figure 46:
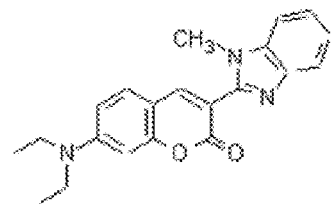
Figure 46:
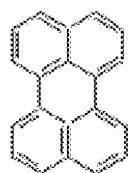
Figure 46:
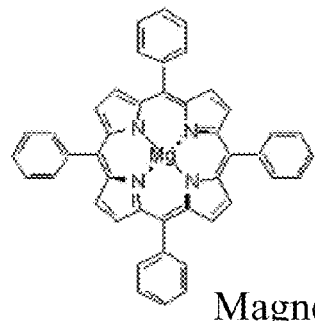
Figure 46:
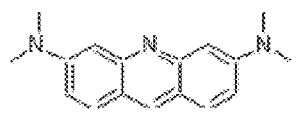
Figure 46:
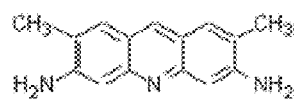

Dyes other than perylene may have strong absorption in blue or roughly blue wavelength ranges and little or no absorbance in other regions of the visible spectrum. Examples of such dyes, illustrated in FIG. 46, include porphyrin, coumarin, and acridine based molecules which may be used singly or in combination to give transmission that is reduced, but not eliminated, at 400 nm-460 nm. The methods and systems described herein therefore may use similar dyes based on other molecular structures at concentrations that mimic the transmission spectra of perylene, porphyrin, coumarin, and acridine.

The insertion of dye into the optical path may be accomplished by diverse methods familiar to those practiced in the art of optical manufacturing. The dye or dyes may be incorporated directly into the substrate, added to a polymeric coating, imbibed into the lens, incorporated in a laminated structure that includes a dye-impregnated layer, or as a composite material with dye-impregnated microparticles.

Figure 37:
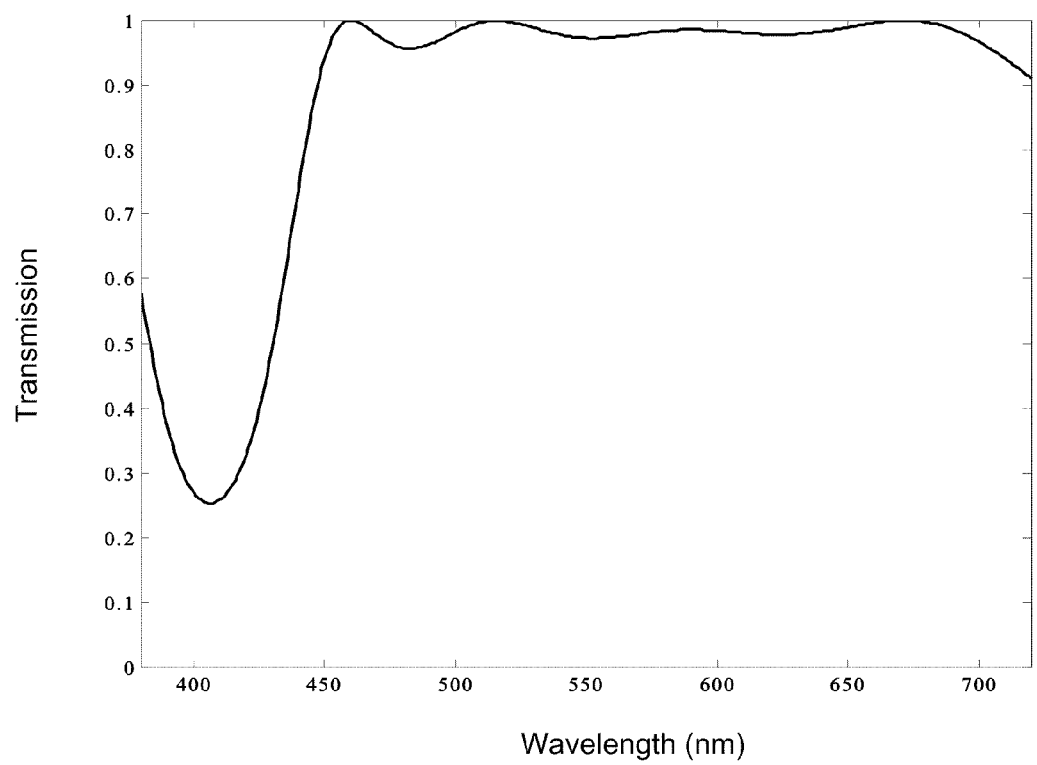
FIG. 37 shows an exemplary transmission spectrum for a six-layer stack of $SiO_2$ and $ZrO_2$.

According to another embodiment, a dielectric coating that is partially reflective in the violet and blue spectral regions and antireflective at longer wavelengths may be applied. Methods for designing appropriate dielectric optical filters are summarized in textbooks such as Angus McLeod, Thin Film Optical Filters (McGraw-Hill: NY) 1989. An exemplary transmission spectrum for a six-layer stack of $SiO_2$ and $ZrO_2$ is shown in FIG. 37. Referring again to Table I, it is seen that this optical filter blocks phototoxic blue and violet light while reducing scotopic illuminance by less than 5% and photopic illuminance by less than 3%.

Although many conventional blue blocking technologies attempt to inhibit as much blue light as possible, current research suggests that in many applications it may be desirable to inhibit a relatively small amount of blue light. For example, to prevent undesirable effects on scotopic vision, it may be desirable for an ophthalmic system to inhibit only about 30% of blue (i.e., 380-500 nm) wavelength light, or more preferably only about 20% of blue light, more preferably about 10%, and more preferably about 5%. It is believed that cell death may be reduced by inhibiting as little as 5% of blue light, while this degree of blue light reduction has little or no effect on scotopic vision and/or circadian behavior of those using the system.

As used herein, a film that selectively inhibits blue light is described as inhibiting an amount of light measured relative to the base system incorporating the film. For example, an ophthalmic system may use a polycarbonate or other similar base for a lens. Materials typically used for such a base may inhibit a various amount of light at visible wavelengths. If a blue-blocking film is added to the system, it may selectively inhibit 5%, 10%, 20%, 30%, 40%, and/or 50% of all blue wavelengths, as measured relative to the amount of light that would be transmitted at the same wavelength(s) in the absence of the film.

The methods and devices disclosed herein may minimize, and preferably eliminate, the shift in color perception that results from blue-blocking. The color perceived by the human visual system results from neural processing of light signals that fall on retinal pigments with different spectral response characteristics. To describe color perception mathematically, a color space is constructed by integrating the product of three wavelength-dependent color matching functions with the spectral irradiance. The result is three numbers that characterize the perceived color. A uniform (L*, a*, b*) color space, which has been established by the Commission Internationale de L'eclairage (CIE), may be used to characterize perceived colors, although similar calculations based on alternative color standards are familiar to those practiced in the art of color science and may also be used. The (L*, a*, b*) color space defines brightness on the L* axis and color within the plane defined by the a* and b* axes. A uniform color space such as that defined by this CIE standard may be preferred for computational and comparative applications, since the Cartesian distances of the space are proportional to the magnitude of perceived color difference between two objects. The use of uniform color spaces generally is recognized in the art, such as described in Wyszecki and Stiles, Color Science: Concepts and Methods, Quantitative Data and Formulae (Wiley: New York) 1982.

Figure 38:
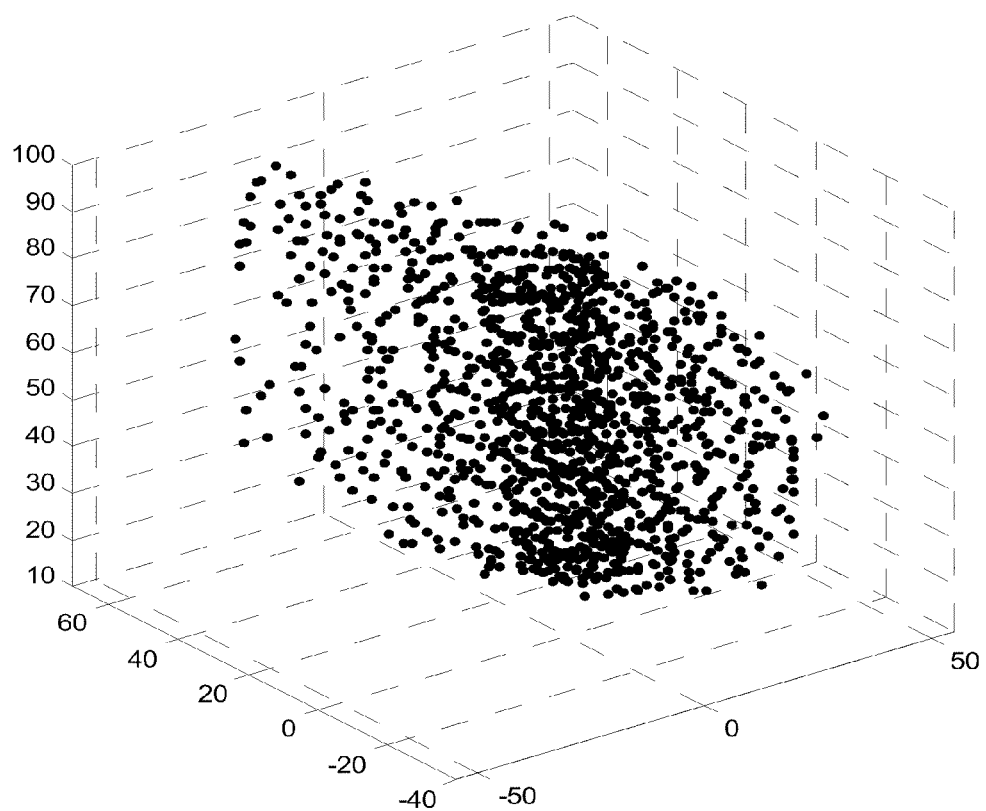
FIG. 38 shows reference color coordinates corresponding to Munsell tiles illuminated by a prescribed illuminant in (L*, a*, b*) color space.
Figure 39A:
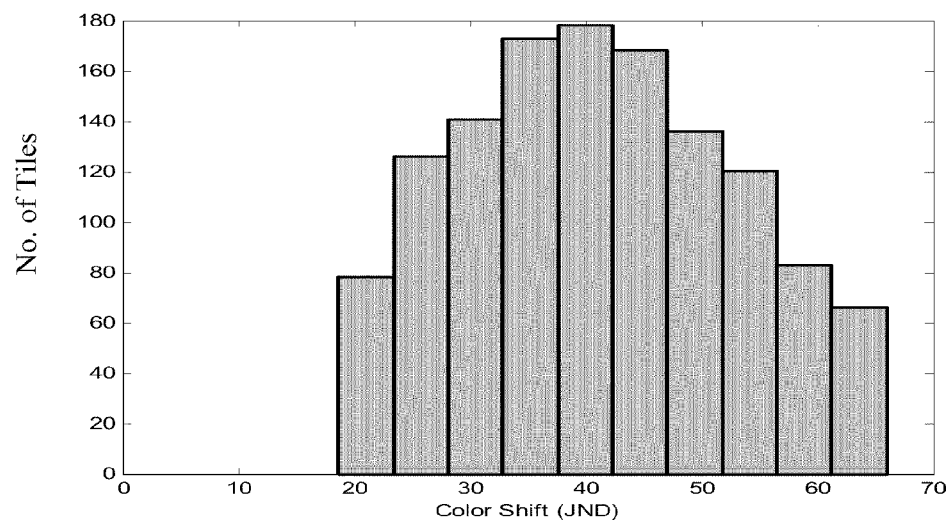
FIG. 39A shows a histogram of the color shifts for Munsell color tiles for a related filter.

An optical design according to the methods and systems described herein may use a palette of spectra that describe the visual environment. A non-limiting example of this is the Munsell matte color palette, which is comprised of 1,269 color tiles that have been established by psychophysical experiments to be just noticeably different from each other. The spectral irradiance of these tiles is measured under standard illumination conditions. The array of color coordinates corresponding to each of these tiles illuminated by a D65 daylight illuminant in (L*, a*, b*) color space is the reference for color distortion and is shown in FIG. 38. The spectral irradiance of the color tiles is then modulated by a blue-blocking filter and a new set of color coordinates is computed. Each tile has a perceived color that is shifted by an amount corresponding to the geometric displacement of the (L*, a*, b*) coordinates. This calculation has been applied to the blue-blocking filter of Pratt, where the average color distortion is 41 just noticeable difference (JND) units in (L*, a*, b*) space. The minimum distortion caused by the Pratt filter is 19 JNDs, the maximum is 66, and the standard deviation is 7 JNDs. A histogram of the color shifts for all 1,269 color tiles is shown in FIG. 39A (top).

Figure 39B:
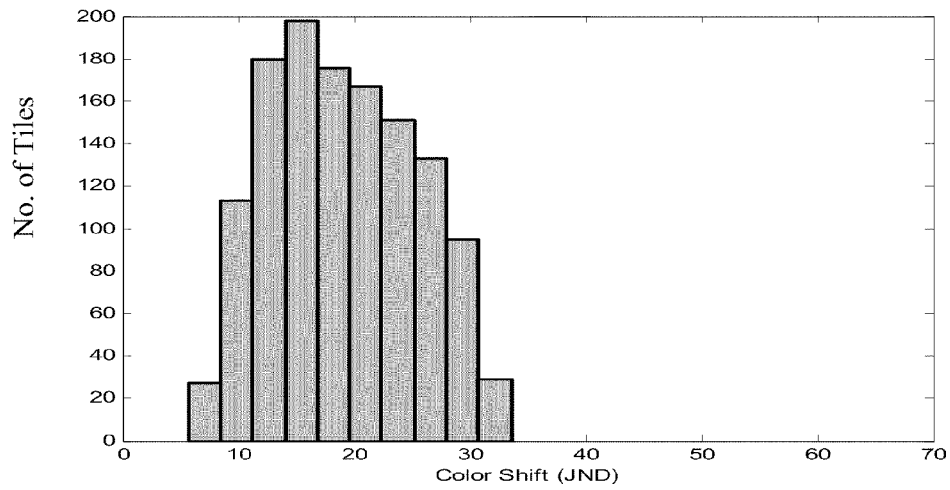
FIG. 39B shows a color shift induced by a related blue-blocking filter.

Referring now to FIG. 39B, the color shift induced by the Mainster blue-blocking filter has a minimum value of 6, an average of 19, a maximum of 34, and a standard deviation of 6 JNDs.

Figure 40:
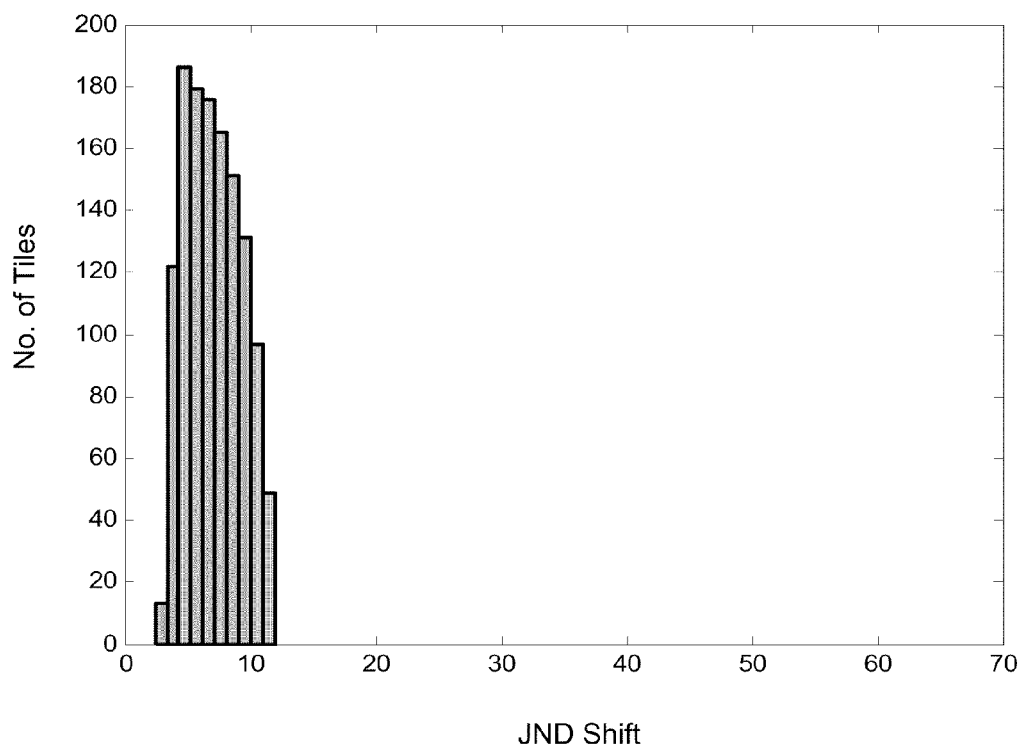
FIG. 40 shows a histogram of color shifts for a perylene-dyed substrate.

Embodiments using perylene dye at two concentrations or the reflective filter described above may have substantially smaller color shifts than conventional devices whether measured as an average, minimum, or maximum distortion, as illustrated in Table II. FIG. 40 shows a histogram of color shifts for a perylene-dyed substrate whose transmission spectrum is shown in FIG. 35. Notably, the shift across all color tiles was observed to be substantially lower and narrower than those for conventional devices described by Mainster, Pratt, and the like. For example, simulation results showed (L*, a*, b*) shifts as low as 12 and 20 JNDs for exemplary films, with average shifts across all tiles as low as 7-12 JNDs.

TABLE II

| Reference | FIG. | Avg. δ (L*, a*, b*) | Min. δ (L*, a*, b*) | Max. δ (L*, a*, b*) | Std. Deviation δ (L*, a*, b*) |
|---|---|---|---|---|---|
| Pratt | | 41 | 19 | 66 | 12 |
| Mainster | | 19 | 6 | 34 | 6 |
| Present System | 35 | 7 | 2 | 12 | 2 |
| Present System | 36 | 12 | 4 | 20 | 3 |
| Present System | 37 | 7 | 2 | 12 | 2 |

Figure 41:
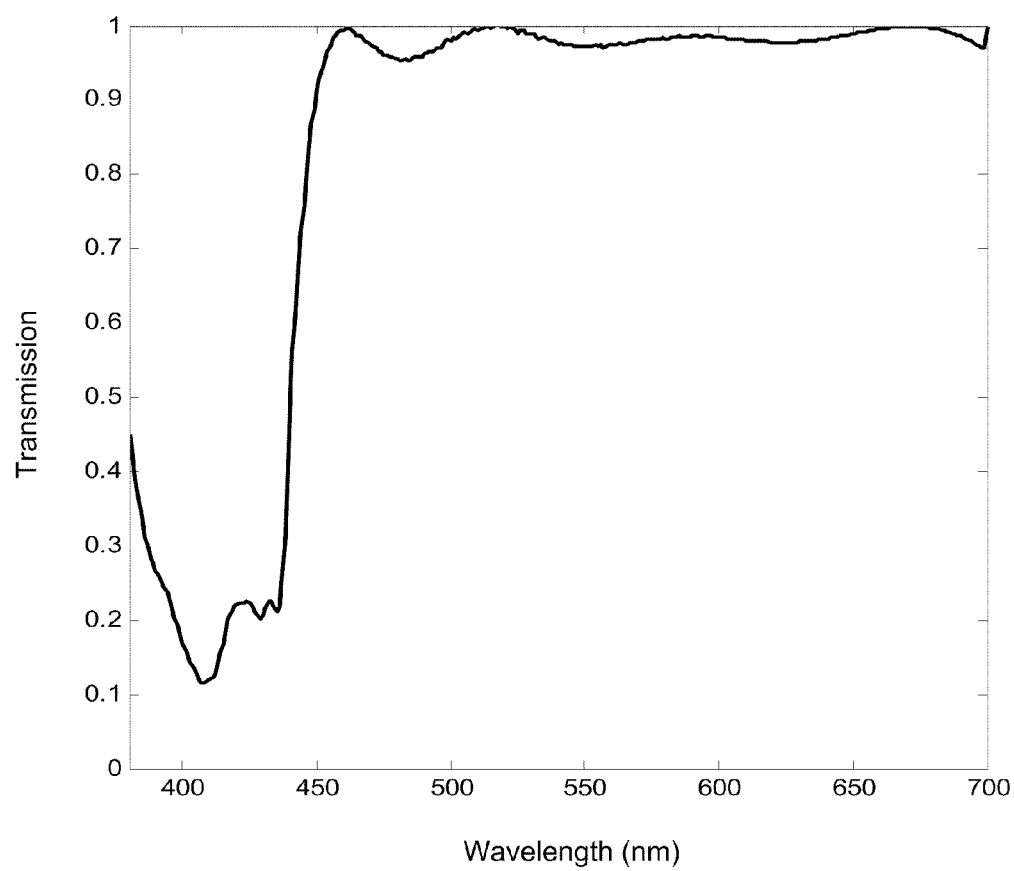
FIG. 41 shows the transmission spectrum of a system combining dielectric stacks and perylene dye.
Figure 42:
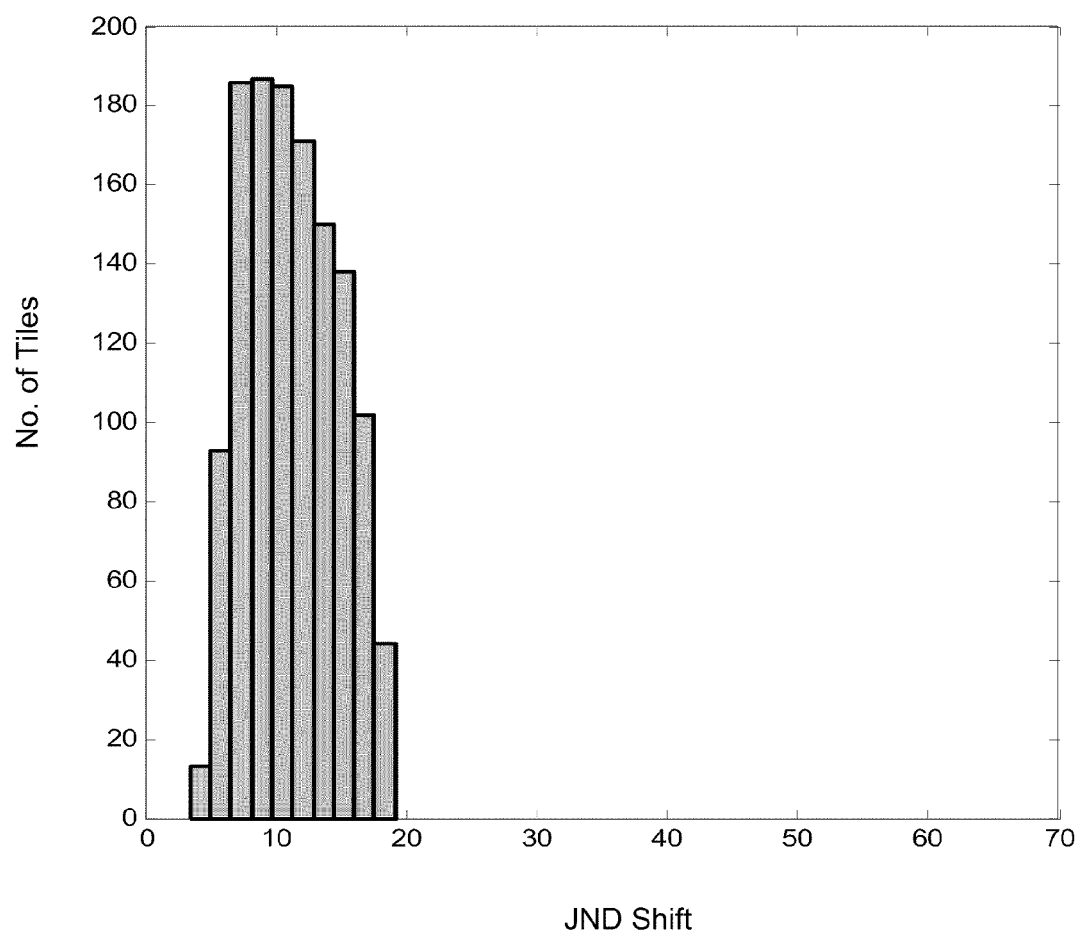
FIG. 42 shows a histogram summarizing color distortion of a device for Munsell tiles in daylight.

In an embodiment, a combination of reflective and absorptive elements may filter harmful blue photons while maintaining relatively high luminous transmission. This may allow a system to avoid or reduce pupil dilation, preserve or prevent damage to night vision, and reduce color distortion. An example of this approach combines the dielectric stacks shown in FIG. 37 with the perylene dye of FIG. 35, resulting in the transmission spectrum shown in FIG. 41. The device was observed to have a photopic transmission of 97.5%, scotopic transmission of 93.2%, and an average color shift of 11 JNDs. The histogram summarizing color distortion of this device for the Munsell tiles in daylight is shown in FIG. 42.

Figure 43A:
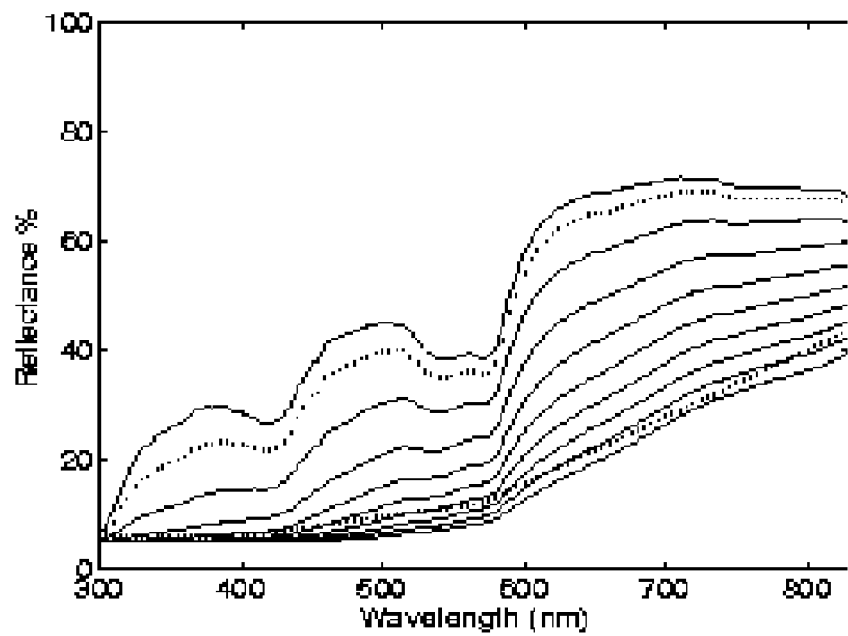
FIGS. 43A-43B show representative series of skin reflectance spectra from subjects of different races.
Figure 43B:
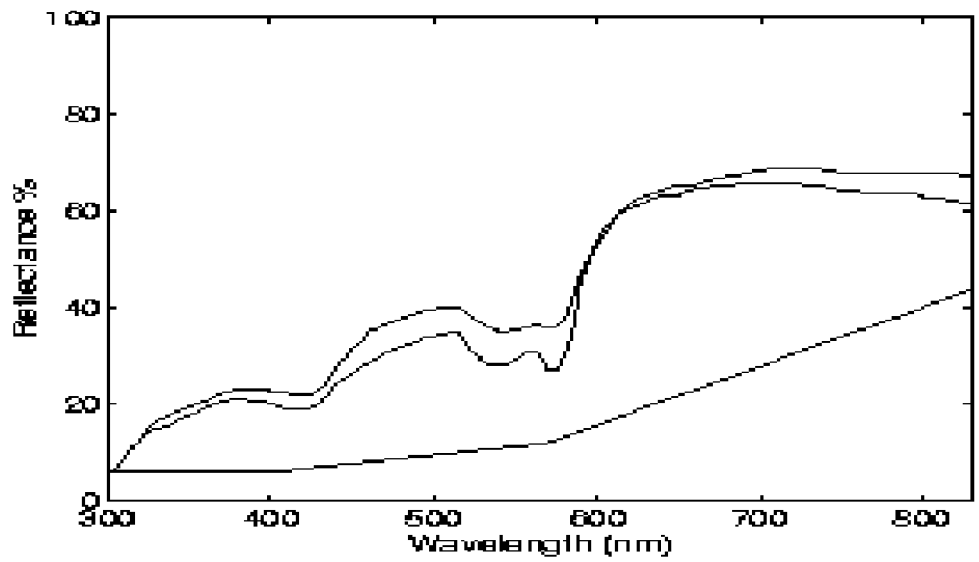
Figure 44:
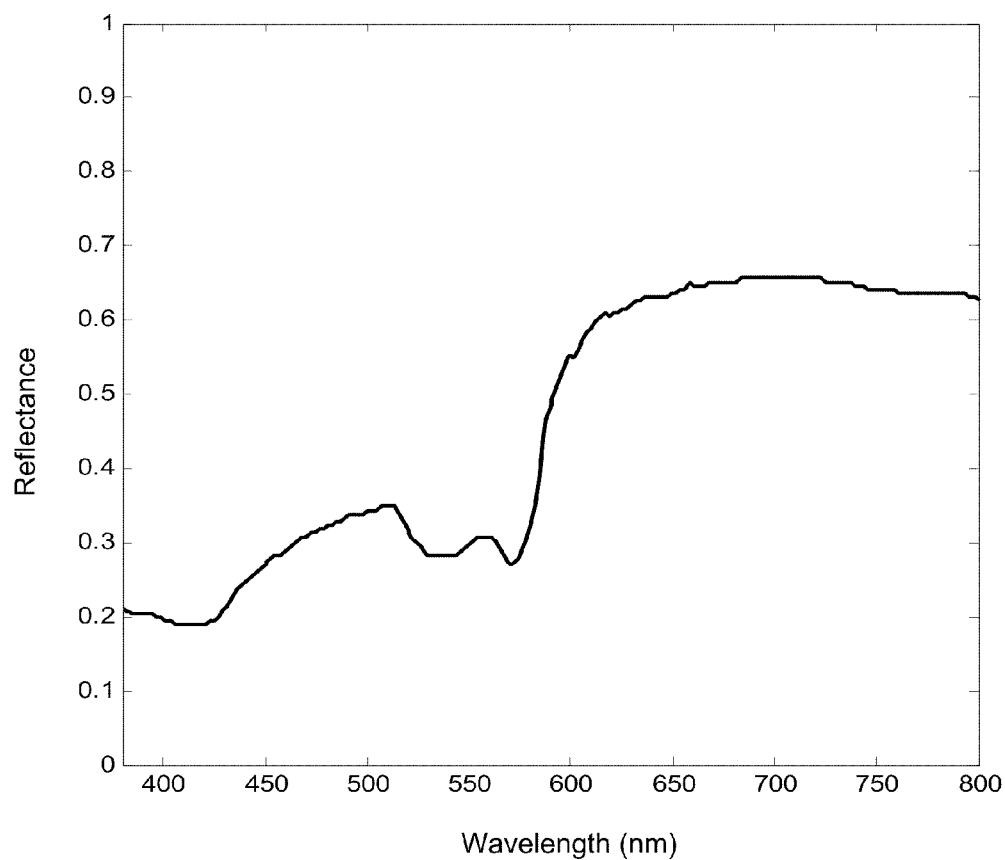
FIG. 44 shows an exemplary skin reflectance spectrum for a Caucasian subject.

In another embodiment, an ophthalmic filter is external to the eye, for example a spectacle lens, goggle, visor, or the like. When a traditional filter is used, the color of the wearer's face when viewed by an external observer may be tinted by the lens, i.e., the facial coloration or skin tone typically is shifted by a blue-blocking lens when viewed by another person. This yellow discoloration that accompanies blue light absorption is often not cosmetically desirable. The procedure for minimizing this color shift is identical to that described above for the Munsell tiles, with the reflectance of the wearer's skin being substituted for those of the Munsell color tiles. The color of skin is a function of pigmentation, blood flow, and the illumination conditions. A representative series of skin reflectance spectra from subjects of different races is shown in FIGS. 43A-B. An exemplary skin reflectance spectrum for a Caucasian subject is shown in FIG. 44. The (L*, a*, b*) color coordinates of this skin in daylight (D65) illumination are (67.1, 18.9, 13.7). Interposition of the Pratt blue-blocking filter changes these color coordinates to (38.9, 17.2, 44.0), a shift of 69 JND units. The Mainster blue-blocking filter shifts the color coordinates by 17 JND units to (62.9, 13.1, 29.3). By contrast, a perylene filter as described herein causes a color shift of only 6 JNDs, or one third that of the Mainster filter. A summary of the cosmetic color shift of an exemplary Caucasian skin under daylight illumination using various blue-blocking filters is shown in Table III. The data shown in Table I refer are normalized to remove any effect caused by a base material.

TABLE III

| Reference | FIG. | L* | a* | b* | δ (L*, a*, b*) |
|---|---|---|---|---|---|
| Skin | 14-15 | 67 | 19 | 14 | 0 |
| Pratt | | 39 | 17 | 44 | 69 |
| Mainster | | 63 | 13 | 29 | 17 |
| Present System | 35 | 67 | 17 | 19 | 6 |
| Present System | 36 | 67 | 15 | 23 | 10 |
| Present System | 37 | 67 | 17 | 19 | 6 |

In an embodiment, an illuminant may be filtered to reduce but not eliminate the flux of blue light to the retina. This may be accomplished with absorptive or reflective elements between the field of view and the source of illumination using the principles described herein. For example, an architectural window may be covered with a film that contains perylene so that the transmission spectrum of the window matches that shown in FIG. 35. Such a filter typically would not induce pupil dilation when compared to an uncoated window, nor would it cause appreciable color shifts when external daylight passes through it. Blue filters may be used on artificial illuminants such as fluorescent, incandescent, arc, flash, and diode lamps, displays, and the like.

Various materials may be used in making films. Two such exemplary materials are Poly Vinyl Alcohol (PVA) and Poly Vinyl Butyral (PVB). In the case of PVA film it may be prepared by partial or complete hydrolysis of polyvinyl acetate to remove the acetate groups. PVA film may be desirable due to beneficial film forming, emulsifying, and adhesive properties. In addition, PVA film has high tensile strength, flexibility, high temperature stability, and provides an excellent oxygen barrier.

PVB film may be prepared from a reaction of polyvinyl alcohol in butanal. PVB may be suitable for applications that require high strength, optical clarity, flexibility and toughness. PVB also has excellent film forming and adhesive properties.

PVA, PVB, and other suitable films may be extruded, cast from a solution, spin coated and then cured, or dip coated and then cured. Other manufacturing methods known in the art also may be used. There are several ways of integrating the dyes needed to create the desired spectral profile of the film. Exemplary dye-integration methods include vapor deposition, chemically cross linked within the film, dissolved within small polymer micro-spheres and then integrated within the film. Suitable dyes are commercially available from companies including Keystone, BPI & Phantom.

Most dyeing of spectacle lenses is done after the lens has been shipped from the manufacturer. Therefore, it may be desirable to incorporate a blue-absorbing dye during the manufacture of the lens itself. To do so, the filtering and color balancing dyes may be incorporated into a hard coating and/or an associated primer coating which promotes adhesion of the hard coating to the lens material. For example, a primer coat and associated hard coat are often added to the top of a spectacle lens or other ophthalmic system at the end of the manufacturing process to provide additional durability and scratch resistance for the final product. The hard coat typically is an outer-most layer of the system, and may be placed on the front, back, or both the front and back surfaces of the system.

Figure 47:
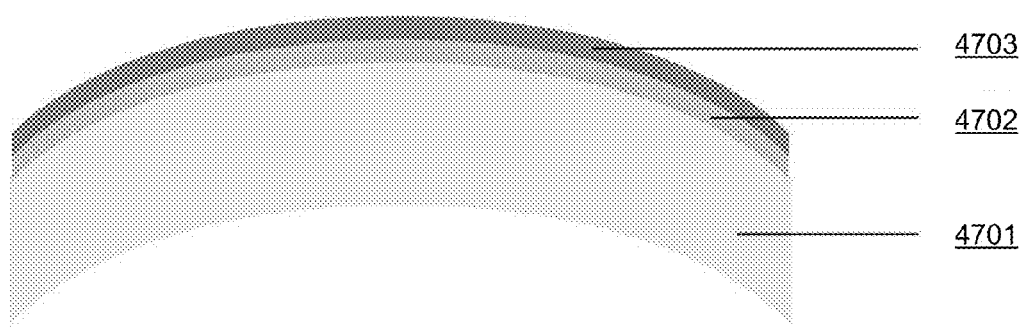
FIG. 47 shows an ophthalmic system having a hard coat.

FIG. 47 shows an exemplary system having a hard coating 4703 and its associated adhesion-promoting primer coat 4702. Exemplary hard coatings and adhesion promoting primer coating are available from manufacturers such as Tokuyama, UltraOptics, SDC, PPG, and LTI.

In one embodiment, both a blue blocking dye and a color balancing dye may be included in the primer coating 1802. Both the blue blocking and color balancing dyes also may be included in the hard coating 1803. The dyes need not be included in the same coating layer. For example, a blue blocking dye may be included in the hard coating 1803, and a color balancing dye included in the primer coating 1802. The color balancing dye may be included in the hard coating 1803 and the blue blocking dye in the primer coating 1802.

Primer and hard coats may be deposited using methods known in the art, including spin-coating, dip-coating, spray-coating, evaporation, sputtering, and chemical vapor deposition. The blue blocking and/or color balancing dyes to be included in each layer may be deposited at the same time as the layer, such as where a dye is dissolved in a liquid coating material and the resulting mixture applied to the system. The dyes also may be deposited in a separate process or sub-process, such as where a dye is sprayed onto a surface before the coat is cured or dried or applied.

A hard coat and/or primer coat may perform functions and achieve benefits described herein with respect to a film. Specifically, the coat or coats may selectively inhibit blue light, while maintaining desirable photopic vision, scotopic vision, circadian rhythms, and phototoxicity levels. Hard coats and/or primer coats as described herein also may be used in an ophthalmic system incorporating a film as described herein, in any and various combinations. As a specific example, an ophthalmic system may include a film that selectively inhibits blue light and a hard coat that provides color correction.

The selective filter can also provide increased contrast sensitivity. Such a system functions to selectively filter harmful invisible and visible light while having minimal effect on photopic vision, scotopic vision, color vision, and/or circadian rhythms while maintaining acceptable or even improved contrast sensitivity. In certain embodiments, the end residual color of the device to which the selective filter is applied is mostly colorless, and in other embodiments where a mostly clear residual color is not required the residual color can be yellowish. Preferably, the yellowness of the selective filter is unobjectionable to the subjective individual wearer. Yellowness can be measured quantitatively using a yellowness index such as ASTM E313-05. Preferably, the selective filter has a yellowness index that is no more than 50, 40, 35, 30, 25, 23, 20, 15, 10, 9, 7, or 5.

The system could include selective light wavelength filtering embodiments such as: windows, automotive windshields, light bulbs, flash bulbs, fluorescent lighting, LED lighting, television, computer monitors, etc. Any light that impacts the retina can be selectively filtered by the system. The system can be enabled, by way of example only, a film comprising a selective filtering dye or pigment, a dye or pigment component added after a substrate is fabricated, a dye component that is integral with the fabrication or formulation of the substrate material, synthetic or non-synthetic pigment such as melanin, lutein, or zeaxanthin, selective filtering dye or pigment provided as a visibility tint (having one or more colors) as in a contact lens, selective filtering dye or pigment provided in an ophthalmic scratch resistant coating (hard coat), selective filtering dye or pigment provided in an ophthalmic anti-reflective coat, selective light wave length filtering dye or pigment provided in a hydrophobic coating, an interference filter, selective light wavelength filter, selective light wavelength filtering dye or pigment provided in a photochromic lens, or selective light wavelength filtering dye or pigment provided in a matrix of a light bulb or tube. The system can selectively filter out one specific range of wavelengths, or multiple specific ranges of wavelengths, but not filter out wavelengths evenly across the visible spectrum.

Those skilled in the art will know readily how to provide the selective light wavelength filter to the substrate material. By way of example only, the selective filter can be: imbibed, injected, impregnated, added to the raw materials of the substrate, added to the resin prior to polymerization, layered within in the optical lens by way of a film comprising the selective filter dye or pigments.

Figure 48:
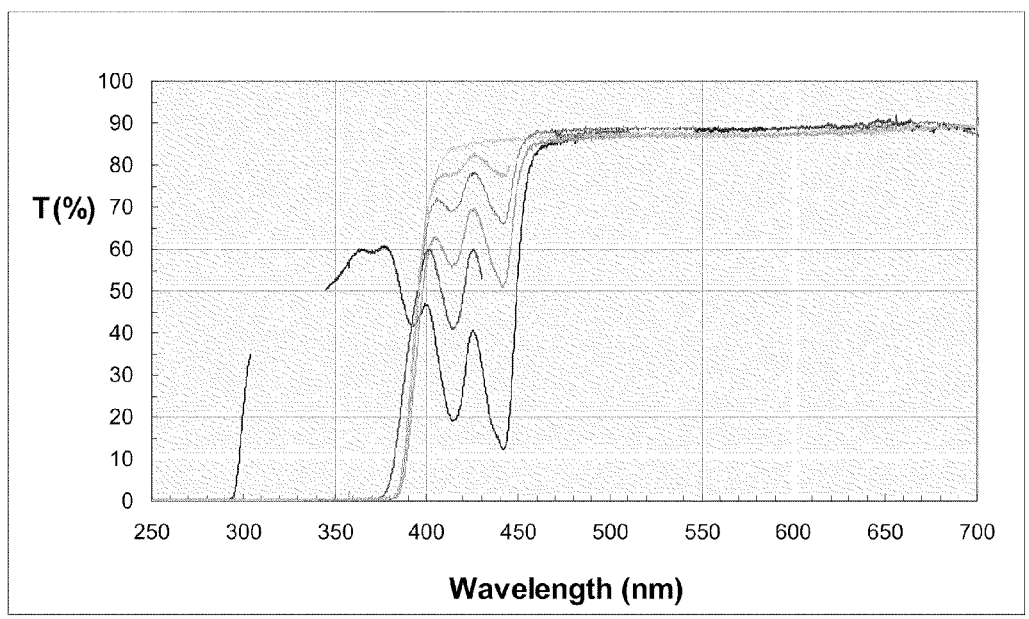
FIG. 48 shows the transmittance as a function of wavelength for a selective filter with strong absorption band around 430 nm.

The system may utilize a proper concentration of a dye and or pigment such as, by way of example only, perylene, porphrin or their derivatives. Refer to FIG. 48 to observe varying concentration of perylene and the functional ability to block wavelengths of light at around 430 nm. The transmission level can be controlled by dye concentration. Other dye chemistries allow adjustment of the absorption peak positions.

Perylene at appropriate concentration levels in an appropriate base material provides balance in photopic, scotopic, circadian, and phototoxicity ratios while maintaining a mostly colorless appearance:

TABLE V

| Reference | Photopic Ratio - $V_\lambda$ (%) | Scotopic Ratio - $V'_\lambda$ (%) | Phototoxicity Ratio ($B_\lambda$) (%) | Circadian Ratio ($M'_\lambda$) (%) |
|---|---|---|---|---|
| Unfiltered | 100 | 100 | 100 | 100 |
| Polycarbonate - undyed | 88 | 87 | 86 | 74 |
| Pratt | 28 | 16 | 4 | 7 |
| Mainster | 86 | 78 | 39 | 46 |
| Mainster (−20 nm shift) | 86 | 83 | 63 | 56 |
| Mainster (+20 nm shift) | 84 | 68 | 15 | 32 |
| HPOO dye (2x) | 88 | 81 | 50 | 62 |
| HPOO dye (x) | 88 | 84 | 64 | 63 |
| HPOO (x/2) | 87 | 84 | 72 | 66 |
| HPOO (x/4) | 89 | 87 | 79 | 71 |

Increases in contrast sensitivity are observed with appropriate concentration of perylene. See Example 2, Table VI. The family of perylene based dyes or pigments are exemplary dyes. When such a dye is used, depending upon the embodiment or application, the dye may be formulated such that it is bonded molecularly or chemically to the substrate or a coating that is applied to the substrate such that the dye does not leach out. By way of example only, applications of this would be for use with contact lenses, IOLs, corneal in-lays, corneal on-lays, etc.

Selective filters can be combined to hinder other target wavelengths as science discovers other visible light wavelength hazards.

In one embodiment, a contact lens is comprised of a perylene dye formulated such that it will not leach out of the contact lens material. The dye is further formulated such that it provides a tint having a yellow cast. This yellow cast allows for the contact lens to have what is known as a handling tint for the wearer. The perylene dye or pigment further provides the selective filtering as shown by FIG. 48. This filtering provides retinal protection and enhanced contrast sensitivity without compromising in any meaningful way one's photopic vision, scotopic vision, color vision, or circadian rhythms.

In the case of the inventive embodiment of a contact lens the dye or pigment can be imparted into the contact lens by way of example only, by imbibing, so that it is located within a central 10 mm diameter or less circle of the contact lens, preferably within 6-8 mm diameter of the center of the contact lens coinciding with the pupil of the wearer. In this embodiment the dye or pigment concentration which provides selective light wavelength filtering is increased to a level that provides the wearer with an increase in contrast sensitivity (as oppose to without wearing the contact lens) and without compromising in any meaningful way (one or more, or all of) the wearer's photopic vision, scotopic vision, color vision, or circadian rhythms.

Preferably, an increase in contrast sensitivity is demonstrated by an increase in the user's Functional Acuity Contrast Test (FACT) score of at least about 0.1, 0.25, 0.3, 0.5, 0.7, 1, 1.25, 1.4, or 1.5. With respect to the wearer's photopic vision, scotopic vision, color vision, and/or circadian rhythms, the ophthalmic system preferably maintains one or all of these characteristics to within 15%, 10%, 5%, or 1% of the characteristic levels without the ophthalmic system.

In another inventive embodiment that utilizes a contact lens the dye or pigment is provided that causes a yellowish tint that it is located over the central 5-7 mm diameter of the contact lens and wherein a second color tint is added peripherally to that of the central tint. In this embodiment the dye concentration which provides selective light wavelength filtering is increased to a level that provides the wearer very good contrast sensitivity and once again without compromising in any meaningful way (one or more, or all of) the wearer's photopic vision, scotopic vision, color vision, or circadian rhythms.

In still another inventive embodiment that utilizes a contact lens the dye or pigment is provided such that it is located over the full diameter of the contact lens from approximately one edge to the other edge. In this embodiment the dye concentration which provides selective light wavelength filtering is increased to a level that provides the wearer very good contrast sensitivity and once again without compromising in any meaningful way (one or more, or all of) the wearer's photopic vision, scotopic vision, color vision, or circadian rhythms.

When various inventive embodiments are used in or on human or animal tissue the dye is formulated in such a way to chemically bond to the inlay substrate material thus ensuring it will not leach out in the surrounding corneal tissue. Methods for providing a chemical hook that allow for this bonding are well known within the chemical and polymer industries.

In still another inventive embodiment an intraocular lens includes a selective light wavelength filter that has a yellowish tint, and that further provides the wearer improved contrast sensitivity without compromising in any meaningful way (one or more, or all of) the wearer's photopic vision, scotopic vision, color vision, or circadian rhythms. When the selective filter is utilized on or within an intra-ocular lens it is possible to increase the level of the dye or pigment beyond that of a spectacle lens as the cosmetics of the intra-ocular lens are invisible to someone looking at the wearer. This allows for the ability to increase the concentration of the dye or pigment and provides even higher levels of improved contrast sensitivity without compromising in any meaningful way (one or more, or all of) the wearer's photopic vision, scotopic vision, color vision, or circadian rhythms.

In still another embodiment, a spectacle lens includes a selective light wave length filter comprising a dye having perylene wherein the dye's formulation provides a spectacle lens that has a mostly colorless appearance. And furthermore that provides the wearer with improved contrast sensitivity without compromising in any meaningful way (one or more, or all of) the wearer's photopic vision, scotopic vision, color vision, or circadian rhythms. In this particular embodiment, the dye or pigment is imparted within a film that is located within or on the surface of the spectacle lens.

In another embodiment, the system can be a corneal inlay. Similar to the other blue-blocking ophthalmic systems described herein, the corneal inlay can provide protection to a plurality of ocular structures within the eye while maintaining acceptable color cosmetics, color perception, overall light transmission, photopic vision, scotopic vision, color vision, and/or cirdadian rhythms. The corneal inlay can provide proper corneal metabolism. Furthermore, the corneal inlay can also include a pinhole effect to improve clear near-point vision and increase depth of focus. In some embodiments, the corneal inlay can also correct refractive errors including, but not limited to, higher order aberration, lower order aberration, myopia, hyperopia, astigmatism, and/or presbyopia.

The selective filtering of blue light wavelengths can be achieved by any material known in the art including, but not limited to, one or more blue-blocking dyes as described above. Suitable dyes include, but are not limited to, perylene, porphyrin, coumarin, acridine, derivatives thereof, or compounds that mimic the transmission spectra thereof.

One or more blue-blocking dyes can be added to the biocompatible material during or after processing by way of any technique known in the art of optical manufacturing. For example, a dye can be incorporated directly into the substrate, added to a polymeric coating, imbibed into the inlay, incorporated in a laminated structure that includes a dye-impregnated layer, or as a composite material with dye-impregnated microparticles.

Regardless of incorporation technique, the dye should be prevented from leaching out into the surrounding cornea. For example, the dye can be covalently bound to the substrate material. Alternatively, the dye can be imbibed, dispersed, or dissolved in the substrate and encapsulated in a cross-linked polymer to inhibit diffusion of the dye out of the corneal inlay. Optionally, a sealing layer can be placed on the corneal implant. A sealing layer can be, for example, a sealer-like coating, a thin polymer layer, or a layer that is laminated within the corneal inlay comprising the dye(s).

In one embodiment, the corneal inlay further comprises a UV-inhibiting material, e.g., a UV-blocking dye. UV-inhibiting materials are well-known in the art and are used in many ophthalmic lens applications. In one embodiment, an ultraviolet-inhibiting material blocks at least about 90%, preferably at least about 95%, or at least about 99% of light at wavelengths of less than about 400 nm, preferably about 280 nm to about 400 nm or increments therein, such as about 280 nm to about 315 nm.

In one embodiment, the corneal inlay can provide a pinhole effect to enhance the depth perception and near-point focus of the wearer. In another embodiment, the pinhole effect can be created by any ophthalmic system described herein, e.g., a spectacle lens, contact lens, intra-ocular lens, corneal inlay, and corneal onlay. The pinhole effect can be created by providing a central zone, which allows a high transmission of visible light, and a peripheral region, which limits the transmission of visible light. The central zone and peripheral region act as a static shutter or lens stop. "Static" means fixed, i.e., not dynamic. The pinhole effect can be created by, for example, an opaque, frosted, crazed, or defocused peripheral region with a central transmissive, un-frosted, un-crazed, or focused zone (FIG. 49B). The diameter of the central zone is preferably about 2.5 mm to about 1 mm or increments therein, or about 1.5 mm. The central zone can be circular, or it can be any other shape in the interior of the inlay. For example, the central zone can be a symmetrical, asymmetrical, geometric, curved, or irregular shape. Preferably, the central zone is circular and is centered in the inlay.

The pinhole effect can increase depth of focus and enhance near-focus vision for a presbyopic or emerging-presbyopic individual. A pinhole corneal inlay can be implanted in one or both eyes of a patient. In one embodiment, a pinhole corneal inlay is implanted in a monocular manner, i.e., in only one eye of a patient. In this embodiment, the pinhole corneal inlay is preferably implanted into the non-dominant eye. A corneal inlay without a pinhole effect, such as a blue-blocking corneal inlay described herein, can be implanted in the dominant eye. Preferably, both eyes receive a corneal inlay comprising the blue-blocking and/or UV-blocking features described herein.

In one embodiment of the pinhole corneal inlay, the central zone includes a blue-blocking component. For example, the central zone includes one or more dyes that selectively inhibit light within a range of blue light wavelengths as described above. This embodiment surprisingly both protects the retina from harmful blue light wavelengths while also enhancing depth perception. The pinhole effect depends on the difference in contrast between the central zone and the peripheral region. One might predict that including a dye in the central zone would decrease the contrast differential between the central zone and the peripheral region and thus eliminate the pinhole effect and its accompanying enhancement of depth perception. However, the inventors have discovered that even with the blue-blocking dye, the contrast differential can be sufficiently maintained to achieve the pinhole effect.

The central zone and the peripheral region can be designed to maintain a contrast differential of at least about 60%, at least about 65%, at least about 70%, at least about 80%, or at least about 90%. In one embodiment, the contrast differential is about 60% to about 80% or increments therein, such as about 60% to about 65%, and about 70% to about 80%. The transmission of visible light through the center zone can be, for example, about 80% to about 95% or increments therein, about 85% to about 95%, or about 90%. The transmission of visible light through the peripheral region can be, for example, about 15% to about 30% or increments therein, about 20% to about 30%, or about 20% to about 25%. The transmission of visible light can be measured by, e.g., average transmission or preferably by luminous transmission.

Proper corneal metabolism can be achieved by selecting bio-compatible materials, properly positioning the corneal inlay, and/or providing micro-apertures as described below. The inventive corneal inlay can be made of various bio-compatible materials including, but not limited to, a non-hydrogel, microporous, ophthalmic perfluoropolyether material; a polyvinylidene fluoride material; or any other suitable plastic material known in the field of ophthalmics.

Figure 49A:
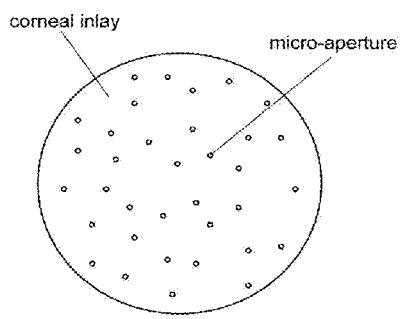
FIG. 49A-E show embodiments of corneal inlays.
Figure 49B:
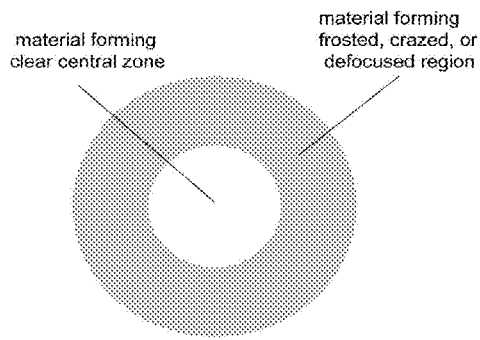

The corneal inlay can include a plurality of micro-apertures (FIG. 49A). The micro-apertures can be created during or after processing of the bio-compatible material. The micro-apertures allow for proper corneal metabolism including fluids, nutrients, solutes, and extracellular transport. The micro-apertures can be formed throughout the entirety of the corneal inlay, or any portion thereof. For example, in the pinhole corneal inlay described below, the micro-apertures can be formed in the peripheral region and/or in the central zone. In one embodiment, the micro-apertures are formed only in the peripheral region.

The diameter of the corneal inlay can be about 3.5 mm to about 7 mm or increments therein, such as about 4 mm. The thickness of the corneal can be about 5 microns to about 15 microns or increments therein, such as about 10 microns. For embodiment including micro-apertures, the micro-apertures have an average diameter of about 1 micron to 100 microns or increments therein, such as about 50 microns to about 75 microns.

The corneal inlay can be implanted into the eye by any known methodology and/or the methodology described herein. For example, the cornea can be prepared to receive the corneal inlay by sectioning the cornea to create a corneal flap having the proper thickness, diameter, and location relative to the pupil and the limbus. The corneal flap can be created by, e.g., a mechanical microkeratome or femtosecond laser. Procedures for creating a corneal flap are well-known in the art and are used with LASIK procedures as well as other lamellar corneal surgical procedures.

In one embodiment, the flap is not removed from the cornea, but is folded out of the way as the corneal inlay is properly positioned into place. Once the corneal inlay is in place, the corneal flap is unfolded and positioned over the corneal inlay. The diameter of the corneal flap can be larger than that of the corneal inlay thus allowing for the cornea to seal and heal around the periphery of the corneal inlay.

The method for implanting the corneal inlay can further include a step of performing Laser-Assisted in situ Keratomileusis (LASIK) to alter the shape of the cornea. For example, after creating the corneal flap, a LASIK procedure can be performed to alter, improve, and/or correct a refractive error of the patient. A LASIK procedure can also be used to sculpt a more defined and deeper recess in the cornea to facilitate positioning of the corneal inlay. The corneal inlay can be positioned within a recess, and the corneal flap can be repositioned over the corneal inlay. In this way, a thicker corneal inlay can be implanted.

The corneal inlay may correct a lower order aberration or a higher order aberration as described below. Any of these corrections includes a complete correction of, or any improvement to, the refractive error of the wearer.

Figure 49C:
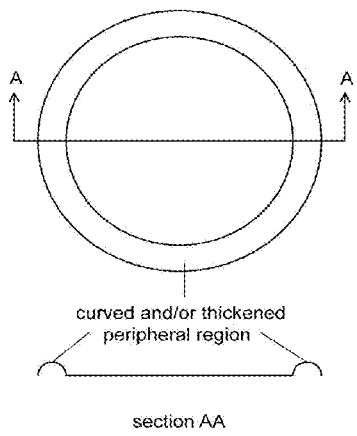

In one embodiment, the corneal inlay can correct a refractive error such as myopia, hyperopia, or astigmatism. The correction of refractive error can be achieved by one or more features including, but not limited to, curving the peripheral region of the corneal inlay, thickening the peripheral region of the corneal inlay, altering the diameter of the corneal inlay (FIG. 49C). The corneal inlay can cause refractive changes and/or reshape the external corneal curvature.

Figure 49D:
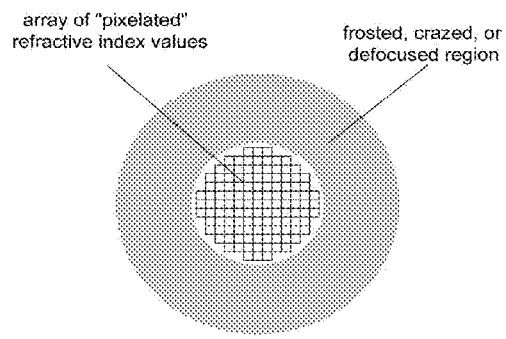
Figure 49E:
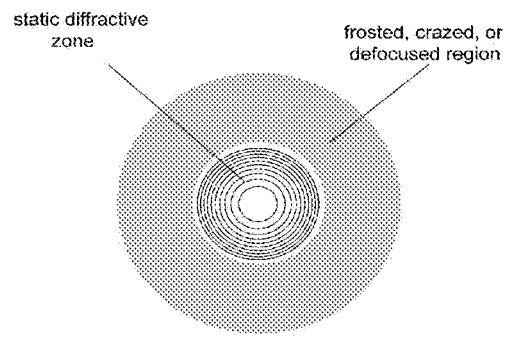

In another embodiment, the corneal inlay can correct a refractive error, including presbyopia, by way of diffraction. In this embodiment, the corneal inlay includes a diffractive design pattern (FIG. 49E) on an external surface of the corneal inlay or embedded in the interior of the corneal inlay.

In yet another embodiment, the central zone of the corneal inlay includes a plurality of pixel-like index of refractive changes (FIG. 49D) to impart an index change. Index changes can provide spherical refractive changes and/or correct for higher order aberration. Higher order aberrations are refractive error aberrations other than myopia, hyperopia, regular astigmatism, and presbyopia. One embodiment is a method of correcting for higher order aberration by performing a wavefront measurement of the wearer, then correcting the wavefront measurement by implanting a corneal inlay including a plurality of index changes. This corneal inlay can be created, e.g., by curing the polymer of the corneal inlay (or a layer of modifiable polymer material affixed to the corneal inlay) to provide a predictable and desired localized index of refraction changes. In another embodiment, the index changes can be imparted in situ by a final cure of the corneal inlay (either of the entire material structure, or a layer of material that is present on, or located inside of, the corneal inlay) after the corneal inlay is implanted within the cornea. The final cure can be performed by, e.g., a specified and targeted light radiation cure, occurring almost simultaneously in a mostly closed loop manner to refine and perfect the higher order aberration correction. Thus, a method of correcting higher order aberration can include performing an iterative wavefront analysis while curing the corneal inlay to impart an index change.

The wavefront analysis and in situ curing method described above can also be used to correct for lower order aberrations such as myopia, hyperopia, regular astigmatism, and presbyopia. Wavefront analysis and photo-curing polymers using visible and non-visible light sources are both well-known in the art. To determine the refractive error of the patient, one or more of a wavefront aberrometer, an auto-refractor, and/or a manual refractor can be used. The methods can include one, two, or more refining steps achieve the final optical correction of the corneal inlay when using the inventive closed loop method previously described.

Any one or more of the above-described features—inhibiting UV light; inhibiting a range of blue light wavelengths; static shuttering; correcting refractive error; correcting lower order aberration including myopia, hyperopia, regular astigmatism, and presbyopia; and correcting higher order aberration—can be used with any embodiment described herein.

EXAMPLES

Example 1

Figure 45:
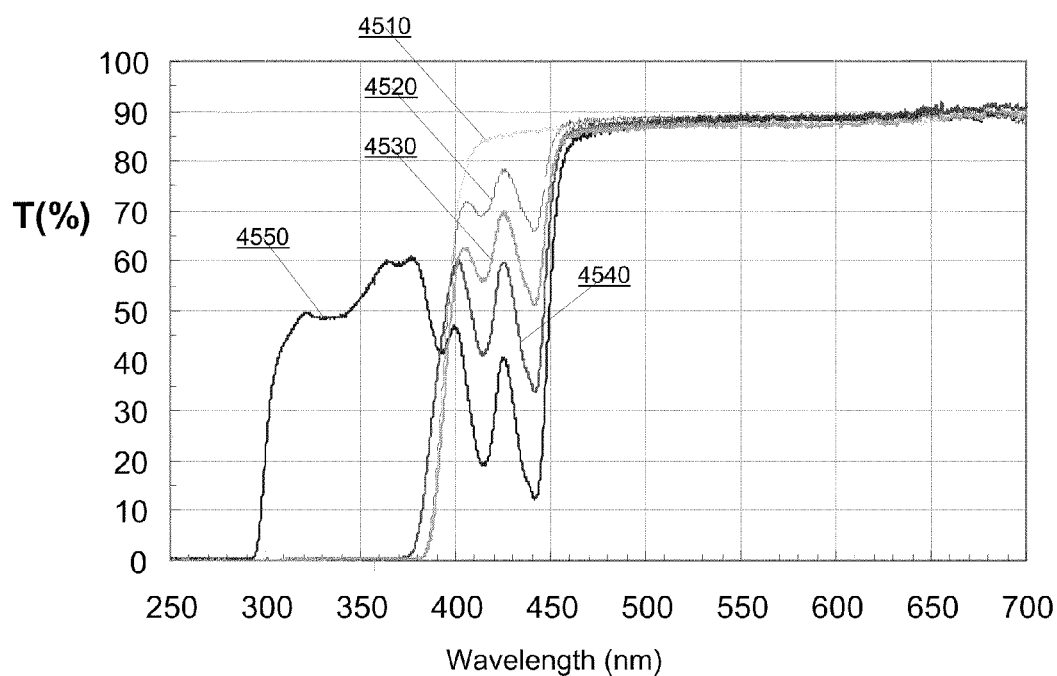
FIG. 45 shows transmission spectra for various lenses.

A polycarbonate lens having an integral film with varying concentrations of blue-blocking dye was fabricated and the transmission spectrum of each lens was measured as shown in FIG. 45. Perylene concentrations of 35, 15, 7.6, and 3.8 ppm (weight basis) at a lens thickness of 2.2 mm were used. Various metrics calculated for each lens are shown in Table IV, with references corresponding to the reference numerals in FIG. 45. Since the selective absorbance of light depends primarily on the product of the dye concentration and coating thickness according to Beer's law, it is believed that comparable results are achievable using a hard coat and/or primer coat in conjunction with or instead of a film.

TABLE IV

| Lens | Ref. | Photopic Ratio ($V_\lambda$) | Scotopic Ratio ($V'_\lambda$) | Circadian Ratio ($M'_\lambda$) | Phototoxicity Ratio ($B_\lambda$) |
| --- | --- | --- | --- | --- | --- |
| Unfiltered light (no lens) | | 100.0% | 100.0% | 100.0% | 100.0% |
| Polycarbonate Lens (no dye) | 4510 | 87.5% | 87.1% | 74.2% | 85.5% |
| 3.8 ppm (2.2 mm) | 4520 | 88.6% | 86.9% | 71.0% | 78.8% |
| 7.6 ppm (2.2 mm) | 4530 | 87.0% | 84.1% | 65.9% | 71.1% |
| 15 ppm (2.2 mm) | 4540 | 88.3% | 83.8% | 63.3% | 63.5% |
| 35 ppm (2.2 mm) | 4550 | 87.7% | 80.9% | 61.5% | 50.2% |

With the exception of the 35 ppm dyed lens, all the lenses described in Table IV and FIG. 45 include a UV dye typically used in ophthalmic lens systems to inhibit UV wavelengths below 380 nm. The photopic ratio describes normal vision, and is calculated as the integral of the filter transmission spectrum and $V\lambda$ (photopic visual sensitivity) divided by the integral of unfiltered light and this same sensitivity curve. The scotopic ratio describes vision in dim lighting conditions, and is calculated as the integral of the filter transmission spectrum and $V\lambda$ (scotopic visual sensitivity) divided by the integral of unfiltered light and this same sensitivity curve. The circadian ratio describes the effect of light on circadian rhythms, and is calculated as the integral of the filter transmission spectrum and $M\lambda$ (melatonin suppression sensitivity) divided by the integral of unfiltered light and this same sensitivity curve. The phototoxicity ratio describes damage to the eye caused by exposure to high-energy light, and is calculated as the integral of the filter transmission and the $B\lambda$ (phakic UV-blue phototoxicity) divided by the integral of unfiltered light and this same sensitivity curve. Response functions used to calculate these values correspond to those disclosed in Mainster and Sparrow, "How Much Blue Light Should an IOL Transmit?" Br. J. Opthalmol., 2003, v. 87, pp. 1523-29, Mainster, "Intraocular Lenses Should Block UV Radiation and Violet but not Blue Light," Arch. Ophthal., v. 123, p. 550 (2005), and Mainster, "Violet and Blue Light Blocking Intraocular Lenses: Photoprotection vs. Photoreception", Br. J. Opthalmol, 2006, v. 90, pp. 784-92. For some applications, a different phototoxicity curve is appropriate but the methodology for calculation is the same. For example, for intraocular lens (IOL) applications, the aphakic phototoxicity curve should be used. Moreover, new phototoxicity curves may be applicable as the understanding of the phototoxic light mechanisms improves.

As shown by the exemplary data described above, a system may selectively inhibit blue light, specifically light in the 400 nm-460 nm region, while still providing a photopic luminous transmission of at least about 85% and a phototoxicity ration of less than about 80%, more preferably less than about 70%, more preferably less than about 60%, and more preferably less than about 50%. As previously described, a photopic luminous transmission of up to 95% or more also may be achievable using the techniques described herein.

The principles described herein may be applied to varied illuminants, filters, and skin tones, with the objective of filtering some portion of phototoxic blue light while reducing pupil dilation, scotopic sensitivity, color distortion through the ophthalmic device, and cosmetic color of an external ophthalmic device from the perspective of an observer that views the person wearing the device on their face.

Several embodiments of the invention are specifically illustrated and/or described herein. However, it will be appreciated that modifications and variations of the invention are covered by the above teachings and within the purview of the appended claims without departing from the spirit and intended scope of the invention. For examples, although the methods and systems described herein have been described using examples of specific dyes, dielectric optical filters, skin tones, and illuminants, it will be understood that alternative dyes, filters, skin colors, and illuminants may be used.

Example 2

Nine patients were tested for contrast sensitivity using dye concentrations of 1× and 2× against a clear filter as a control. 7 of the 9 patients showed overall improved contrast sensitivity according to the Functional Acuity Contrast Test (FACT). See Table VI:

TABLE VI

Contrast sensitivity test for dye samples with loadings of X and 2X. Test was done February, 2007 at Vision Associates in Havre de Grace, Maryland by Dr. Andy Ishak. The test consisted of 10 patients, each tested with two filters, using the FACT contrast sensitivity testing process

| | | | Dotted A | | | Dotted B | | | Dotted C | | | Dotted D | | | Dotted E | | | Solid A | | | Solid B | | | Solid C | | | Solid D | | | Solid E | | | Tot Diff | Number Better (gr) | Worse (rd) |
|---|---|---|---|---|---|---|---|---|---|---|---|---|---|---|---|---|---|---|---|---|---|---|---|---|---|---|---|---|---|---|---|---|---|---|---|
| | | NO | Lt | Dk | NO | Lt | Dk | NO | Lt | Dk | NO | Lt | Dk | NO | Lt | Dk | NO | Lt | Dk | NO | Lt | Dk | NO | Lt | Dk | NO | Lt | Dk | NO | Lt | Dk | | | |
| 1 | JP | 5 | 6 | 6 | 6 | 6 | 6 | 6 | 6 | 6 | 5 | 5 | 5 | 4 | 4 | 4 | 7 | 6 | 7 | 6 | 6 | 7 | 6 | 7 | 6 | 5 | 5 | 5 | 5 | 2 | 4 | | (gr) | (rd) |
| 2 | BJ | 6 | 7 | 7 | 7 | 7 | 7 | 6 | 6 | 6 | 3 | 3 | 3 | 4 | 3 | 3 | 7 | 5 | 6 | 7 | 7 | 7 | 8 | 7 | 7 | 6 | 6 | 6 | 4 | 5 | 5 | -1 | 4 | 3 |
| 3 | JB | 8 | 8 | 8 | 6 | 6 | 6 | 6 | 5 | 6 | 5 | 4 | 5 | 4 | 3 | 3 | 9 | 9 | 9 | 7 | 9 | 9 | 8 | 8 | 8 | 6 | 6 | 6 | 4 | 4 | 5 | | | |
| 4 | AW | 7 | 8 | 8 | 6 | 7 | 8 | 7 | 7 | 7 | 5 | 5 | 5 | 3 | 4 | 3 | 6 | 7 | 7 | 6 | 6 | 7 | 5 | 6 | 7 | 4 | 4 | 4 | 0 | 1 | 4 | -5 | 4 | 4 |
| 5 | LL | 6 | 6 | 6 | 6 | 6 | 6 | 6 | 6 | 6 | 5 | 5 | 6 | 4 | 3 | 4 | 6 | 6 | 6 | 6 | 5 | 6 | 6 | 6 | 7 | 4 | 4 | 6 | 3 | 5 | 6 | 19 | 10 | 1 |
| 6 | TS | 7 | 9 | 9 | 8 | 9 | 9 | 8 | 9 | 8 | 6 | 7 | 7 | 4 | 5 | 5 | 5 | 8 | 8 | 6 | 8 | 8 | 7 | 8 | 8 | 4 | 4 | 4 | 2 | 4 | 2 | 21 | 15 | 1 |
| 7 | KS | 6 | 6 | 6 | 5 | 5 | 5 | 4 | 4 | 4 | 3 | 2 | 2 | 2 | 1 | 1 | 5 | 3 | 3 | 5 | 5 | 4 | 2 | 4 | 4 | 1 | 0 | 1 | | 0 | 4 | 16 | 9 | 6 |
| 9 | DS | 5 | 6 | 6 | 5 | 7 | 7 | 6 | 6 | 6 | 3 | 5 | 5 | 3 | 4 | 4 | 5 | 6 | 7 | 6 | 6 | 6 | 5 | 5 | 5 | 2 | 4 | 4 | 2 | 3 | 3 | 27 | 17 | 0 |
| 10 | NK | | | | | | | | | | | | | | | | 9 | 9 | 9 | 9 | 9 | 8 | 7 | 7 | 8 | 5 | 5 | 7 | 4 | 6 | 8 | -1 | 4 | 2 |
| Tot | | 51 | 55 | 56 | 49 | 54 | 54 | 44 | 46 | 47 | 31 | 35 | 37 | 21 | 29 | 29 | 59 | 62 | 64 | 58 | 61 | 62 | 50 | 58 | 57 | 35 | 34 | 39 | 29 | 34 | 38 | 25 | 16 | 0 |
| Delta | | | 4 | 5 | | 5 | 5 | | 2 | 3 | | 4 | 6 | | 8 | 8 | | 3 | 5 | | 3 | 4 | | 8 | 7 | | 4 | 13 | | 5 | 9 | 10 | 5 | 1 |
| Avg. | | 6.4 | 6.9 | 7.0 | 6.1 | 6.8 | 6.8 | 5.5 | 5.8 | 5.9 | 3.9 | 4.4 | 4.6 | 2.6 | 3.6 | 3.6 | 6.6 | 6.9 | 7.1 | 6.4 | 6.8 | 6.9 | 5.6 | 6.4 | 6.3 | 3.9 | 4.3 | 5.3 | 3.2 | 3.8 | 4.2 | 111 | | |
| Delta | | | 0.5 | 0.6 | | 0.6 | 0.6 | | 0.3 | 0.4 | | 0.5 | 0.8 | | 1.0 | 1.0 | | 0.3 | 0.6 | | 0.3 | 0.4 | | 0.9 | 0.8 | | 0.4 | 1.4 | | 0.6 | 1.0 | 5.6 | | |
| Better (gr) | | 4 | 5 | | 4 | 4 | | 3 | 4 | | 3 | 5 | | 4 | 5 | | 4 | 3 | | 2 | 4 | | 5 | 5 | | 5 | 6 | | 5 | 5 | | | | |
| Worse (rd) | | 2 | 1 | | 1 | 2 | | 3 | 2 | | 2 | 1 | | 3 | 3 | | 3 | 2 | | 2 | 3 | | 2 | 2 | | 2 | 1 | | 2 | 2 | | | | |

Comments:
1 Patient number 8 data was dropped. This patient was a 60 yr old, diabetic, with cataracts
2 Patient 10 was tested in one eye only
3 The terms dotted and solid refer to the two eyes of the patients, how they were shown on test result forms
4 The headings "NO", refer to lenses with clear filter, ie control. The terms Lt and Dk refer to the dye loading in the tested filters.
5 For each patient, the top line is their actual score. Second line is the difference with filters versus non filtered "control"
6 Boxes marked with GREEN showed improvement, boxes with RED showed negative results.
7 Total scores (line 22) add up how all patients scored on a specific test column
8 Total Difference (column 33) shows how each patient scored overall on all 5 test columns (A-E) for both eyes TABLE VI-continued Contrast sensitivity test for dye samples with loadings of X and 2X. Test was done February, 2007 at Vision Associaates in Havre de Grace, Maryland by Dr. Andy Ishak.
The test consisted of 10 patients, each tested with two filters, using the FACT contrast sensitivity testing process 9 Note, each patient (except #10) had 20 opportunities to score a difference—2 eyes x 5 columns on the test x 2 filters
10 Better and Worse numbers (rows 27-28, columns 34-35) simply add up the opportunities that scored better with the filters or worse, versus the clear control
Results
1 7 of the 9 patients showed overall improved contrast sensitivity results (columns 33-35)
2 Patients overall showed improvement in both eyes on 18 of the 20 opportunities (2 eyes x two filters x five FACT columns) (rows 27-28)
3 On average, patients improved by 0.3-1.4 for all 20 opportunities (row 25)

What is claimed is:

1. An ophthalmic system comprising:
   an ophthalmic lens selected from the group consisting of a contact lens, intra-ocular lens, corneal inlay, and corneal onlay having:
   a central zone that selectively inhibits a range of blue light wavelengths, and
   a peripheral region, wherein the contrast differential between the central zone and the peripheral region is at least about 60%;
   wherein the central zone and peripheral region form a static pinhole.

2. An ophthalmic system comprising:
   an ophthalmic lens selected from the group consisting of a contact lens, intra-ocular lens, corneal inlay, and corneal onlay having:
   a central zone that selectively inhibits a range of blue light wavelengths, and
   a peripheral region, wherein the contrast differential between the central zone and the peripheral region is at least about 60%;
   wherein white light has a CIE of (0.33±0.05, 0.33±0.05) when transmitted through the lens.

3. The system of claim 2, wherein the luminous transmission of visible light through the center zone is about 80% to about 95%.

4. The system of claim 2, wherein the luminous transmission of visible light through the peripheral region is about 15% to about 30%.

5. The system of claim 2, wherein the central zone comprises a bio-compatible plastic material and at least one dye.

6. The system of claim 5, wherein at least one dye is perylene, porphyrin, coumarin, acridine, a derivative thereof, or a compound that mimics the transmission spectra thereof.

7. The system of claim 6, wherein the dye is perylene.

8. The system of claim 2, wherein the central zone inhibits a range of blue light wavelengths from about 400 nm to about 460 nm.

9. The system of claim 2, wherein the central zone inhibits a range of blue light wavelengths between about 400 nm to about 500 nm, wherein the inhibited range of blue light wavelengths has full-width at half-maximum of no more than about 60 nm.

10. The system of claim 2, further comprising an ultraviolet-inhibiting material.

11. The system of claim 10, wherein the ultraviolet-inhibiting material inhibits at least 90% of ultraviolet light having wavelengths of about 280 nm to about 315 nm.

12. The system of claim 11, wherein the ultraviolet-inhibiting material inhibits at least 90% of ultraviolet light having wavelengths of less than about 400 nm.

13. The system of claim 2, wherein the ophthalmic lens is a corneal inlay.

14. The system of claim 2, wherein the central zone comprises at least one index change.

15. The system of claim 14, wherein the central zone comprises a plurality of index changes.

16. The system of claim 2, wherein the system corrects at least one refractive error selected from the group consisting of higher order aberration, lower order aberration, myopia, hyperopia, astigmatism, and presbyopia.

17. The system of claim 2, wherein the contrast differential between the central zone and the peripheral region is at least about 70%.

18. The system of claim 6, wherein the dye is magnesium tetraphenyl porphyrin.

* * * * *